(12) United States Patent
Bakker et al.

(10) Patent No.: US 11,739,148 B2
(45) Date of Patent: *Aug. 29, 2023

(54) HUMAN CD3 BINDING ANTIBODY

(71) Applicant: Merus N.V., Utrecht (NL)

(72) Inventors: Alexander Berthold Hendrik Bakker, Utrecht (NL); Pieter Fokko Van Loo, Utrecht (NL)

(73) Assignee: Merus N.V., Utrecht (NL)

( * ) Notice: Subject to any disclaimer, the term of this patent is extended or adjusted under 35 U.S.C. 154(b) by 914 days.

This patent is subject to a terminal disclaimer.

(21) Appl. No.: 16/245,846

(22) Filed: Jan. 11, 2019

(65) Prior Publication Data

US 2019/0211100 A1    Jul. 11, 2019

Related U.S. Application Data

(62) Division of application No. 15/888,757, filed on Feb. 5, 2018, now Pat. No. 10,266,593, which is a division of application No. 15/205,629, filed on Jul. 8, 2016, now Pat. No. 9,914,777.

(30) Foreign Application Priority Data

Jul. 10, 2015 (EP) .................................. 15176355

(51) Int. Cl.
  *C07K 16/28* (2006.01)
  *A61K 39/395* (2006.01)

(52) U.S. Cl.
  CPC .... *C07K 16/2809* (2013.01); *A61K 39/39591* (2013.01); *C07K 16/2851* (2013.01); *C07K 2317/21* (2013.01); *C07K 2317/31* (2013.01); *C07K 2317/51* (2013.01); *C07K 2317/515* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2317/71* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,801,687 A | 1/1989 | Ngo |
| 4,816,567 A | 3/1989 | Cabilly et al. |
| 5,151,504 A | 9/1992 | Croze |
| 5,457,035 A | 10/1995 | Baum et al. |
| 5,731,168 A | 3/1998 | Carter et al. |
| 7,642,228 B2 | 1/2010 | Carter et al. |
| 8,592,562 B2 | 11/2013 | Kannan et al. |
| 9,145,588 B2 | 9/2015 | Throsby et al. |
| 9,248,181 B2 | 2/2016 | De Kruif et al. |
| 9,248,182 B2 | 2/2016 | De Kruif et al. |
| 9,358,286 B2 | 6/2016 | De Kruif et al. |
| 9,758,805 B2 | 9/2017 | De Kruif et al. |
| 9,914,777 B2 | 3/2018 | Bakker et al. |
| 10,266,593 B2 | 4/2019 | Bakker et al. |
| 10,329,596 B2 | 6/2019 | De Kruif et al. |
| 10,337,045 B2 | 7/2019 | De Kruif et al. |
| 2003/0078385 A1 | 4/2003 | Arathoon et al. |
| 2005/0130224 A1 | 6/2005 | Saito et al. |
| 2006/0171929 A1 | 8/2006 | Clark et al. |
| 2006/0177451 A1 | 8/2006 | Van Den Oudenrijn et al. |
| 2006/0177896 A1 | 8/2006 | Mach et al. |
| 2009/0092582 A1 | 4/2009 | Bogin et al. |

(Continued)

FOREIGN PATENT DOCUMENTS

| | | |
|---|---|---|
| CN | 1984931 A | 6/2007 |
| EP | 0120694 A2 | 10/1984 |
| EP | 0314161 A1 | 5/1989 |
| EP | 0481790 A2 | 4/1992 |
| EP | 0523949 A1 | 1/1993 |
| EP | 1870459 A1 | 12/2007 |
| JP | H11500915 A | 1/1999 |
| JP | 2011508604 A | 3/2011 |
| WO | WO-9627011 A1 | 9/1996 |
| WO | WO-9850431 A2 | 11/1998 |
| WO | WO-0063403 A2 | 10/2000 |
| WO | WO-03004704 A2 | 1/2003 |

(Continued)

OTHER PUBLICATIONS

Armour, K.L. et al., "The contrasting IgG-binding interactions of human and herpes simplex virus Fc receptors," Mediation and Modulation of Antibody Function, Biochemical Society Transactions, vol. vol. 30(part 4): 495-500 (2002).

(Continued)

*Primary Examiner* — Brad Duffy
(74) *Attorney, Agent, or Firm* — Sterne, Kessler, Goldstein & Fox P.L.L.C.

(57) ABSTRACT

The invention is among others concerned with human CD3 binding antibodies comprising a heavy chain and light chain wherein said heavy chain comprises a variable region that comprises the amino acid sequence: QVQLV QSGGG VVQPG RSLRL SCVAS GFTFS SYGMH WVRQA PGKGL EWVAA IWYX$_1$X$_2$RKQDY ADSVK GRFTI SRDNS KNTLY LQMNS LRAED TAVYY CTRGT GYNWF DPWGQ GTLVT VSS with 0-5 amino acid insertions, deletions, substitutions, additions or a combination thereof at one or more positions other than the position indicated by X$_1$X$_2$; wherein X$_1$=N and X$_2$=A; X$_1$=N and X$_2$=T; X$_1$=S and X$_2$=G; X$_1$=H and X$_2$=G; X$_1$=D and X$_2$=G; or X$_1$=H and X$_2$=A. The invention is also concerned with bispecific antibodies that have a heavy chain as defined herein above. The invention is also concerned with methods of production of the antibody, cells producing the antibody and with (medical) uses of the antibody.

25 Claims, 20 Drawing Sheets

Specification includes a Sequence Listing.

(56) References Cited

U.S. PATENT DOCUMENTS

| | | |
|---|---|---|
| 2009/0182127 A1 | 7/2009 | Kjaergaard et al. |
| 2010/0015133 A1 | 1/2010 | Igawa et al. |
| 2010/0069614 A1 | 3/2010 | Houtzager et al. |
| 2010/0146647 A1 | 6/2010 | Logtenberg et al. |
| 2010/0286374 A1 | 11/2010 | Kannan et al. |
| 2010/0331527 A1 | 12/2010 | Davis et al. |
| 2011/0054151 A1 | 3/2011 | Lazar et al. |
| 2011/0195454 A1 | 8/2011 | McWhirter et al. |
| 2013/0096020 A1 | 4/2013 | Throsby et al. |
| 2013/0115208 A1 | 5/2013 | Ho et al. |
| 2013/0336981 A1 | 12/2013 | De Kruif et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2015/0139996 A1 | 5/2015 | De Kruif et al. |
| 2015/0196637 A1 | 7/2015 | De Kruif et al. |
| 2016/0130367 A1 | 5/2016 | Throsby et al. |
| 2016/0177364 A1 | 6/2016 | De Kruif et al. |
| 2016/0368988 A1 | 12/2016 | Bakker et al. |
| 2017/0037145 A1 | 2/2017 | Geuijen |
| 2017/0058035 A1 | 3/2017 | Logtenberg et al. |
| 2017/0369923 A1 | 12/2017 | De Kruif et al. |
| 2019/0352393 A1 | 11/2019 | Bakker et al. |

FOREIGN PATENT DOCUMENTS

| | | |
|---|---|---|
| WO | WO-03107218 A1 | 12/2003 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006105338 A2 | 10/2006 |
| WO | WO-2006106905 A1 | 10/2006 |
| WO | WO-2007033230 A2 | 3/2007 |
| WO | WO-2007110205 A2 | 10/2007 |
| WO | WO-2007147901 A1 | 12/2007 |
| WO | WO-2008027236 A2 | 3/2008 |
| WO | WO-2008119353 A1 | 10/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011028952 A1 | 3/2011 |
| WO | WO-2011028953 A1 | 3/2011 |
| WO | WO-2011143545 A1 | 11/2011 |
| WO | WO-2012020096 A1 | 2/2012 |
| WO | WO-2012023053 A2 | 2/2012 |
| WO | WO-2012058768 A1 | 5/2012 |
| WO | WO-2012131555 A2 | 10/2012 |
| WO | WO-2013157954 A1 | 10/2013 |
| WO | WO-2014051433 A1 | 4/2014 |

OTHER PUBLICATIONS

Canfield, S.M., et al., "The Binding Affinity of Human Igg for Its High Affinity Fc Receptor Is Determined by Multiple Amino Acids in the Ch2 Domain and Is Modulated by the Hinge Region," Journal of Experimental Medicine 173(6):1483-1491, Rockefeller University Press, United States (Jun. 1991).

Holliger, P., and Hudson, P.J., "Engineered Antibody Fragments and the Rise of Single Domains," Nature Biotechnology 23(9):1126-1136, Nature America Publishing, United States (2005).

Holt, L.J., et al., "Domain Antibodies: Proteins for Therapy," Trends in Biotechnology 21(11):484-490, Elsevier Science Publishers, England (2003).

Li, X., et al., "Structure Design of Bispecific Antibodies and progress in the Assembly Process," Chinese Journal of New Drugs 23(20):2430-2436, (2014).

Sugiyama, Y., et al., "In vitro Anti-tumor Activity of Anti-c-erbB-2.times.Anti-CD3 epsilon Bifunctional Monoclonal Antibody," Japanese Journal of Cancer Research, vol. 83 (6):563-567 (1992).

Transy, C., et al., "Most anti-human CD3 monoclonal antibodies are directed to the CD3 ∈ subunit," European Journal of Immunology 19(5):947-950, Wiley Online Library, United States (1989).

Byrne, H., et al., "A tale of two specificities: bispecific antibodies for therapeutic and diagnostic applications," Trends in Biotechnology 31(11):621-632, Cell Press, United States (2013).

Rajpal, A., et al., "Introduction: Antibody Structure and Function," Therapeutic Fc-Fusion Proteins, $1^{st}$ ED: 43 pg., Wiley-VCH Verlag GmbH & Co., Germany (2014).

Abbott, W.M., et al., "Current Approaches to Fine Mapping of Antigen-antibody Interactions," Immunology 142(4):526-535, Blackwell Scientific Publications, England (Aug. 2014).

Araya, C.L., et al., "Deep Mutational Scanning: Assessing Protein Function on a Massive Scale," Trends in Biotechnology 29(9):435-442, Elsevier Science Publishers, England (Sep. 2011).

Armour, K.L., et al., "Differential Binding to Human Fcgammariia and FcgammaRIIb Receptors by Human IgG Wildtype and Mutant Antibodies," Molecular Immunology 40(9):585-593, Pergamon Press, England (2003).

Atwell, S., et al., "Stable Heterodimers from Remodeling the Domain Interface of a Homodimer Using a Phage Display Library," Journal of Molecular Biology 270(1):26-35, Elsevier, England (1997).

Baeuerle, P., et al., "Bispecific T-Cell Engaging Antibodies for Cancer Therapy," Cancer Research, vol. 69(12), pp. 4941-4944 (2009).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Bargou, R., et al., "Tumor Regression in Cancer Patients by Very Low Doses of a T Cell-engaging Antibody," Science 321(5891):974-977, American Association for the Advancement of Science, United States (Aug. 2008).

Bendig, M.M., et al., "The Production of Foreign Proteins in Mammalian Cells," Genetic Engineering 7:91-127, Academic Press, England (1988).

Bluemel, C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy 59(8):1197-1209, Springer Verlag, Germany (Aug. 2010).

Bogan, A., et. al., "Anatomy of Hot Spots in Protein Interfaces," Journal of Molecular Biology, vol. 280, pp. 1-9 (1998).

Bostrom, J., et al., "Variants of the Antibody Herceptin that Interact with HER2 and VEGF at the Antigen Binding Site," Science 323(5921):1610-1614, American Association for the Advancement of Science, United States (Mar. 2009).

Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).

Carter, P., "Bispecific Human IgG by Design," Journal of Immunological Methods 248(1-2):7-15, Elsevier, Netherlands (2001).

Carter, P., et al., "Toward the Production of Bispecific Antibody Fragments for Clinical Applications," Journal of Hematotherapy, vol. 4, pp. 463-470 (1995).

Chames, P. and Baty, D., "Bispecific Antibodies for Cancer Therapy: The Light at the End of the Tunnel?," MAbs 1(6):539-547, Taylor & Francis, United States (Nov.-Dec. 2009).

Chatenoud, L., et al., "In Vivo Cell Activation Following OKT3 Administration. Systemic Cytokine Release and Modulation by Corticosteroids," Transplantation 49(4):697-702, Lippincott Williams & Wilkins, United States (Apr. 1990).

(56) References Cited

OTHER PUBLICATIONS

Chen, C.H., et al., "Dendritic-cell-associated C-type Lectin 2 (DCAL-2) Alters Dendritic-cell Maturation and Cytokine Production," Blood 107(4):1459-1467, American Society of Hematology, United States (Feb. 2006).

Chen, C.H., et al., "Effect of Duration of Osmotherapy on Blood-brain Barrier Disruption and Regional Cerebral Edema After Experimental Stroke," Journal of Cerebral Blood Flow and Metabolism 26(7):951-958, SAGE Publications, United States (Jul. 2006).

Coligan, J.E., et al., "Commonly Used Detergents," Current Protocols in Immunology Appendix 1:Appendix 1D, Associates and Wiley-Interscience, United States (May 2001).

Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).

Davies, J. and Riechmann, L., "Antibody VH Domains as Small Recognition Units," Biotechnology 13(5):475-479, Nature Publishing Group, United States (1995).

Davis, J.H., et al., "SEEDbodies: Fusion Proteins Based on Strand-exchange Engineered Domain (Seed) CH3 Heterodimers in an Fc Analogue Platform for Asymmetric Binders or Immunofusions and Bispecific Antibodies.," Protein Engineering, Design & Selection 23(4):195-202, Oxford University Press, England (2010).

De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, England (Apr. 1995).

De Kruif, J., et al., "Generation of Stable Cell Clones Expressing Mixtures of Human Antibodies," Biotechnology and Bioengineering 106(5):741-750, Wiley, United States (Aug. 2010).

De Vries, S.J., et al., "The HADDOCK Web Server for Data-driven Biomolecular Docking," Nature Protocols 5(5):883-897, Nature Publishing Group, England (May 2010).

De Wildt, et al., Analysis of Heavy and Light Chain Pairings Indicates that Receptor Editing Shapes fhe Human Antibody Repertoire, Journal of Molecular Biology, 285(3):895-901, Elsevier,England(1999).

Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).

Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007).

Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).

Dreier, T., et al., "Extremely Potent, Rapid and Costimulation-Independent Cytotoxic T-Cell Response against Lymphoma Cells Catalyzed by a Single-Chain Bispecific Antibody," International Journal of Cancer 100(6):690-697, Wiley-Liss, United States (2002).

Ellerson, J.R., et al., "Structure and Function of Immunoglobulin Domains. III. Isolation and Characterization of a Fragment Corresponding to the Cgamma2 Homology Region of Human Immunoglobin G1," Journal of Immunology 116(2):510-517, American Association of Immunologists, United States (Feb. 1976).

Farnan, D. and Moreno, G.T., "Multiproduct High-resolution Monoclonal Antibody Charge Variant Separations by pH Gradient Ion-exchange Chromatography," Analytical Chemistry 81(21):8846-8857, American Chemical Society, United States (2009).

Fraser, J.K., et al., "Cord Blood Transplantation Study (COBLT): Cord Blood Bank Standard Operating Procedures," Journal of Hematotherapy 7(6):521-561, Mary Ann Liebert, Inc., United States (Dec. 1998).

Geginat, J., et al., "Proliferation and Differentiation Potential of Human CD8+ Memory T-cell Subsets in Response to Antigen or Homeostatic Cytokines," Blood 101(11):4260-4266, American Society of Hematology, United States (Jun. 2003).

Genbank, "*Homo Sapiens* C-type Lectin Protein CLL-1 mRNA, Complete Cds," Accession No. AF247788.1, accessed at https://www.ncbi.nlm.nih.gov/nuccore/19716160/, Mar. 26, 2002,1 page.

Genbank, "*Homo Sapiens* Dendritic Cell Associated Lectin 2 mRNA, Complete Cds," Accession No. AY426759.1, accessed at https://www.ncbi.nlm.nih.gov/nuccore/40362523/, Feb. 9, 2006, 2 pages.

Genbank, "RecName: Full=C-type lectin domain family 12 member A; AltName: Full=C-type lectin-like molecule 1; Short=CLL-1; AltName: Full=Dendritic cell-associated lectin 2; Short=DCAL-2; AltName: Full=Myeloid inhibitory C-type lectin-like receptor; Short=MICL," Accession No. Q5QGZ9.3, accessed at https://www.ncbi.nlm.nih.gov/protein/Q5QGZ9, Mar. 28, 2018.

Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).

Gussow, D. and Seemann, G., "Humanization of Monoclonal Antibodies," Methods in Enzymology 203:99-121, Elsevier Science, United States (1991).

Haagen, I.A., et al., "The Efficacy of CD3×CD19 Bispecific Monoclonal Antibody (BsAB) in a Clonogenic Assay: The Effect of Repeated Addition of Bsab and Interleukin-2," Blood 85(11):3208-3212, American Society of Hematology, United States (Jun. 1995).

Han, Y., et al., "KLRL1, a Novel Killer Cell Lectinlike Receptor, Inhibits Natural Killer Cell Cytotoxicity," Blood 104(9):2856-2866, American Society of Hematology, United States (Nov. 2004).

Hendsch, Z.S., et al., "Preferential Heterodimer Formation via Undercompensated Electrostatic Interactions," Journal of the American Chemical Society 123(6):1264-1265, American Chemical Society, United States (Feb. 2001).

Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).

IMGT scientific chart, pp. 1-5, 2016.

Ionescu, R.M., et al., "Contribution of Variable Domains to the Stability of Humanized IgG1 Monoclonal Antibodies," Journal of Pharmaceutical Sciences 97(4):1414-1426, Elsevier, United States (Apr. 2008).

Kabat, E.A., et al., "Identical V Region Amino Acid Sequences and Segments of Sequences in Antibodies of Different Specificities. Relative Contributions of Vh and Vl Genes, Minigenes, and Complementarity-determining Regions to Binding of Antibody-combining Sites," Journal of Immunology 147(5):1709-1719, American Association of Immunologists, United States (Sep. 1991).

Kipriyanov, S.M., et al., "Bispecific CD3×CD19 Diabody for T Cell-Mediated Lysis of Malignant Human B Cells," International Journal of Cancer 77(5):763-772, Wiley-Liss, United States (1998).

Klein, C., et al., "Progress in Overcoming the Chain Association Issue in Bispecific Heterodimeric IgG Antibodies," MAbs 4(6):653-663, Taylor & Francis, United States (Nov.-Dec. 2012).

Kontermann, R.E., "Dual Targeting Strategies with Bispecific Antibodies," mAbs 4(2):182-197, Taylor and Francis, United States (2012).

Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).

Kumar, R., et al., "The Second Pdz Domain of Inad Is a Type I Domain Involved in Binding to Eye Protein Kinase C. Mutational Analysis and Naturally Occurring Variants," Journal of Biological Chemistry 276(27):24971-24977, American Society for Biochemistry and Molecular Biology, United States (Jul. 2001).

Lakowicz, J.R., "Principles of Fluorescence Spectroscopy," 3rd Edition, Kluwer Academic/Plenum Publisher, 469 pages (2006).

Lanzavecchia, A. and Scheidegger, D "The Use of Hybrid Hybridomas to Target Human Cytotoxic T Lymphocytes," European Journal of Immunology 17(1):105-111, Wiley-VCH, Germany (Jan. 1987).

(56) References Cited

OTHER PUBLICATIONS

Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).
Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, England (Apr. 2004).
Lee, B., et al., "The Interpretation of Protein Structures: Estimation of Static Accessibility," Journal of Molecular Biology 55(3):379-400, Elsevier, England (Feb. 1971).
Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).
Liu, H., et al., "Heterogeneity of Monoclonal Antibodies," Journal of Pharmaceutical Sciences 97(7):2426-2447, Wiley-Liss, United States (Jul. 2008).
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).
Loffler, A., et al., "A Recombinant Bispecific Single-chain Antibody, CD19×CD3, Induces Rapid and High Lymphoma-directed Cytotoxicity by Unstimulated T Lymphocytes," Blood 95(6):2098-2103, American Society of Hematology, United States (Mar. 2000).
Mariuzza, R.A., et al., "The Structural Basis of Antigen-antibody Recognition," Annual Review of Biophysics and Biomolecular Structure 16:139-159, Annual Reviews, United States (1987).
Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).
Marvin, J.S. and Zhu, Z., "Recombinant Approaches to IgG-like Bispecific Antibodies," Acta Pharmacologica Sinica 26(6):649-658, Nature Publishing Group, United States (2005).
Marvin, U.S., et al., "Redesigning an Antibody Fragment for Faster Association With Its Antigen," Biochemistry 42(23):7077-7083, American Chemical Society, United States (Jun. 2003).
McPhee, F., et al., "Engineering Human Immunodeficiency Virus 1 Protease Heterodimers as Macromolecular Inhibitors of Viral Maturation," Proceedings of the National Academy of Sciences of the United States of America 93(21):11477-11481, National Academy of Sciences, United States (Oct. 1996).
Merchant, A.M., et al., "An Efficient Route to Human Bispecific IgG," Nature Biotechnology 16(7):677-681, Nature Publishing Group, United States (1998).
Merus, www.merus.nl, press release, 2 pages, dated Jan. 7, 2013.
Merus, www.merus.nl, press release, 3 pages, dated Jun. 17, 2013.
Miller, S, "Protein-protein Recognition and the Association of Immunoglobulin Constant Domains," Journal of Molecular Biology 216(4):965-973, Elsevier Ltd (Dec. 1990).
Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).
Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).
Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, England (Apr. 1997).
Nissim, A., et al., "Antibody Fragments From a 'single Pot' Phage Display Library as Immunochemical Reagents," The EMBO Journal, 13(3):692-698, (Feb. 1994).
Nohaile, M.J., et al., "Altering dimerization specificity by changes in surface electrostatics," Proceedings of the National Academy of Sciences 98(6):3109-3114, National Academy of Sciences, United States (2001).
Noordhuis, P., et al., "Targeting of CLEC12A in Acute Myeloid Leukemia by Antibody-Drug-Conjugates and Bispecific CLL-1×CD3 BiTE Antibody," Blood 116(2890):6 pages, American Society of Hematology, United States (2010).
Norde, W.J., et al., "Myeloid Leukemic Progenitor Cells Can Be Specifically Targeted by Minor Histocompatibility Antigen LRH-1-reactive Cytotoxic T Cells," Blood 113(10):2312-2323, American Society of Hematology, United States (Mar. 2009 ).
Tahallah, N., et al., "The Effect of the Source Pressure on the Abundance of Ions of Noncovalent Protein Assemblies in an Electrospray Ionization Orthogonal Time-of-flight Instrument," Rapid Communications in Mass Spectrometry 15(8):596-601, John Wiley And Sons Ltd, England (2001).
Thom, G., et al., "Probing a Protein-Protein Interaction by In Vitro Evolution," Proceedings of the National Academy of Sciences 103(20):7619-7624, National Academy of Sciences, United States (May 2006).
Vajdos, F.F., et al., "Comprehensive Functional Maps of the Antigen-binding Site of an Anti-Erbb2 Antibody Obtained with Shotgun Scanning Mutagenesis," Journal of Molecular Biology 320(2):415-428, Academic Press, England (Jul. 2002).
Van Rhenen, A., et al., "The Novel AML Stem Cell Associated Antigen CII-1 Aids in Discrimination Between Normal and Leukemic Stem Cells," Blood 110(7):2659-2666, American Society of Hematology, United States (Oct. 2007).
Zeidler, R., et al., "Simultaneous Activation of T Cells and Accessory Cells by a New Class of Intact Bispecific Antibody Results in Efficient Tumor Cell Killing," Journal of Immunology 163(3):1246-1252, American Association of Immunologists, United States (1999).
Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).
Zhu, Z., et al., "Remodeling Domain Interfaces to Enhance Heterodimer Formation," Protein science 6(4):781-788, Cold Spring Harbor Laboratory Press, United States (Apr. 1997).
Office Action dated May 10, 2017, in U.S. Appl. No. 15/205,629, Bakker, A.B.H., et al., filed Jul. 8, 2016.
Office Action dated Nov. 1, 2016, in U.S. Appl. No. 15/205,629, Bakker, A.B.H., et al., filed Jul. 8, 2016.
Staerz, U.D., and Bevan, M.J., "Hybrid Hybridoma Producing a Bispecific Monoclonal Antibody that can Focus Effector T-cell Activity," Proceedings of the National Academy of Sciences USA 83(5):1453-1457, National Academy of Sciences, United States (1986).
Office Action dated Oct. 27, 2017, in U.S. Appl. No. 15/205,629, Bakker, A.B.H., et al., filed Jul. 8, 2016.
Strelkauskas et al., Human Monoclonal Antibody: 2. Simultaneous Expression of IgG and IgM with Similar Binding Specificities by a Human Hybrid Clone, Hybridoma, 1987, pp. 479-487, vol. 6, No. 5, Mary Ann Liebert Inc., Publishers.
Strop, P., et al., "Generating Bispecific Human IgG1 and IgG2 Antibodies from Any Antibody Pair," Journal of Molecular Biology 420(3):240-219, Academic Press, England (Jul. 2012).
Suntharalingam, G., et al., "Cytokine Storm in a Phase 1 Trial of the Anti-CD28 Monoclonal Antibody TGN1412," The New England Journal of Medicine 355(10):1018-1028, Massachusetts Medical Society, United States (Sep. 2006).
UniProt Entry Q5QGZ9, UniProt, retrieved Jan. 21, 2015, from <http://www.uniprot.org/unirptoIQ5QGZ9>.
Offner, S., et al., "Induction of Regular Cytolytic T Cell Synapses by Bispecific Single-chain Antibody Constructs on MHC Class I-negative Tumor Cells," Molecular Immunology 43(6):763-771, Pergamon Press, England (Feb. 2006).
Oganesyan, V., et al., "Structural Characterization of a Human Fc Fragment Engineered for Lack of Effector Functions," Acta Crystal-

(56) References Cited

OTHER PUBLICATIONS lographica. Section D, Biological Crystallography 64(Pt 6):700-704, Wiley-Blackwell, United States (Jun. 2008).
Padlan, E.A, "X-Ray Crystallography of Antibodies," Advances in Protein Chemistry 49:57-133, Academic Press, United States (1996).
Pantazes, R.J. and Maranas, C.D., "OptCDR: A General Computational Method for the Design of Antibody Complementarity Determining Regions for Targeted Epitope Binding," Protein Engineering, Design & Selection 23(11):849-858, Oxford University Press, England (Nov. 2010).
Papadea, C., et al., "Human Immunoglobulin G and Immunoglobulin G Subclasses: Biochemical, Genetic, and Clinical Aspects," Critical Reviews in Clinical Laboratory Sciences 27(1):27-58, Informa Healthcare, England (1989).
Peled, J.U., et al., "The Biochemistry of Somatic Hypermutation," Annual Review of Immunology 26:481-511, Annual Reviews Inc., United States (2008).
Ponsel, D. et al., "High affinity, developability and functional size: the holy grail of combinatorial antibody library jeneration," Molecules, vol. 16(5):3675-3700 (2011).
Raffen, R., et al., "Reengineering Immunoglobulin Domain Interactions by Introduction of Charged Residues," Protein Engineering 11(4):303-309, Oxford University Press, England (Apr. 1998).
Reusch, U., et al., "Beyond mAbs with TandAbs," Innovations in Pharmaceutical Technology, 4 pages, (2011).
Ridgway, J.B., et al., "'Knobs-lnto-Holes' Engineering of Antibody CH3 Domains for Heavy Chain Heterodimerization," Protein Engineering 9(7):617-621, Oxford University Press, England (1996).
Sali, A., et al., "Comparative Protein Modelling by Satisfaction of Spatial Restraints," Journal of Molecular Biology 234(3):779-815, Elsevier, England (Dec. 1993).
Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).
Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).
Schiffer, M., et al., "Analysis of Immunoglobulin Domain Interactions. Evidence for a Dominant Role of Salt Bridges," Journal of Molecular Biology 203(3):799-802, Elsevier, England (Oct. 1988).
Selzer, T., et al., "Rational Design of Faster Associating and Tighter Binding Protein Complexes," Nature Structural & Molecular Biology 7(7):537-541, Nature Publishing Group, United States (Jul. 2000).

Sheinerman, F.B., et al., "Electrostatic Aspects of Protein-protein Interactions," Current Opinion in Structural Biology 10(2):153-159, Elsevier Science, England (Apr. 2000).
Sheridan, C., "Amgen Swallows Micromet to BiTE Into All Market," Nature Biotechnology 30(4):300-301, Nature America Publishing, United States (Apr. 2012).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).
Sinha, N., et al., "Electrostatics in Protein Binding and Function," Current Protein and Peptide Science 3(6):601-614, Bentham Science Publishers, Netherlands (Dec. 2002).
Sircar, A., et al., "Rosettaantibody: Antibody Variable Region Homology Modeling Server," Nucleic Acids Research 37:W474-W479, Oxford University Press, England (Jul. 2009).
Sluijter, B.J., et al., "4-1BB-mediated Expansion Affords Superior Detection of in Vivo Primed Effector Memory CD8+ T Cells from Melanoma Sentinel Lymph Nodes," Clinical Immunology 137(2):221-233, Academic Press, United States (Nov. 2010).
Spiess, C., et al., "Alternative Molecular Formats and Therapeutic Applications for Bispecific Antibodies," Molecular Immunology 67(2 Pt A):95-106, Pergamon Press, England (Oct. 2015).
Blarcom., T.V., et al., "Productive Common Light Chain Libraries Yield Diverse Panels of High Affinity Bispecific Antibodies," MAbs 10(2):256-268, Taylor & Francis, United States (Feb. 2018).
Hall., B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (Sep. 1992).
Janeway, C.A., et al., "The generation of diversity in immunoglobulins," Immunobiology: The Immune System in Health and Disease, $5^{th}$ edition, 1-15, Garland Science, United States (2001).
Rabia., L.A., et al., "Understanding and Overcoming Trade-offs Between Antibody Affinity, Specificity, Stability and Solubility," Biochemical Engineering Journal 137:365-374, Elsevier, Netherlands (Sep. 2018).
Rudikoff., S., et al., "Single Amino Acid Substitution Altering Antigen-binding Specificity," Proc Natl Acad Sci USA 79(6):1979-1983, National Academy of Sciences, United States (Mar. 1982).
Townsend, C.L., et al., "Significant Differences in Physicochemical Properties of Human Immunoglobulin Kappa and Lambda CDR3 Regions," Front. Immunol. 7(388):1-12, Frontiers, United States (2016).

Figure 6

```
                    1                                                50
   3-33_VH     (1)  QVQLVESGGGVVQPGRSLRLSCAASGFTFSSYGMHWVRQAPGKGLEWVAV
   MF3056_VH   (1)  QVQLVQSGGGVVQPGRSLRLSCVASGFTFSSYGMHWVRQAPGKGLEWVAA
   Consensus   (1)  QVQLV SGGGVVQPGRSLRLSC ASGFTFSSYGMHWVRQAPGKGLEWVA
                    51                                               100
   3-33_VH    (51)  IWYDGSNKYYADSVKGRFTISRDNSKNTLYLQMNSLRAEDTAVYYCAR--
   MF3056_VH  (51)  IWYNGRKQDYADSVKGRFTISRDNSKNTLYLQMNSLRAEDTAVYYCTRGT
   Consensus  (51)  IWY G   YADSVKGRFTISRDNSKNTLYLQMNSLRAEDTAVYYC R
                    101       115
   3-33_VH    (99)  ----------------   (SEQ ID NO: 25)
   MF3056_VH (101)  GYNWFDPWGQGTLVT    (1-115 of SEQ ID NO: 25)
   Consensus (101)                     (SEQ ID NO: 62)
```

Figure 7

```
                    1                                                50
   MF3056_VH   (1)  QVQLVQSGGGVVQPGRSLRLSCVASGFTFSSYGMHWVRQAPGKGLEWVAA
   MF3872_VH   (1)  QVQLVQSGGGVVQPGRSLRLSCVASGFTFSSYGMHWVRQAPGKGLEWVAA
   MF3873_VH   (1)  QVQLVQSGGGVVQPGRSLRLSCVASGFTFSSYGMHWVRQAPGKGLEWVAA
   MF3905_VH   (1)  QVQLVQSGGGVVQPGRSLRLSCVASGFTFSSYGMHWVRQAPGKGLEWVAA
                    51                                               100
   MF3056_VH  (51)  IWYNGRKQDYADSVKGRFTISRDNSKNTLYLQMNSLRAEDTAVYYCTRGT
   MF3872_VH  (51)  IWYSGRKQDYADSVKGRFTISRDNSKNTLYLQMNSLRAEDTAVYYCTRGT
   MF3873_VH  (51)  IWYQGRKQDYADSVKGRFTISRDNSKNTLYLQMNSLRAEDTAVYYCTRGT
   MF3905_VH  (51)  IWYGGRKQDYADSVKGRFTISRDNSKNTLYLQMNSLRAEDTAVYYCTRGT
                    101           118
   MF3056_VH (101)  GYNWFDPWGQGTLVTVSS    (SEQ ID NO: 24)
   MF3872_VH (101)  GYNWFDPWGQGTLVTVSS    (SEQ ID NO: 26)
   MF3873_VH (101)  GYNWFDPWGQGTLVTVSS    (SEQ ID NO: 27)
   MF3905_VH (101)  GYNWFDPWGQGTLVTVSS    (SEQ ID NO: 28)
```

Figure 8

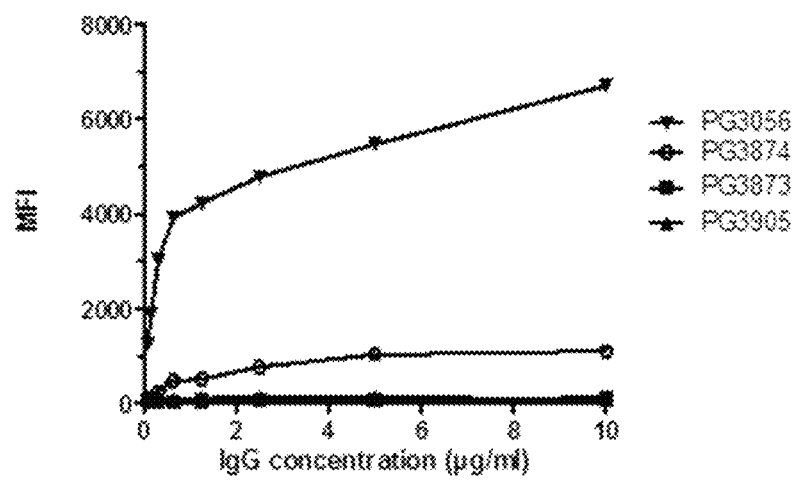

Figure 9

```
                    1                                                  50
MF3056_VH    (1)    QVQLVQSGGGVVQPGRSLRLSCVASGFTFSSYGMHWVRQAPGKGLEWVAA
MF3874_VH    (1)    QVQLVESGGGVVQPGRSLRLSCVASGFTFSSYGMHWVRQAPGKGLEWVAA
MF3878_VH    (1)    QVQLVQSGGGVVQPGRSLRLSCAASGFTFSSYGMHWVRQAPGKGLEWVAA
MF3883_VH    (1)    QVQLVQSGGGVVQPGRSLRLSCVASGFTFSSYGMHWVRQAPGKGLEWVAV
MF3886_VH    (1)    QVQLVQSGGGVVQPGRSLRLSCVASGFTFSSYGMHWVRQAPGKGLEWVAA
MF3891_VH    (1)    QVQLVESGGGVVQPGRSLRLSCAASGFTFSSYGMHWVRQAPGKGLEWVAA
Consensus    (1)    QVQLVQSGGGVVQPGRSLRLSCVASGFTFSSYGMHWVRQAPGKGLEWVAA
                    51                                                 100
MF3056_VH    (51)   IWYNGRKQDYADSVKGRFTISRDNSKNTLYLQMNSLRAEDTAVYYCTRGT
MF3874_VH    (51)   IWYNGRKQDYADSVKGRFTISRDNSKNTLYLQMNSLRAEDTAVYYCTRGT
MF3878_VH    (51)   IWYNGRKQDYADSVKGRFTISRDNSKNTLYLQMNSLRAEDTAVYYCTRGT
MF3883_VH    (51)   IWYNGRKQDYADSVKGRFTISRDNSKNTLYLQMNSLRAEDTAVYYCTRGT
MF3886_VH    (51)   IWYNGRKQDYADSVKGRFTISRDNSKNTLYLQMNSLRAEDTAVYYCARGT
MF3891_VH    (51)   IWYNGRKQDYADSVKGRFTISRDNSKNTLYLQMNSLRAEDTAVYYCARGT
Consensus    (51)   IWYNGRKQDYADSVKGRFTISRDNSKNTLYLQMNSLRAEDTAVYYCTRGT
                    101           118
MF3056_VH    (101)  GYNWFDPWGQGTLVTVSS   (SEQ ID NO: 24)
MF3874_VH    (101)  GYNWFDPWGQGTLVTVSS   (SEQ ID NO: 29)
MF3878_VH    (101)  GYNWFDPWGQGTLVTVSS   (SEQ ID NO: 30)
MF3883_VH    (101)  GYNWFDPWGQGTLVTVSS   (SEQ ID NO: 31)
MF3886_VH    (101)  GYNWFDPWGQGTLVTVSS   (SEQ ID NO: 32)
MF3891_VH    (101)  GYNWFDPWGQGTLVTVSS   (SEQ ID NO: 33)
Consensus    (101)  GYNWFDPWGQGTLVTVSS   (SEQ ID NO: 63)
```

Figure 12

```
                    1                                                50
MF3056_VH    (1)  QVQLVQSGGGVVQPGRSLRLSCVASGFTFSSYGMHWVRQAPGKGLEWVAA
MF5192_VH    (1)  QVQLVQSGGGVVQPGRSLRLSCVASGFTFSSYGMHWVRQAPGKGLEWVAA
MF5193_VH    (1)  QVQLVQSGGGVVQPGRSLRLSCVASGFTFSSYGMHWVRQAPGKGLEWVAA
MF5194_VH    (1)  QVQLVQSGGGVVQPGRSLRLSCVASGFTFSSYGMHWVRQAPGKGLEWVAA
MF5195_VH    (1)  QVQLVQSGGGVVQPGRSLRLSCVASGFTFSSYGMHWVRQAPGKGLEWVAA
MF5196_VH    (1)  QVQLVQSGGGVVQPGRSLRLSCVASGFTFSSYGMHWVRQAPGKGLEWVAA
MF5197_VH    (1)  QVQLVQSGGGVVQPGRSLRLSCVASGFTFSSYGMHWVRQAPGKGLEWVAA
Consensus    (1)  QVQLVQSGGGVVQPGRSLRLSCVASGFTFSSYGMHWVRQAPGKGLEWVAA
                    51                                              100
MF3056_VH   (51)  IWYNGRKQDYADSVKGRFTISRDNSKNTLYLQMNSLRAEDTAVYYCTRGT
MF5192_VH   (51)  IWYHGRKQDYADSVKGRFTISRDNSKNTLYLQMNSLRAEDTAVYYCTRGT
MF5193_VH   (51)  IWYHARKQDYADSVKGRFTISRDNSKNTLYLQMNSLRAEDTAVYYCTRGT
MF5194_VH   (51)  IWYHTRKQDYADSVKGRFTISRDNSKNTLYLQMNSLRAEDTAVYYCTRGT
MF5195_VH   (51)  IWYHNRKQDYADSVKGRFTISRDNSKNTLYLQMNSLRAEDTAVYYCTRGT
MF5196_VH   (51)  IWYNARKQDYADSVKGRFTISRDNSKNTLYLQMNSLRAEDTAVYYCTRGT
MF5197_VH   (51)  IWYNTRKQDYADSVKGRFTISRDNSKNTLYLQMNSLRAEDTAVYYCTRGT
Consensus   (51)  IWYHARKQDYADSVKGRFTISRDNSKNTLYLQMNSLRAEDTAVYYCTRGT
                    101          118
MF3056_VH  (101)  GYNWFDPWGQGTLVTVSS   (SEQ ID NO: 24)
MF5192_VH  (101)  GYNWFDPWGQGTLVTVSS   (SEQ ID NO: 34)
MF5193_VH  (101)  GYNWFDPWGQGTLVTVSS   (SEQ ID NO: 35)
MF5194_VH  (101)  GYNWFDPWGQGTLVTVSS   (SEQ ID NO: 36)
MF5195_VH  (101)  GYNWFDPWGQGTLVTVSS   (SEQ ID NO: 37)
MF5196_VH  (101)  GYNWFDPWGQGTLVTVSS   (SEQ ID NO: 38)
MF5197_VH  (101)  GYNWFDPWGQGTLVTVSS   (SEQ ID NO: 39)
Consensus  (101)  GYNWFDPWGQGTLVTVSS   (SEQ ID NO: 64)
```

Figure 13

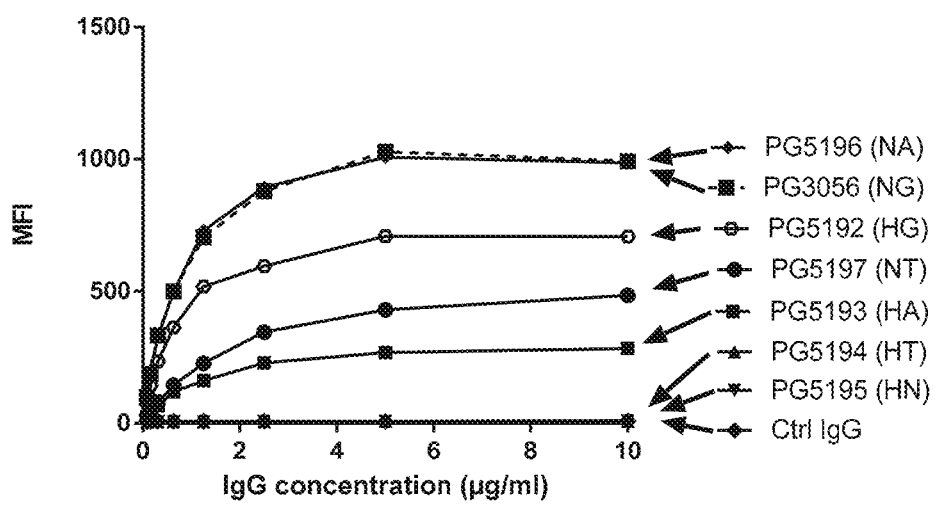

Figure 18
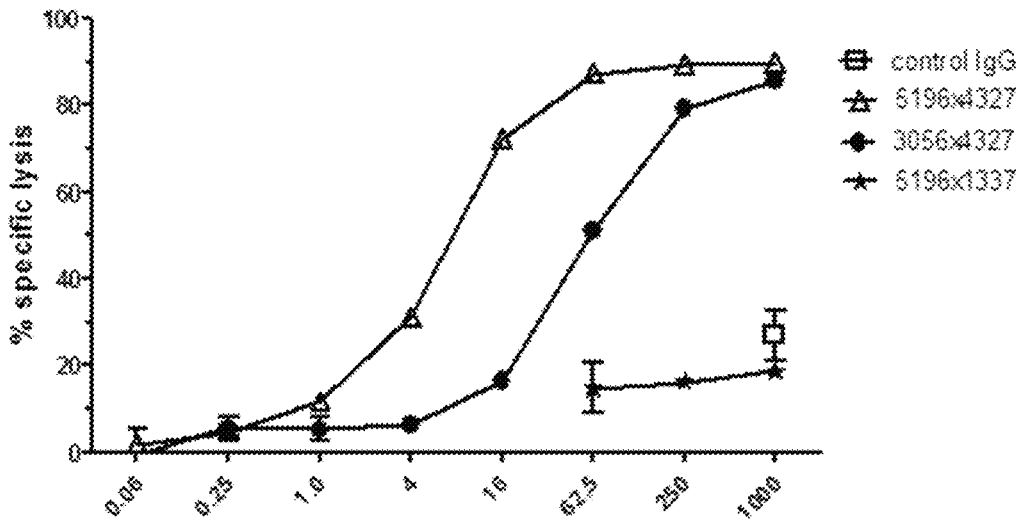
Figure 19
A)
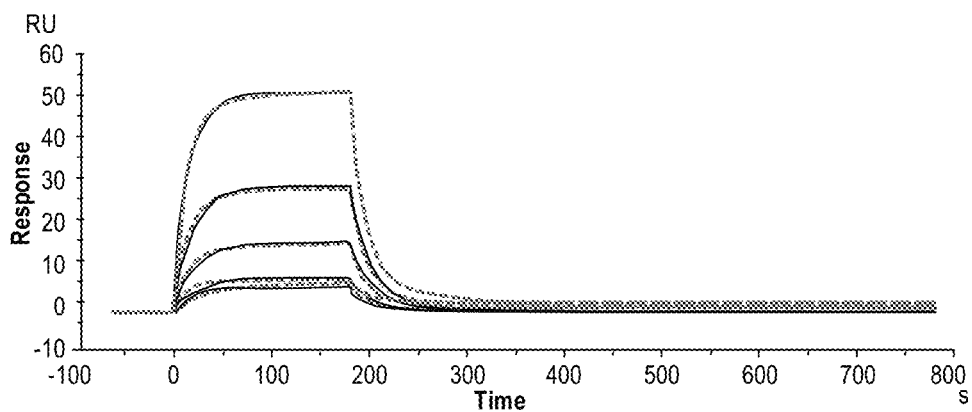
B)
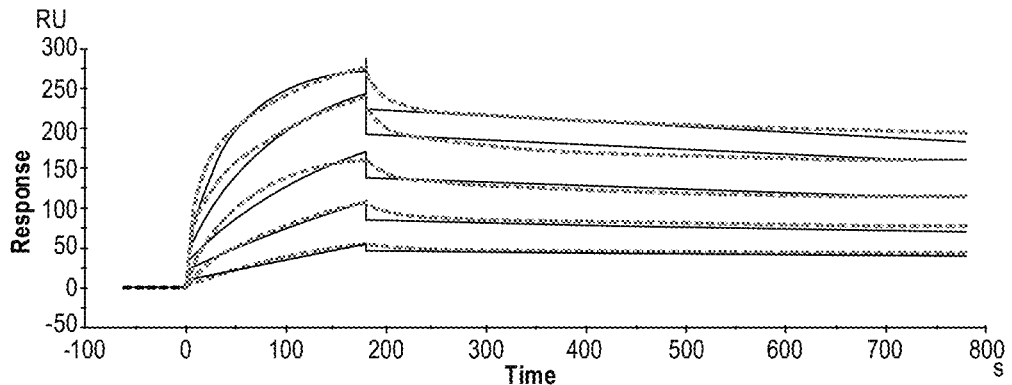

| Sample | Tm1 (°C) | Tm2 (°C) |
|---|---|---|
| WT | WT | 70.9 | 85.0 |
| DM | WT | 73.5 | 85.0 |

Figure 22

15C3 VH (MF3055_VH)  (SEQ ID NO: 40)
QVQLVQSGGGVVQPGRSLRLSCVASGFTFSSYGMHWVRQAPGKGLEWVAAIWYNGRKQDYADSV
KGRFTISRDNSKNTLYLQMNSLRAEDTAVYYCTRGTGYNWFDPWGQGTLVTVSS

15C3 VL1 - IGKV3-11*  (SEQ ID NO: 41)
EIVLTQSPATLSLSPGERATLSCRASQSVSSYLAWYQQKPGQAPRLLIYDASNRATGIPASFSG
SGSGTDFTLTISSLEPEDFAVYYCQQRSNWPWTFGQGTKVEIK

15C3 VL2 - IGKV1-13 (MF3055_VL)  (SEQ ID NO: 42)
AIQLTQSPSSLSASVGDRVTITCRASQGISSALAWYQQKPGKAPKLLIYDASSLESGVPSRFSG
SGSGTDFTLTISSLQPEDFATYYCQQFNSYPITFGQGTRLEIK

IGKV1-39 (MF3056_VL)  (SEQ ID NO: 43)
DIQMTQSPSSLSASVGDRVTITCRASQSISSYLNWYQQKPGKAPKLLIYAASSLQSGVPSRFSG
SGSGTDFTLTISSLQPEDFATYYCQQSYSTPPTFGQGTKVEIK

Figure 23

(A)
IGKV1-39A  (SEQ ID NO: 44)

DIQMTQSPSSLSASVGDRVTITCRASQSISSYLNWYQQKPGKAPKLLIYAASSLQSGVPSRFSG
SGSGTDFTLTISSLQPEDFATYYCQQSYSTP (B)
IGKV1-39/jk1  (SEQ ID NO: 45)
DIQMTQSPSSLSASVGDRVTITCRASQSISSYLNWYQQKPGKAPKLLIYAASSLQSGVPSRFSG
SGSGTDFTLTISSLQPEDFATYYCQQSYSTPPTFGQGTKVEIK (C)
IGKV1-39/jk5  (SEQ ID NO: 46)
DIQMTQSPSSLSASVGDRVTITCRASQSISSYLNWYQQKPGKAPKLLIYAASSLQSGVPSRFSG
SGSGTDFTLTISSLQPEDFATYYCQQSYSTPPITFGQGTRLEIK

Figure 24

MF1337_VH  (SEQ ID NO: 47)

EVQLVETGAEVKKPGASVKVSCKASDYIFTKYDINWVRQAPGQGLEWMGWMSANTGNTGYAQKFQGRVTM
TRDTSINTAYMELSSLTSGDTAVYFCARSSLFKTETAPYYHFALDVWGQGTTVTVSS

MF4327_VH  (SEQ ID NO: 48)

QVQLVQSGAEVKKPGASVKVSCKASGYTFTSYYMHWVRQAPGQGLEWMGIINPSGGSTSYAQKFQGRVTM
TRDTSTSTVYMELSSLRSEDTAVYYCAKGTTGDWFDYWGQGTLVTVSS

Figure 25

```
                    1                                                50
MF5196_VH     (1)   QVQLVQSGGGVVQPGRSLRLSCVASGFTFSSYGMHWVRQAPGKGLEWVAA
MF5603_VH     (1)   QVQLVQSGGGVVQPGRSLRLSCVASGFTFSSYGMHWVRQAPGKGLEWVAA
MF5616_VH     (1)   QVQLVQSGGGVVQPGRSLRLSCVASGFTFSSYGMHWVRQAPGKGLEWVAA
MF5626_VH     (1)   QVQLVQSGGGVVQPGRSLRLSCVASGFTFSSYGMHWVRQAPGKGLEWVAA
MF5630_VH     (1)   QVQLVQSGGGVVQPGRSLRLSCVASGFTFSSYGMHWVRQAPGKGLEWVAA
MF5648_VH     (1)   QVQLVQSGGGVVQPGRSLRLSCVASGFTFSSYGMHWVRQAPGKGLEWVAA
MF5661_VH     (1)   QVQLVQSGGGVVQPGRSLRLSCVASGFTFSSYGMHWVRQAPGKGLEWVAQ
MF5694_VH     (1)   QVQLVQSGGGVVQPGRSLRLSCVASGFTFSSYGMHWVRQAPGKGLEWVAA
Consensus     (1)   QVQLVQSGGGVVQPGRSLRLSCVASGFTFSSYGMHWVRQAPGKGLEWVAA
                    51                                               100
MF5196_VH    (51)   IWYNARKQDYADSVKGRFTISRDNSKNTLYLQMNSLRAEDTAVYYCTRGT
MF5603_VH    (51)   IWYNARKQEYIDSVKGRFTISRDNSKNTLYLQMNSLRAEDTAVYYCTRGT
MF5616_VH    (51)   IWYNARKQEYNDSVKGRFTISRDNSKNTLYLQMNSLRAEDTAVYYCTRGT
MF5626_VH    (51)   IWYNARKQEYRDSVKGRFTISRDNSKNTLYLQMNSLRAEDTAVYYCTRGT
MF5630_VH    (51)   IWYNARKQDYADSVKGRFTISRDNSKNTLYLQMNSLRAEDTAVYYCTRGT
MF5648_VH    (51)   IWYNARKQEYLDSVKGRFTISRDNSKNTLYLQMNSLRAEDTAVYYCTRGT
MF5661_VH    (51)   IWYNARKQEYSDSVKGRFTISRDNSKNTLYLQMNSLRAEDTAVYYCTRGT
MF5694_VH    (51)   IWYNARKQEYSDSVKGRFTISRDNSKNTLYLQMNSLRAEDTAVYYCTRGT
Consensus    (51)   IWYNARKQEYADSVKGRFTISRDNSKNTLYLQMNSLRAEDTAVYYCTRGT
                    101              118
MF5196_VH   (101)   GYNWFDPWGQGTLVTVSS   (SEQ ID NO: 38)
MF5603_VH   (101)   GYNWFDPWGQGTLVTVSS   (SEQ ID NO: 49)
MF5616_VH   (101)   GYNWFDPWGQGTLVTVSS   (SEQ ID NO: 50)
MF5626_VH   (101)   GYNWFDPWGQGTLVTVSS   (SEQ ID NO: 51)
MF5630_VH   (101)   GYNWYDPWGQGTLVTVSS   (SEQ ID NO: 52)
MF5648_VH   (101)   GYNWFDPWGQGTLVTVSS   (SEQ ID NO: 53)
MF5661_VH   (101)   GYNWFDPWGQGTLVTVSS   (SEQ ID NO: 54)
MF5694_VH   (101)   GYNWFDPWGQGTLVTVSS   (SEQ ID NO: 55)
Consensus   (101)   GYNWFDPWGQGTLVTVSS   (SEQ ID NO: 56)
```

MF5196_VH  (SEQ ID NO: 38)
QVQLVQSGGGVVQPGRSLRLSCVASGFTFSSYGMHWVRQAPGKGLEWVAAIWYNARKQDYADSVKGRFTI
SRDNSKNTLYLQMNSLRAEDTAVYYCTRGTGYNWFDPWGQGTLVTVSS

MF5603_VH  (SEQ ID NO: 49)
QVQLVQSGGGVVQPGRSLRLSCVASGFTFSSYGMHWVRQAPGKGLEWVAAIWYNARKQEYIDSVKGRFTI
SRDNSKNTLYLQMNSLRAEDTAVYYCTRGTGYNWFDPWGQGTLVTVSS

MF5616_VH  (SEQ ID NO: 50)
QVQLVQSGGGVVQPGRSLRLSCVASGFTFSSYGMHWVRQAPGKGLEWVAAIWYNARKQEYNDSVKGRFTI
SRDNSKNTLYLQMNSLRAEDTAVYYCTRGTGYNWFDPWGQGTLVTVSS

MF5626_VH  (SEQ ID NO: 51)
QVQLVQSGGGVVQPGRSLRLSCVASGFTFSSYGMHWVRQAPGKGLEWVAAIWYNARKQEYRDSVKGRFTI
SRDNSKNTLYLQMNSLRAEDTAVYYCTRGTGYNWFDPWGQGTLVTVSS

MF5630_VH  (SEQ ID NO: 52)
QVQLVQSGGGVVQPGRSLRLSCVASGFTFSSYGMHWVRQAPGKGLEWVAAIWYNARKQDYADSVKGRFTI
SRDNSKNTLYLQMNSLRAEDTAVYYCTRGTGYNWYDPWGQGTLVTVSS

MF5648_VH  (SEQ ID NO: 53)
QVQLVQSGGGVVQPGRSLRLSCVASGFTFSSYGMHWVRQAPGKGLEWVAAIWYNARKQEYLDSVKGRFTI
SRDNSKNTLYLQMNSLRAEDTAVYYCTRGTGYNWFDPWGQGTLVTVSS

Figure 25 (continued)

MF5661_VH  (SEQ ID NO: 54)
QVQLVQSGGGVVQPGRSLRLSCVASGFTFSSYGMHWVRQAPGKGLEWVAQIWYNARKQEYSDSVKGRFTI
SRDNSKNTLYLQMNSLRAEDTAVYYCTRGTGYNWFDPWGQGTLVTVSS

MF5694_VH  (SEQ ID NO: 55)
QVQLVQSGGGVVQPGRSLRLSCVASGFTFSSYGMHWVRQAPGKGLEWVAAIWYNARKQEYSDSVKGRFTI
SRDNSKNTLYLQMNSLRAEDTAVYYCTRGTGYNWFDPWGQGTLVTVSS

Figure 28

```
                1                                                50
MF5196     (1)  QVQLVQSGGGVVQPGRSLRLSCVASGFTFSSYGMHWVRQAPGKGLEWVAA
MF5351     (1)  QVQLVQSGGGVVQPGRSLRLSCAASGFTFSSYGMHWVRQAPGKGLEWVAM
MF5354     (1)  QVQLVQSGGGVVQPGRSLRLSCAASGFTFSGYGMHWVRQAPGKGLEWVAQ
MF5356     (1)  QVQLVESGGGVVQPGRSLRLSCAASGFTFSKYGMHWVRQAPGKGLEWVAQ
Consensus  (1)  QVQLVQSGGGVVQPGRSLRLSCAASGFTFSSYGMHWVRQAPGKGLEWVAQ
                51                                              100
MF5196    (51)  IWYNARKQDYADSVKGRFTISRDNSKNTLYLQMNSLRAEDTAVYYCTRGT
MF5351    (51)  IWYDGKNTYYADSVKGRFTISRDNSKNTLYLQMNSLRAEDTAVYYCTRGT
MF5354    (51)  IYYDGSRTYYADSVKGRFTISRDNSKNTLYLQMNSLRAEDTAVYYCTRGT
MF5356    (51)  IWHDGRKTYYADSVKGRFTISRDNSKNTLYLQMNSLRAEDTAVYYCTRGT
Consensus (51)  IWYDGRKTYYADSVKGRFTISRDNSKNTLYLQMNSLRAEDTAVYYCTRGT
                101        118
MF5196   (101)  GYNWFDPWGQGTLVTVSS   (SEQ ID NO: 38)
MF5351   (101)  GYNWFDPWGQGTLVTVSS   (SEQ ID NO: 57)
MF5354   (101)  GYNWFDPWGQGTLVTVSS   (SEQ ID NO: 58)
MF5356   (101)  GYNWFDPWGQGTLVTVSS   (SEQ ID NO: 59)
Consensus(101)  GYNWFDPWGQGTLVTVSS   (SEQ ID NO: 60)
```

MF5351_VH  (SEQ ID NO: 57)
QVQLVQSGGGVVQPGRSLRLSCAASGFTFSSYGMHWVRQAPGKGLEWVAMIWYDGKNTYYADSVKGRFTI
SRDNSKNTLYLQMNSLRAEDTAVYYCTRGTGYNWFDPWGQGTLVTVSS

MF5354_VH  (SEQ ID NO: 58)
QVQLVQSGGGVVQPGRSLRLSCAASGFTFSGYGMHWVRQAPGKGLEWVAQIYYDGSRTYYADSVKGRFTI
SRDNSKNTLYLQMNSLRAEDTAVYYCTRGTGYNWFDPWGQGTLVTVSS

MF5356_VH  (SEQ ID NO: 59)
QVQLVESGGGVVQPGRSLRLSCAASGFTFSKYGMHWVRQAPGKGLEWVAQIWHDGRKTYYADSVKGRFTI
SRDNSKNTLYLQMNSLRAEDTAVYYCTRGTGYNWFDPWGQGTLVTVSS

Figure 29
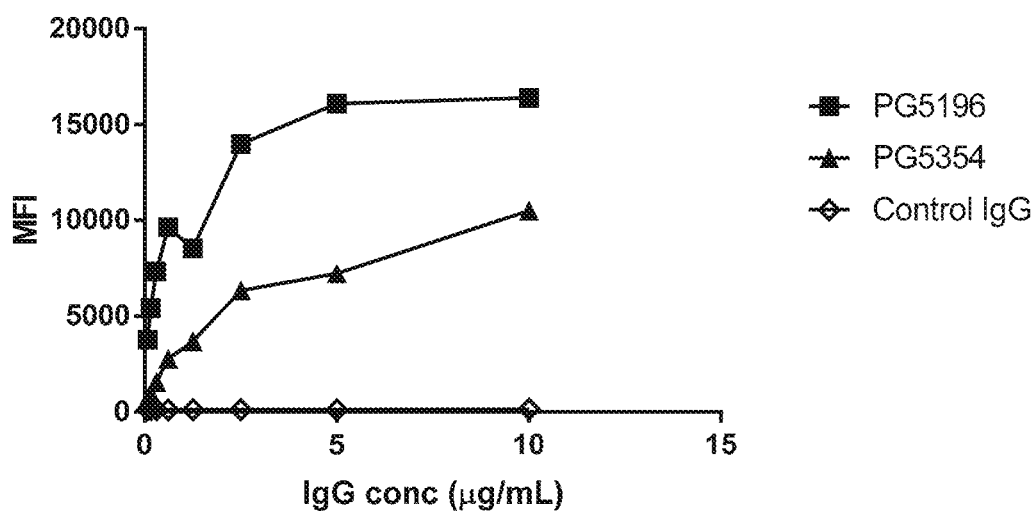
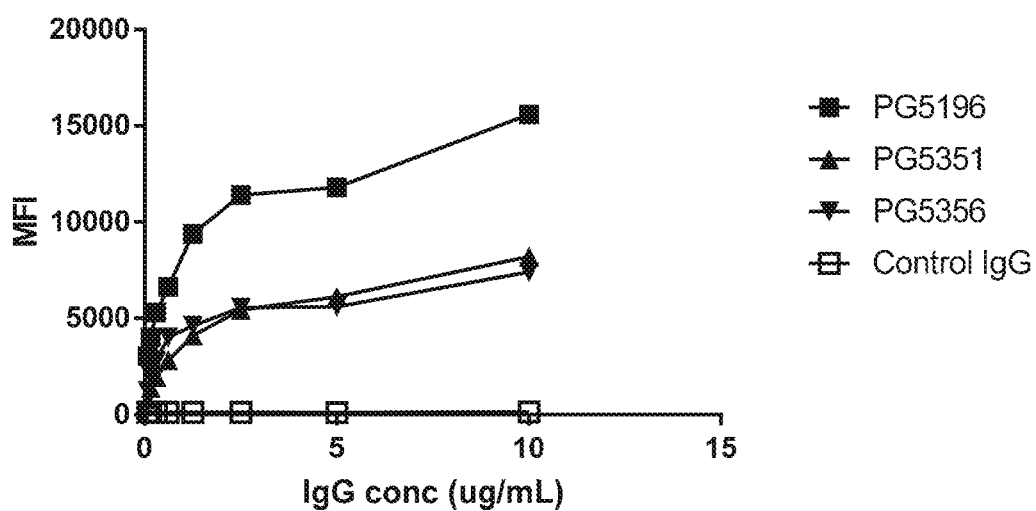

HUMAN CD3 BINDING ANTIBODY

CROSS-REFERENCE TO RELATED APPLICATIONS

This application is a divisional of U.S. patent application Ser. No. 15/888,757, filed Feb. 5, 2018; which is a divisional of U.S. patent application Ser. No. 15/205,629 filed Jul. 8, 2016; which claims priority to EP Application No. 15176355.4, filed Jul. 10, 2015, the contents of which are hereby incorporated by reference.

REFERENCE TO SEQUENCE LISTING SUBMITTED ELECTRONICALLY VIA EFS-WEB

The content of the electronically submitted sequence listing (Name: "4096_0080003_SL25_.txt"; Size: 60,358 bytes; Date of Creation: Jan. 11, 2018) submitted in this application is incorporated herein by reference in its entirety.

The invention relates to the field of antibodies, in particular to the field of therapeutic antibodies. The antibodies can be used in the treatment of humans. More in particular the invention relates to antibodies and preferably bispecific antibodies for the treatment of a tumor.

Monoclonal antibodies that bind to human CD3 were among the first antibodies developed for therapeutic use in humans. Monoclonal CD3 binding antibodies are typically used for their immune suppressive qualities, for instance in transplant rejection. Antibodies which are bispecific for CD3 on T cells and for a surface target antigen on cancer cells, are capable of connecting any kind of T cell to a cancer cell, independently of T-cell receptor specificity, costimulation, or peptide antigen presentation. Such bispecific T-cell engaging antibodies show great promise in the treatment of various cancers and neoplastic growths.

WO2014/051433 (incorporated herein by reference) describes CD3 mAbs that are suitable candidates to serve as building block in the generation of bispecific antibodies that act as T-cell engager molecules. These CD3 mAbs are designated 3056 and 3896; the VH and VL sequences of these mAbs are disclosed in FIG. 22. Both the 3056 and 3896 CD3 mAbs have good properties in terms of functional activity. They bind to cell surface expressed CD3/TCR on human T cell lines with an affinity (KD) that is significantly less than the affinity of the well-known mouse anti-CD3 antibody mOKT3, resulting in a lower mean fluorescence intensity in flow cytometric analysis on $CD3^{POS}$ cells. Similarly, when immobilized on tissue culture plates, they induce T cell proliferation to a lesser extent when compared to mOKT3.

Without being bound by theory it is believed that a CD3 affinity that is significantly less than the affinity of mOKT3 is preferred in a bispecific T-cell engager format. It is preferred that the bispecific antibody binds to CD3 with an affinity that is less than the affinity of binding to the tumor antigen. Without being bound to theory it is believed that this difference in affinity permits preferential opsonization of the tumor cells by the bispecific antibody, thereby labelling them for destruction by immune effector cells including NK and/or T cells present in the vicinity.

The inventors observed that results obtained with the 3056 antibody exhibited batch to batch variation. This surprised the inventors as the variability was not an issue with the antibody 15C3, which has the same VH-sequence as antibody 3056 but a different light chain (described in WO2005/118635).

It is an object of the invention to provide a variant of antibody 3056 with essentially the same CD3 binding properties in kind, not necessarily in amount, with improved characteristics.

SUMMARY OF THE INVENTION

The invention provides an antibody that binds human CD3 which antibody comprises a heavy chain and light chain wherein said heavy chain comprises a variable region that comprises an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein
 $X_1$=N and $X_2$=A;
 $X_1$=N and $X_2$=T;
 $X_1$=S and $X_2$=G;
 $X_1$=H and $X_2$=G;
 $X_1$=D and $X_2$=G; or
 $X_1$=H and $X_2$=A.

The invention further provides a nucleic acid molecule that encodes an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein
 $X_1$=N and $X_2$=A;
 $X_1$=N and $X_2$=T;
 $X_1$=S and $X_2$=G;
 $X_1$=H and $X_2$=G;
 $X_1$=D and $X_2$=G; or
 $X_1$=H and $X_2$=A.

The combination $X_1$ and $X_2$ in an antibody as described herein is preferably $X_1$=N and $X_2$=A.

The invention further provides a cell that expresses the antibody and/or comprises the nucleic acid molecule.

An antibody of the invention is, unless otherwise specifically specified, preferably a bispecific antibody. The bispecific antibody preferably binds at least human CD3. In addition, the bispecific antibody preferably binds at least a surface molecule that is preferentially expressed on human tumor cells. In a preferred embodiment, the bispecific antibody binds to BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, or PSMA. In a more preferred embodiment, the bispecific antibody binds to CLEC12A.

The invention further provides a pharmaceutical composition comprising an antibody according to the invention.

Further provided is an antibody according to the invention that further comprises a label, preferably a label for in vivo imaging.

The invention also provides a method for the treatment of a subject having a tumor or at risk of having a tumor comprising administering to the subject a bispecific antibody according to the invention. Also provided is a bispecific antibody according to the invention for use in the treatment of a subject having a tumor or at risk of a tumor. Further provided is the use of an antibody of the invention for the preparation of a medicament for the treatment of a subject having a tumor or at risk of a tumor. In a preferred embodiment the tumor is a CLEC12A positive tumor.

DETAILED DESCRIPTION OF THE INVENTION

An antibody of the invention is preferably a bispecific antibody. The bispecific antibody preferably binds at least human CD3. In addition, the bispecific antibody preferably binds at least a surface molecule that is expressed on human tumor cells. In a preferred embodiment the bispecific antibody binds to BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, or PSMA. In a particularly preferred embodiment, the bispecific antibody binds to CLEC12A.

BCMA is also referred to as Tumor Necrosis Factor Receptor Superfamily, Member 17 (TNFRSF17); TNFRSF13A2; B Cell Maturation Antigen; BCM; B-Cell Maturation Factor; B-Cell Maturation Protein; CD269 or CD269 Antigen. Ids: HGNC: 11913; Entrez Gene: 608; Ensembl: ENSG00000048462; OMIM: 109545; UniProtKB: Q02223.

CD19 is also referred to as CD19 Molecule; T-Cell Surface Antigen Leu-12; CD19 Antigen; CVID3; Differentiation Antigen CD19; B4; B-Lymphocyte Surface Antigen B4; B-Lymphocyte Antigen CD19. Ids: HGNC: 1633; Entrez Gene: 930; Ensembl: ENSG00000177455; OMIM: 107265; UniProtKB: P15391.

CD20 is also referred to as Membrane-Spanning 4-Domains, Subfamily A, Member 1 (MS4A1); MS4A2; CD20; S7; Leukocyte Surface Antigen Leu-16; B-Lymphocyte Antigen CD20; Bp35; B-Lymphocyte Cell-Surface Antigen B1; CD20 Antigen; CD20 Receptor; CVID5; B-Lymphocyte Surface Antigen B1; B1; Membrane-Spanning 4-Domains Subfamily A Member 1; LEU-16. Ids: HGNC: 7315; Entrez Gene: 931; Ensembl: ENSG00000156738; OMIM: 112210; UniProtKB: P11836.

CD30 is also referred to as Tumor Necrosis Factor Receptor Superfamily, Member 8 (TNFRSF8); Ki-1 Antigen; CD30; Ki-1; D1S166E; Cytokine Receptor CD30; Lymphocyte Activation Antigen CD30; Tumor Necrosis Factor Receptor Superfamily Member 8; CD30L Receptor; CD30 Antigen. Ids: HGNC: 11923; Entrez Gene: 943; Ensembl: ENSG00000120949; OMIM: 153243; UniProtKB: P28908.

CD33 is also referred to as CD33 Molecule; SIGLEC-3; CD33 Antigen (Gp67); Myeloid Cell Surface Antigen CD33; Sialic Acid Binding Ig-Like Lectin 3; Siglec-3; SIGLEC3; CD33 Antigen and gp67. Ids: HGNC: 1659; Entrez Gene: 945; Ensembl: ENSG00000105383; OMIM: 159590; UniProtKB: P20138.

CD38 is also referred to as CD38 Molecule; T10; CD38 Antigen (P45); CADPr Hydrolase 1; ADP-Ribosyl Cyclase 1; ADP-Ribosyl Cyclase/Cyclic ADP-Ribose Hydrolase; NAD(+) Nucleosidase; EC 3.2.2.5; Cyclic ADP-Ribose Hydrolase 1; CD38 Antigen. Ids: HGNC: 1667; Entrez Gene: 952; Ensembl: ENSG00000004468; OMIM: 107270; UniProtKB: P28907.

CD44 is also referred to as CD44 Molecule (Indian Blood Group); IN; MDU2; CD44 Antigen (Homing Function And Indian Blood Group System); MDU3; CDW44; MIC4; CSPG8; Chondroitin Sulfate Proteoglycan 8; HCELL; Hematopoietic Cell E- And L-Selectin Ligand; MC56; Extracellular Matrix Receptor III; Pgp1; Heparan Sulfate Proteoglycan; Cell Surface Glycoprotein CD44; Hyaluronate Receptor; epican; Phagocytic Glycoprotein 1; Homing Function And Indian Blood Group System; ECMR-III; CDw44; HUTCH-I; Epican; LHR; PGP-1; CD44 Antigen; PGP-I; CP90 Lymphocyte Homing/Adhesion Receptor; Phagocytic Glycoprotein I; Hermes Antigen. Ids: HGNC: 1681; Entrez Gene: 960; Ensembl: ENSG00000026508; OMIM: 107269; UniProtKB: P16070.

CD123 is also referred to as Cell Division Cycle 123; Cell Division Cycle 123 Homolog; C10orf7; Cell Division Cycle Protein 123 Homolog; D123; Protein D123; HT-1080; CCEP123; PZ32; CEP89; Cell Division Cycle 123 Homolog (S. cerevisiae); FLJ14640; Chromosome 10 Open Reading Frame 7. Ids: HGNC: 16827; Entrez Gene: 8872; Ensembl: ENSG00000151465; OMIM: 615470; UniProtKB: O75794.

CD138 is also referred to as Syndecan 1 (SCD1); CD138; SDC; Heparan Sulfate Proteoglycan Fibroblast Growth Factor Receptor; Syndecan Proteoglycan 1; syndecan; SYND1; syndecan-1; CD138 Antigen. Ids: HGNC: 10658; Entrez Gene: 6382; Ensembl: ENSG00000115884; OMIM: 186355; UniProtKB: P18827.

CEA is also referred to as Carcinoembryonic Antigen-Related Cell Adhesion Molecule 5 (CEACAM5); Meconium Antigen 100; CD66e; Carcinoembryonic Antigen; CD66e Antigen. Ids: HGNC: 1817; Entrez Gene: 1048; Ensembl: ENSG00000105388; OMIM: 114890; UniProtKB: P06731. CLEC12A is also referred to as C-Type Lectin Domain Family 12, Member A; C-Type Lectin Protein CLL-1; MICL; Dendritic Cell-Associated Lectin 2; C-Type Lectin Superfamily; Myeloid Inhibitory C-Type Lectin-Like Receptor; C-Type Lectin-Like Molecule-1; CLL-1; DCAL2; CLL1; C-Type Lectin-Like Molecule 1; DCAL-2; Killer cell lectin like receptor subfamily L, member 1 (KLRL1); CD371 (Bakker A. et al. Cancer Res. 2004, 64, p 8843 50; GenBank™ access. no: AY547296; Zhang W. et al. GenBank™ access. no: AF247788; A. S. Marshall, et al. J Biol Chem 2004, 279, p 14792-802; GenBank™ access. no: AY498550; Y. Han et al. Blood 2004, 104, p 2858 66; H. Floyd, et al. GenBank™ access. no: AY426759; C. H. Chen, et al. Blood 2006, 107, p 1459 67). Ids: HGNC: 31713; Entrez Gene: 160364; Ensembl: ENSG00000172322; OMIM: 612088; UniProtKB: Q5QGZ9. CLEC12A is an antigen that is expressed on leukemic blast cells and on leukemic stem cells in acute myeloid leukemia (AML), including the CD34 negative or CD34 low expressing leukemic stem cells (side population) (A. B. Bakker et al. Cancer Res 2004, 64, p 8443 50; Van Rhenen et al. 2007 Blood 110:2659; Moshaver et al. 2008 Stem Cells 26:3059). Expression of CLEC12A is otherwise thought to be restricted to the hematopoietic lineage, particularly to myeloid cells in peripheral blood and bone marrow, i.e., granulocytes, monocytes and dendritic cell precursors. More importantly, CLEC12A is absent on hematopoietic stem cells. This expression profile makes CLEC12A a particularly favorable target in AML. The full length form of CLEC12A comprises 275 amino acid residues, including an additional intracellular stretch of 10 amino acids which is absent in most other isoforms, and shows the strictly myeloid expression profile (surface expression and mRNA level). The term 'CLEC12A or functional equivalent thereof' means all (such as splice and mutation) variants that are referenced above and isoforms thereof that retain the strict myeloid expression profile (both at surface expression level and mRNA level) as described in Bakker et al. Cancer Res 2004, 64, p 8443-50 and Marshall 2004—J Biol Chem 279(15), p 14792-802. A CLEC12A binding antibody of the invention binds human CLEC12A. Where herein reference is made to CLEC12A, the reference is to human CLEC12A, unless specifically stated otherwise.

CD3 (cluster of differentiation 3) T-cell co-receptor is a protein complex and is composed of four distinct chains. In mammals, the complex contains a CD3Y chain, a CD3δ chain, and two CD3ε chains. These chains associate with a molecule known as the T-cell receptor (TCR) and the ζ-chain to generate anactivation signal in T lymphocytes. The TCRα, TCRβ, ζ-chain, and CD3 molecules together comprise the TCR complex. CD3 is expressed on T cells. An antibody that binds CD3 can bind a CD3Y chain, a CD3δ chain, a CD3ε chain or a combination of CD3δ/CD3ε or CD3Y/CD3ε. The CD3 binding antibody of the present invention binds the CD3ε chain. CD3ε is known under various aliases some of which are: "CD3ε Molecule, Epsilon (CD3-TCR Complex)"; "CD3ε Antigen, Epsilon Polypeptide (TiT3 Complex)"; T-Cell Surface Antigen T3/Leu-4 Epsilon Chain; T3E; T-Cell Antigen Receptor Complex, Epsilon Subunit Of T3; CD3ε Antigen; CD3-Epsilon 3; IMD18; TCRE. Ids for CD3E Gene are HGNC: 1674; Entrez Gene: 916; Ensembl: ENSG00000198851; OMIM: 186830 and UniProtKB: P07766. Bispecific CD3 binding antibodies targeting the CD3ε chain have been shown to be effective in recruiting T cells to aberrant cells. Hence, an (bispecific) antibody according to the present invention preferably contains one heavy/light chain combination that binds CD3ε. A CD3 binding antibody of the invention binds human CD3. Where herein reference is made to CD3, the reference is to human CD3, unless specifically stated otherwise. CS-1 is also referred to as Citrate Synthase; EC 2.3.3.1; Citrate Synthase, Mitochondrial; EC 2.3.3. Ids: HGNC: 2422; Entrez Gene: 1431 Ensembl: ENSG00000062485; OMIM: 118950; UniProtKB: O75390.

EGFR is also referred to as Epidermal Growth Factor Receptor; Erythroblastic Leukemia Viral (V-Erb-B) Oncogene Homolog (Avian); ERBB1; PIG61; Proto-Oncogene C-ErbB-1; Avian Erythroblastic Leukemia Viral (V-Erb-B) Oncogene Homolog; Receptor Tyrosine-Protein Kinase ErbB-1; Cell Growth Inhibiting Protein 40; Cell Proliferation-Inducing Protein 61; HER1; mENA; EC 2.7.10.1; EC 2.7.10; Epidermal Growth Factor Receptor (Avian Erythroblastic Leukemia Viral (V-Erb-B) Oncogene Homolog). Ids: HGNC: 3236; Entrez Gene: 1956; Ensembl: ENSG00000146648; OMIM: 131550; UniProtKB: P00533.

EGFRvIII is a common variant of EGFR (Oncogene. 2013 May 23; 32(21):2670-81. doi: 10.1038/onc.2012.280. Epub 2012 Jul. 16).

Delta like 3 (DLL3) is also referred to as Delta-Like 3); *Drosophila* Delta Homolog 3; Delta3; Delta (*Drosophila*)-Like 3; SCDO1. Ids for DLL3 are: HGNC: 2909; Entrez Gene: 10683; Ensembl: ENSG00000090932; OMIM: 602768 and UniProtKB: Q9NYJ7.

LGR5 is Leucine-Rich Repeat Containing G Protein-Coupled Receptor 5 Alternative names for the gene or protein are Leucine-Rich Repeat Containing G Protein-Coupled Receptor 5; Leucine-Rich Repeat-Containing G Protein-Coupled Receptor 5; G-Protein Coupled Receptor HG38; G-Protein Coupled Receptor 49; G-Protein Coupled Receptor 67; GPR67; GPR49; Orphan G Protein-Coupled Receptor HG38; G Protein-Coupled Receptor 49; GPR49; HG38 and FEX. A protein or antibody of the invention that binds LGR5, binds human LGR5. The LGR5 binding protein or antibody of the invention may, due to sequence and tertiary structure similarity between human and other mammalian orthologs, also bind such an ortholog but not necessarily so. Database accession numbers for the human LGR5 protein and the gene encoding it are (NC_000012.12; NT_029419.13; NC_018923.2; NP_001264155.1; NP_001264156.1; NP_003658.1).

MSLN or mesothelin is also referred to as Mesothelin; Pre-Pro-Megakaryocyte-Potentiating Factor; CAK1 Antigen; MPF; Soluble MPF Mesothelin Related Protein; Megakaryocyte Potentiating Factor and SMRP. Ids for MSLN are: HGNC: 7371; Entrez Gene: 10232; Ensembl: ENSG00000102854; OMIM: 601051; UniProtKB: Q13421.

Folate receptor 1 is also referred to as FOLR1; Folate Receptor 1 Folate Receptor 1; Ovarian Tumor-Associated Antigen MOv18; Adult Folate-Binding Protein; Folate Receptor, Adult; KB Cells FBP; FR-Alpha; FOLR; FBP; Folate Binding Protein; and Folate Receptor 1. Ids for FOLR1 are HGNC: 3791; Entrez Gene: 2348; Ensembl: ENSG00000110195; OMIM: 136430; UniProtKB: P15328

Folate receptor 3 is also referred to as FOLR3; Folate Receptor 3 (Gamma); FR-Gamma; Folate Receptor 3; Gamma-HFR; and FR-G. Ids for FOLR3 are HGNC: 3795; Entrez Gene: 2352; Ensembl: ENSG00000110203; OMIM: 602469; and UniProtKB: P41439.

EPCAM is also referred to as Epithelial Cell Adhesion Molecule; EGP40; M4S1; ESA; MIC18; KS1/4; Tumor-Associated Calcium Signal Transducer 1; MK-1; TACSTD1; Human Epithelial Glycoprotein-2; TROP1; Membrane Component, Chromosome 4, Surface Marker (35 kD Glycoprotein); Adenocarcinoma-Associated Antigen; EGP; Cell Surface Glycoprotein Trop-1; Ep-CAM; Epithelial Glycoprotein 314; GA733-2; Major Gastrointestinal Tumor-Associated Protein GA733-2; M1S2; EGP314; CD326 Antigen; KSA; Epithelial Cell Surface Antigen; DIAR5; Epithelial Glycoprotein; HNPCC8; hEGP314; Antigen Identified By Monoclonal Antibody AUA1; KS 1/4 Antigen; EGP-2; ACSTD1. Ids: HGNC: 11529; Entrez Gene: 4072; Ensembl: ENSG00000119888; OMIM: 185535; UniProtKB: P16422.

HER2 is also referred to as V-Erb-B2 Avian Erythroblastic Leukemia Viral Oncogene Homolog 2; ERBB2; CD340; NGL; HER-2; HER-2/neu2; NEU2; TKR1; Neuro/Glioblastoma Derived Oncogene Homolog; C-Erb B2/Neu Protein; Metastatic Lymph Node Gene 19 Protein; herstatin; Proto-Oncogene C-ErbB-2; Neuroblastoma/Glioblastoma Derived Oncogene Homolog; Proto-Oncogene Neu; Receptor Tyrosine-Protein Kinase ErbB-2; Tyrosine Kinase-Type Cell Surface Receptor HER2; V-Erb-B2 Erythroblastic Leukemia Viral Oncogene Homolog 2, Neuro/Glioblastoma Derived Oncogene Homolog; MLN 19; MLN19; p185erbB2; CD340 Antigen; EC 2.7.10.1; EC 2.7.10; V-Erb-B2 Avian Erythroblastic Leukemia Viral Oncogene Homolog 2 (Neuro/Glioblastoma Derived Oncogene Homolog). Ids:
HGNC: 3430; Entrez Gene: 2064; Ensembl: ENSG00000141736; OMIM: 164870; UniProtKB: P04626.

HM1.24 is also referred to as BST2; Bone Marrow Stromal Cell Antigen 2; TETHERIN; BST-2; Bone Marrow Stromal Antigen 2; HM1.24 Antigen; Tetherin; CD317; CD317 Antigen; NPC-A-7. Ids: HGNC: 1119; Entrez Gene: 684; Ensembl: ENSG00000130303; OMIM: 600534; UniProtKB: Q10589.

MCSP is also referred to as Sperm Mitochondria-Associated Cysteine-Rich Protein (SMCP); MCSP; MCS; Mitochondrial Capsule Selenoprotein; HSMCSGEN1; Sperm Mitochondrial-Associated Cysteine-Rich Protein. Ids:

HGNC: 6962; Entrez Gene: 4184; Ensembl: ENSG00000163206; OMIM: 601148; UniProtKB: P49901.

PSMA is also referred to as Folate Hydrolase (Prostate-Specific Membrane Antigen) 1; FOLH1; NAALAD1; FOLH; mGCP; Glutamate Carboxypeptidase II; N-Acetylated-Alpha-Linked Acidic Dipeptidase I; PSM; NAALADase I; PSMA; EC 3.4.17.21; Glutamate Carboxylase II; GCP2; Cell Growth-Inhibiting Gene 27 Protein; NAALAdase; Folylpoly-Gamma-Glutamate Carboxypeptidase; Glutamate Carboxypeptidase 2; Membrane Glutamate Carboxypeptidase; N-Acetylated Alpha-Linked Acidic Dipeptidase 1; Pteroylpoly-Gamma-Glutamate Carboxypeptidase; Prostate Specific Membrane Antigen Variant F; FGCP; Folate Hydrolase 1; GCPII; Prostate-Specific Membrane Antigen. Ids: HGNC: 3788; Entrez Gene: 2346; Ensembl: ENSG00000086205; OMIM: 600934; UniProtKB: Q04609.

PSMA is not to be confused with Proteasome (Prosome, Macropain) Subunit, Alpha Type, 1 which is also known under the alias PSMA1.

Accession numbers are primarily given to provide a further method of identification of a target, the actual sequence of the protein bound may vary, for instance because of a mutation in the encoding gene such as those occurring in some cancers or the like. The antigen binding site binds the antigen and a variety of variants thereof, such as those expressed by some antigen positive immune or tumor cells.

When herein reference is made to a gene, a protein, the reference is preferably to the human form of the gene or protein. When herein reference is made to a gene or protein reference is made to the natural gene or protein and to variant forms of the gene or protein as can be detected in tumours, cancers and the like, preferably as can be detected in human tumours, cancers and the like.

A bispecific antibody of the invention preferably binds to the human BCMA, CD19, CD20, CD30, CD33, CD38, CD44, CD123, CD138, CEA, CLEC12A, CS-1, EGFR, EGFRvIII, EPCAM, DLL3, LGR5, MSLN, FOLR1, FOLR3, HER2, HM1.24, MCSP, PSMA protein or a variant thereof. Needless to say that the antigen binding heavy/light chain combination preferably binds the extracellular part of the antigen. A bispecific antibody according to the invention preferably binds to human CLEC12A or a variant thereof. A preferred bispecific antibody according to the invention binds to human CD3 and human CLEC12A or a variant thereof.

HGNC stands for the HUGO Gene nomenclature committee. The number following the abbreviation is the accession number with which information on the gene and protein encoded by the gene can be retrieved from the HGNC database. Entrez Gene provides the accession number or gene ID with which information on the gene or protein encoded by the gene can be retrieved from the NCBI (National Center for Biotechnology Information) database. Ensemble provides the accession number with which information on the gene or protein encoded by the gene can be obtained from the Ensemble database. Ensembl is a joint project between EMBL-EBI and the Wellcome Trust Sanger Institute to develop a software system which produces and maintains automatic annotation on selected eukaryotic genomes.

The invention provides an antibody that binds human CD3 which antibody comprises a heavy chain and light chain wherein said heavy chain comprises a variable region that comprises an amino acid sequence:

```
QVQLV QSGGG VVQPG RSLRL SCVASG FTFSS YGMHW VRQAP
GKGLE WVAAI WYX1X2R KQDYA DSVKG RFTIS RDNSK NTLYL
QMNSL RAEDT AVYYC TRGTG YNWFD PWGQG TLVTV SS
``` with 0-10, preferably, 0-5 amino acid insertions, deletions, substitutions, additions or a combination thereof at one or more positions other than the position indicated by $X_1X_2$; wherein
$X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A.

In a preferred embodiment the light chain comprises a light chain variable region comprising the amino acid sequence of an O12/IgVκ1-39*01 gene segment as depicted in FIG. 23A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/IgVκ1-39*01 gene segment as depicted in FIG. 23A with 0-10, preferably 0-5 amino acid insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 23A. This lists the sequence of the V-region. The V-region can be combined with one of five J-regions. FIGS. 23B and 23C describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the O12/IgVκ1-39*01 comprising light chain variable region is a germline sequence. It is further preferred that the IGJκ1*01 or/IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Mature B-cells that produce an antibody with an O12 light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "O12 light chains" will include O12-derived light chains, The mutations that are introduced by somatic hypermutation can of course also be introduced artificially in the lab. In the lab also other mutations can be introduced without affecting the properties of the light chain in kind, not necessarily in amount. A light chain is at least an O12 light chain if it comprises a sequence as depicted in FIG. 23A, FIG. 23B or FIG. 23C with 0-10, preferably 0-5 amino acid insertions, deletions, substitutions, additions or a combination thereof. In a preferred embodiment the O12 light chain is a light chain comprising a sequence as depicted in FIG. 23A, FIG. 23B or FIG. 23C with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 23A, FIG. 23B or FIG. 23C with 0-5, preferably 0-4, more preferably 0-3 amino acid insertions, deletions, substitutions, additions or a combination thereof. In a preferred embodiment the O12 light chain is a light chain comprising a sequence as depicted in FIG. 23A, FIG. 23B or FIG. 23C with 0-2, more preferably 0-1, most preferably 0 amino acid insertions, deletions, substitutions, additions or a combination thereof. In a preferred embodiment the O12 light chain is a light chain comprising a sequence as depicted in FIG. 23A or FIG. 23B with the mentioned amino acid insertions, deletions, substitutions, additions or a combination thereof. In a preferred embodiment the light chain comprises the sequence of FIG. 23B.

The antibody is preferably a bispecific antibody. The bispecific antibody preferably has one heavy chain variable region/light chain variable region (VH/VL) combination that binds CD3 and a second VH/VL combination that binds an antigen other than an antigen on CD3. In a preferred embodiment the antigen is a tumor antigen. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds CD3 and one H/L chain combination that binds another antigen, preferably a tumor antigen. In a preferred embodiment the light chain in said first H/L chain combination is similar to the light chain in said second H/L chain combination. In a more preferred embodiment, the light chains in the first and second H/L chain combinations are identical, i.e. a similar or identical human light chain is a so-called 'common light chain', which is a light chain that can combine with different heavy chains to form antibodies with functional antigen binding domains. In a preferred embodiment the light chain in said first H/L chain combination comprises a light chain variable region that is similar to the light chain variable region in said second H/L chain combination. In a more preferred embodiment, the light chain variably regions in the first and second H/L chain combinations are identical, i.e. a similar or identical human light chain variable region is a so-called 'common light chain variable region', which is a light chain variable region that can combine with different heavy chain variable regions to form antibodies with functional antigen binding domains. The light chain comprising a common light chain variable region is preferably a common light chain. The light chain preferably comprises a light chain variable region comprising the amino acid sequence of an O12/IgVκ1-39*01 gene segment as depicted in FIG. 23A with 0-10, preferably 0-5 amino acid insertions, deletions, substitutions, additions or a combination thereof as further defined elsewhere herein. Preferably, the common light chain has a germline sequence. A preferred germline sequence is a light chain variable region that is frequently used in the human repertoire and has good thermodynamic stability, yield and solubility. A preferred germline light chain is O12 as indicated herein above. A preferred sequence for O12/IgVκ1-39 is given in FIG. 23A. This lists the sequence of the V-region. FIGS. 23B and 23C describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01.

It is preferred that the O12/IgVκ1-39*01 light variable region is a germline sequence. It is preferred that the O12/IgVκ1-39*01 comprising light chain variable region is a germline sequence. It is further preferred that the IGJκ1*01 or/IGJκ5*01 comprising light chain variable region is a germline sequence. In a preferred embodiment, the IGKV1-39/jk1 or IGKV1-39/jk5 light chain variable regions are germline sequences. The O12 light chain of the bispecific antibody is preferably an O12 light chain as indicated herein above.

A tumor antigen is defined by the pattern of its expression. A tumor-specific antigen, is typically present only on cells of a tumor and not on any other cell in the post-natal, preferably adult human body. A tumor-associated antigen is typically present on cells of a tumor and also some normal cells in the post-natal, preferably adult human body. A tumor antigen as used herein is typically a tumor-specific or a tumor-associated antigen. Tumor antigens may be involved in the oncogenic process or not. The may be different from the "normal" protein in healthy individuals or not. It is noted that various tumor-specific antigens were later shown to be expressed also on some other non-tumorigenic cells. Preferred tumor antigens are tumor-antigens that are expressed on the cell surface and which have an extra-cellular part. The antibody typically binds to an extra-cellular part of the antigen.

The term "antibody" as used herein means a proteinaceous molecule belonging to the immunoglobulin class of proteins, containing one or more domains that bind an epitope on an antigen, where such domains are derived from or share sequence homology with the variable region of an antibody. Antibodies are typically made of basic structural units—each with two heavy chains and two light chains. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Binding, or "specifically recognizing" is defined as binding with affinities (KD) of at least $1\times10e-6$ M, $1\times10e-7$ M, $1\times10e-8$ M, or at least $1\times10e-9$ M. Antibodies for therapeutic applications can have affinities of $1\times10e-10$ M or even higher. Antibodies of the present invention are typically bispecific antibodies and of the human IgG subclass. Preferably, the antibodies of the present invention are of the human IgG1 subclass. Most preferably, antibodies of the present invention are full length IgG molecules. The invention also provides a derivative and/or analogue of an antibody of the invention. Such a derivative and/or analogue has the VH/VL domains of an antibody of the invention, preferably including the common light chain variable region as defined elsewhere herein. Suitable derivatives are single chain Fv-fragments, monobodies, VHH and Fab-fragments. The derivatives may be fused to the $C_H2$ and $C_H3$ domain of a heavy chain of an antibody. The derivative preferably further comprises the $C_H1$ domain of a heavy an antibody and the CL domain of a light chain of an antibody. The derivative can also be in a multivalent format, preferably a bispecific format wherein one of the VH/VL domains of an antibody comprises a heavy chain variable region/light chain variable region (VH/VL) combination that binds CD3 of the invention and at least one other VH/VL domain of an antibody that binds an antigen that is not a CD3 antigen. The at least one other VH/VL domain of an antibody preferably binds a tumor antigen, preferably CLEC12A. Multivalent formats are easily produced for instance by producing the derivative as a fusion protein with or without suitable and/or the conventional peptide linker or spacer between the VH/VL domains.

A "bispecific antibody" is an antibody as described herein above comprising one heavy chain variable region/light chain variable region (VH/VL) combination that binds CD3 and a second VH/VL combination that binds an antigen other than CD3, preferably a tumor antigen. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which comprises one heavy/light chain combination that binds CD3 and one heavy/light chain combination that binds another antigen, preferably a tumor antigen.

Binding of the heavy/light chain combination to the antigen is achieved via the antigen binding site in the variable region of the heavy/light chain combination.

The invention also provides alternative bispecific formats, such as those described in Spiess, C., et al., (Alternative molecular formats and therapeutic applications for bispecific antibodies. Mol. Immunol. (2015) http://dx.doi.org/10.1016/j.molimm.2015.01.003). Bispecific antibody formats that are not classical antibodies with two H/L combinations, have at least a variable domain comprising a heavy chain variable region and a light chain variable region of the invention. This variable domain may be linked to a single chain Fv-fragment, monobody, a VHH and a Fab-fragment that provides the second binding activity.

The term bispecific antibody may be replaced by the broader term "a bispecific binding protein comprising an immunoglobulin variable domain that binds CD3 having a heavy chain variable region and a light chain variable region of the invention; and an antigen binding (poly)peptide that binds another antigen. In this embodiment the binding (poly)peptide is preferably a (poly)peptide as specified in Spiess et al (supra).

In a bispecific antibody of the invention the light chain in the CD3-binding H/L chain combination is preferably similar to the light chain in H/L chain combination that can bind an antigen other than CD3, preferably a tumor antigen. In a more preferred embodiment, the light chain in both H/L chain combinations is identical, i.e. said human light chain is a so-called 'common light chain', which is a light chain that can combine with different heavy chains to form antibodies with functional antigen binding domains. Preferably, the common light chain has a germline sequence. A preferred germline sequence is a light chain variable region that is frequently used in the human repertoire and has good thermodynamic stability, yield and solubility. A preferred germline light chain is O12, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org).

The term 'common light chain' as used herein refers to the two light chains (or the VL part thereof) in the bispecific antibody. The two light chains (or the VL part thereof) may be identical or have some amino acid sequence differences while the binding specificity of the full length antibody is not affected. It is for instance within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably.

Preferably, the common light chain has a germline sequence. A preferred germline sequence is a light chain variable region that is frequently used in the human repertoire. A preferred germline light chain is O12, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, insertions and/or additions) are present that do not materially influence the formation of functional binding regions. The light chain of the present invention can also be a light chain as specified herein above, having 0-10, preferably 0-5 amino acid insertions, deletions, substitutions, additions or a combination thereof.

An antibody of the invention is preferably an IgG antibody, preferably an IgG1 antibody. The term 'full length IgG' according to the invention is defined as comprising an essentially complete IgG, which however does not necessarily have all functions of an intact IgG. For the avoidance of doubt, a full length IgG contains two heavy and two light chains. Each chain contains constant (C) and variable (V) regions, which can be broken down into domains designated CH1, CH2, CH3, VH, and CL, VL. An IgG antibody binds to antigen via the variable region domains contained in the Fab portion, and after binding can interact with molecules and cells of the immune system through the constant domains, mostly through the Fc portion. Full length antibodies according to the invention encompass IgG molecules wherein mutations may be present that provide desired characteristics. Full length IgG should not have deletions of substantial portions of any of the regions. However, IgG molecules wherein one or several amino acid residues are deleted, without essentially altering the binding characteristics of the resulting IgG molecule, are embraced within the term "full length IgG". For instance, such IgG molecules can have a deletion of between 1 and 10 amino acid residues, preferably in non-CDR regions, wherein the deleted amino acids are not essential for the binding specificity of the IgG.

Full length IgG antibodies are used because of their favourable half-life and the desire to stay as close to fully autologous (human) molecules for reasons of immunogenicity. IgG1 is favoured based on its long circulatory half-life in man. In order to prevent or avoid immunogenicity in humans it is preferred that the bispecific full length IgG antibody according to the invention is a human IgG1. The term 'bispecific' means that one heavy and light chain combination (H/L combination) or arm of the antibody binds to a first antigen whereas the other H/L combination or other arm binds to a second antigen, wherein said first and second antigens are not identical. An antigen, is typically a molecule which serves as a target for an antibody. In the present invention it is preferred that an antigen is a protein expressed on the membrane of a cell of an individual. According to the present invention, said first and second antigens are on two different molecules that are preferably located on two different cell types. The term 'one arm [of the antibody]' preferably means the heavy chain/light chain combination comprising one Fab portion of a full length IgG antibody. Bispecific antibodies that mediate cytotoxicity by recruiting and activating endogenous immune cells are an emerging class of next generation antibody therapeutics. This can be achieved by combining antigen binding specificities for target cells (i.e., tumor cells) and effector cells (i.e., T cells, NK cells, and macrophages) in one molecule (Cui et al. JBC 2012 (287) 28206 28214; Kontermann, MABS 2012 (4) 182 197; Chames and Baty, MABS 2009 (1) 539 547; Moore et al. Blood 2011 (117) 4542 4551; Loffler et al. 2000 Blood 95:2098; Zeidler et al. 1999 J. Immunol. 163:1246). According to the invention, bispecific antibodies are provided wherein one heavy/light chain combination binds the CLEC12A antigen on aberrant (tumor) cells whereas the second heavy/light chain combination binds CD3 on immune effector cells.

The invention provides bispecific IgG antibodies wherein one heavy/light chain combination specifically recognizes CLEC12A or a functional equivalent thereof, including those functional CLEC12A equivalents that lack the above mentioned additional intracellular stretch of 10 amino acids. A bispecific IgG antibody wherein one heavy/light chain combination binds the full length form of CLEC12A is preferred. Needless to say that the tumor antigen binding heavy/light chain combination binds the extracellular part of tumor antigen.

The terms 'variable region domain', 'variable region', 'variable domain', 'VH/VL pair', 'VH/VL', 'VH', 'VL', 'Fab portion', 'Fab arm', 'Fab' or 'arm' are used herein interchangeably.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other proteins as well, antibodies according to the present invention that bind CD3 or CLEC12A may recognize other proteins as well, if such other proteins contain the same epitope. Hence, the term "binding" does not exclude binding of the antibodies to another protein or protein(s) that contain the same epitope. A heavy/light chain combination that binds CD3 in antibody of the invention does not bind to other proteins on the membrane of cells in a post-natal, preferably adult human. A heavy/light chain combination that binds CLEC12A of the invention does not bind other proteins on the membrane of cells in a post-natal, preferably adult human.

A bispecific antibody according to the present invention that binds CD3 and a tumor antigen binds to CD3 (preferably CD3 on effector cells) with a binding affinity of at least 1×10e-6 M, as outlined in more detail below. In a preferred embodiment the CD3 binding affinity is 1×10e-6 M-1×10e-10 M, preferably 1×10e-7 M-1×10e-9 M.

A bispecific antibody according to the present invention that binds CD3 and a tumor antigen binds to the tumor antigen preferably with a binding affinity that is higher than the affinity with which it binds CD3. In a preferred embodiment the affinity of binding of the tumor antigen on tumor cells is at least 2 times, more preferably 4 times more preferably 6 times, or 10 times higher than the affinity of binding to CD3. In a preferred embodiment the tumor antigen binding affinity is 1×10e-6 M-1×10e-10 M, preferably 1×10e-7 M-1×10e-10 M, more preferably at least 1×10e-8, preferably at least 1×10e-9. Preferably in combination with a CD3 affinity that is at least 2 times, more preferably 4 times more preferably 6 times, or 10 times lower than the indicated affinity of binding to the tumor antigen. In a preferred embodiment the tumor antigen binding affinity is 1×10e-8-1×10e-10.

The term 'aberrant cells' as used herein includes tumor cells, more specifically tumor cells of hematological origin including also pre-leukemic cells such as cells that cause myelodysplastic syndromes (MDS) and leukemic cells such as acute myeloid leukemia (AML) tumor cells or chronic myelogenous leukemia (CML) cells.

The term 'immune effector cell' or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte.

According to the invention, recruitment of effector cells to aberrant cells means that immune effector cells are brought in close vicinity to the aberrant target cells such that the effector cells can directly kill, or indirectly initiate the killing of the aberrant cells that they are recruited to. It is preferred that a CD3 binding antibody binds CD3 on the surface of effector cells.

An antibody that binds human CD3 of the invention comprises a heavy chain variable region that comprises an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A.

The heavy chain variable region can have 0-10, preferably 0-5 amino acid insertions, deletions, substitutions, additions with respect to the indicated amino acid sequence, or a combination thereof. Amino acid insertions, deletions, substitutions, additions with respect to the indicated sequence or a combination thereof, are of course only at positions other than the positions indicated by $X_1X_2$. At the positions indicated by $X_1X_2$ only the indicated amino acids are allowed. In a preferred embodiment the heavy chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof at positions other than the positions indicated by $X_1X_2$. A combination of an insertion, addition, deletion or substitution is a combination as claimed if aligned sequences do not differ at more than 10, preferably no more than 5 positions. A gap in one of the aligned sequences counts for as many amino acids as skipped in the other sequence.

The amino acid insertions, deletions, substitutions, additions or combination thereof are preferably not in the CDR3 region of the heavy chain variable region, preferably not in the CDR1 and/or CDR2 region of the heavy chain variable region. In a preferred embodiment the heavy chain variable region does not comprise a deletion, addition or insertion with respect to the sequence indicated. In this embodiment the heavy chain variable region can have 0-10, preferably 0-5 amino acid substitutions with respect to the indicated amino acid sequence. An amino acid substitution is preferably a conservative amino acid substitution.

An antibody that binds human CD3 of the invention comprising a heavy chain variable region that comprises an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A, is preferably an antibody comprising a heavy chain variable region that comprises an amino acid sequence identified by the numbers 5192; 5193; 5196; 5197; 5351; 5354; 5356; 5603; 5616; 5626; 5630; 5648; 5661; or 5694 as depicted in FIGS. 12, 25 and 28. The heavy chain variable region preferably comprises an amino acid sequence identified by the numbers 5196; 5197; 5603; 5616; 5626; 5630; 5648; 5661; or 5694 as depicted in FIGS. 12 and 25. The heavy chain variable region of the antibody preferably comprises an amino acid sequence identified by the number 5196 as depicted in FIG. 12.

The invention further provides a bispecific antibody that binds human CD3 of the invention that comprises a heavy chain and a light chain wherein the heavy chain variably region of said heavy chain comprises an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A.

The light chain is preferably a common light chain as defined elsewhere herein. The bispecific antibody further comprises a heavy chain and light chain combination that binds another antigen, preferably a tumor antigen. The light chain of the heavy chain and light chain combination that binds another antigen is preferably a common light chain as defined elsewhere herein. The heavy chain that comprises a heavy chain variable region comprising an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A, is preferably a heavy chain that comprises a heavy chain variable region comprising an amino acid sequence identified by the numbers 5192; 5193; 5196; 5197; 5351; 5354; 5356; 5603; 5616; 5626; 5630; 5648; 5661; or 5694 as depicted in FIGS. 12, 25 and 28. The heavy chain variable region of the bispecific antibody preferably comprises an amino acid sequence identified by the numbers 5196; 5197; 5603; 5616; 5626; 5630; 5648; 5661; or 5694 as depicted in FIGS. 12 and 25. The heavy chain variable region of the bispecific antibody preferably comprises an amino acid sequence identified by the number 5196 as depicted in FIG. 12.

A bispecific antibody of the invention that comprises a heavy chain variable region that comprises an amino acid sequence:

```
QVQLV QSGGG VVQPG RSLRL SCVASG FTFSS YGMHW VRQAP
GKGLE WVAAI WYX₁X₂R KQDYA DSVKG RFTIS RDNSK NTLYL
QMNSL RAEDT AVYYC TRGTG YNWFD PWGQG TLVTV SS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A preferably further comprises a heavy/light chain combination that binds human CLEC12A. In a preferred embodiment the heavy chain of the heavy/light chain combination that binds human CLEC12A comprises a variable region that comprises an amino acid sequence:

```
QVQLV QSGAE VKKPG ASVKV SCKAS GYTFT SYYMH WVRQA
PGQGL EWMGI INPSG GSTSY AQKFQ GRVTM TRDTS TSTVY
MELSS LRSED TAVYY CAKGT TGDWF DYWGQ GTLVT VSS;

EVQLV QSGAE VKKPG ASVKV SCKAS GYTFT SYYMH WVRQA
PGQGL EWMGI INPSG GSTSY AQKFQ GRVTM TRDTS TSTVY
MELSS LRSED TAVYY CARGN YGDEF DYWGQ GTLVT VSS;
or

QVQLV QSGAE VKKPG ASVKV SCKAS GYTFT GYYMH WVRQA
PGQGL EWMGW INPNS GGTNY AQKFQ GRVTM TRDTS ISTAY
MELSR LRSDD TAVYY CARDG YFADA FDYWG QGTLV TVSS;
``` with 0-10, preferably 0-5 amino acid insertions, deletions, substitutions, additions or a combination thereof.

The heavy chain variable region of the heavy/light chain combination that binds human CLEC12A can have 0-10, preferably 0-5 amino acid insertions, deletions, substitutions, additions with respect to the indicated amino acid sequence, or a combination thereof. In a preferred embodiment the heavy chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof. A combination of an insertion, deletion, addition or substitution is a combination as claimed if aligned sequences do not differ at more than 5 positions. A gap in one of the aligned sequences counts for as many amino acid as skipped in the other sequence.

An amino acid insertion, deletion, substitution, addition or combination thereof in a CD3 heavy chain variable region as described herein preferably leaves H35, A61, Y102, N103, and W104 and positions in the CDR3 VH unchanged. If A50 is modified it is preferably substituted by an S, Y, M or a Q. If D59 is modified it is preferably substituted by an Y or an E, However substitution of D59 by L, I, V, F, R, A, N, H, S, T is also possible. If A61 is substituted it is preferably substituted for by N, I, H, Q, L, R, Y, E, S, T, D, K, V. If F105 is modified it is preferably substituted by an Y or an M. For the CD3 VH of the invention H35, Y102, N103, and W104 residues are thought to be relevant for CD3 binding. Other specific substitutions at the A50, D59, A61 and F105 positions are also relevant but do not have to affect CD3 binding. Table 2 lists amino acid substitution introduced in column 2. Those that were also recovered are mentioned in column 3. Amino acid substitutions that were introduced but not recovered are thought to affect the antibody and are not desired. For instance an A50I mutation is not desired. Tolerated amino acid substitutions can easily be found using the method described in example 5A together with CIEX-HPLC after storage.

An amino acid insertion, deletion, substitution, addition or combination thereof is preferably not done in the binding interphase of the heavy and light chain.

If an amino acid is changed in the interphase of the H/L chain interaction, it is preferred that the corresponding amino acids in the other chain are changed to accommodate the change. An insertion or addition of an amino acid preferably does not entail the insertion or addition of a proline.

An addition of an amino acid can in principle be regarded to be the same as an insertion. Adding an amino acid to one of the ends of a polypeptide chain is sometimes not considered an insertion but as a strict addition (prolongation). For the present invention both an addition within a chain or to one of the ends, are considered to be an insertion.

The amino acid insertions, deletions, substitutions, additions or combination thereof are preferably not in the CDR3 region of the heavy chain variable region, preferably not in the CDR1 or CDR2 region of the heavy chain variable region. In a preferred embodiment the heavy chain variable region does not comprise a deletion, addition or insertion with respect to the sequence indicated. In this embodiment the heavy chain variable region can have 0-5 amino acid substitutions with respect to the indicated amino acid sequence. An amino acid substitution is preferably a conservative amino acid substitution. The CDR1, CDR2 and CDR3 of a CD3 binding VH of the invention preferably comprise respectively the amino acid sequence GFTFSSYG for CDR1 (according to IMGT), IWYNARKQ for CDR2 and GTGYNWFDP for CDR3. The CDR1, CDR2 and CDR3 of a CLEC12A binding VH of the invention preferably comprises respectively the amino acid sequence GYTFTSYY for CDR1, INPSGGST for CDR2, and GTTGDWFDY for CDR3.

The light chain variable region comprises preferably a germline O12 variable region V-segment. In a preferred embodiment the light chain variable region comprises the kappa light chain V-segment IgVκ1-39*01. In a particularly preferred embodiment the light chain variable region comprises the kappa light chain IgVκ1-39*01/IGJκ1*01 or IgVκ1-39*01/IGJκ1*05. In a most preferred embodiment the light chain variable region comprises a germline kappa light chain IgVκ1-39*01/IGJκ1*01 sequence.

In a bispecific antibody of the invention it is preferred that the light chain is the same for both heavy chain/light chain combinations. Such a light chain is also referred to as a "common light chain". The term 'common light chain' according to the invention refers to light chains which may be identical or have some amino acid sequence differences while retaining the binding specificity of the antibody. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998, Nissim et al. 1994). Preferably, the common light chain has a germline sequence. A preferred germline sequence is a light chain variable region that is frequently used in the human repertoire and has superior ability to pair with many different VH regions, and has good thermodynamic stability, yield and solubility.

In a preferred embodiment the common light chain comprises a light chain variable region that comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01. In a preferred embodiment a germline IgVκ1-39*01/IGJκ1*01 Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions.

In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK with 0-10, preferably 0-5 amino acid insertions, deletions, substitutions, additions or a combination thereof. In a preferred embodiment the light chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof. A combination of an insertion, deletion, addition or substitution is a combination as claimed if aligned sequences do not differ at more than 5 positions. A gap in one of the aligned sequences counts for as many amino acid as skipped in the other sequence. In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK. In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK. In another preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK.

The amino acid insertions, deletions, substitutions, additions or combination thereof are preferably not in the CDR3 region of the light chain variable region, preferably not in the CDR1 or CDR2 region of the heavy chain variable region. In a preferred embodiment the heavy chain variable region does not comprise a deletion, addition or insertion with respect to the sequence indicated. In this embodiment the heavy chain variable region can have 0-5 amino acid substitutions with respect to the indicated amino acid sequence. An amino acid substitution is preferably a conservative amino acid substitution. The CDR1, CDR2 and CDR3 of a light chain of an antibody of the invention preferably comprises respectively the amino acid sequence CDR1—QSISSY, CDR2—AAS, CDR3—QQSYSTP, i.e. the CDRs of IGKV1-39 (according to IMGT).

As mentioned herein above, it is preferred that the antibody of the invention is a bispecific antibody. In a preferred embodiment the bispecific antibody comprises a CD3 binding heavy/light chain combination as indicated herein, and a heavy/light chain combination that binds a tumor antigen. In a preferred embodiment the tumor antigen-binding heavy/light chain combination binds CLEC12A.

The constant region of a (bispecific) antibody of the present invention is preferably a human constant region. The constant region may contain one or more, preferably not more than 10, preferably not more than 5 amino-acid differences with the constant region of a naturally occurring human antibody. Various variable domains of antibodies produced herein are derived from a human antibody variable domain library. As such these variable domains are human. The unique CDR regions may be derived from humans, be synthetic or derived from another organism. An antibody or bispecific antibody of the invention is preferably a human or humanized antibody.

In the art various methods exist to produce antibodies. Antibodies are typically produced by a cell that expresses nucleic acid encoding the antibody. Suitable cells for antibody production are a hybridoma cell, a Chinese hamster ovary (CHO) cell, an NS0 cell or a PER-C6 cell. In a particularly preferred embodiment said cell is a CHO cell.

Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. In a preferred embodiment the invention provides an industrial cell line that produces and an antibody of the invention.

The invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER.C6 cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy and light chain of an antibody as claimed. Preferably said nucleic acid molecule encodes a VH identified by numeral 5196 of FIG. 12, a nucleic acid molecule encoding a VH as identified by numeral 4327 of FIG. 24 or a combination thereof.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6 cell line or equivalent thereof. In a particularly preferred embodiment said cell is a CHO cell or a variant thereof. Preferably a variant that makes use of a Glutamine synthetase (GS) vector system for expression of an antibody.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

Bispecific antibodies are typically also produced by cells that express nucleic acid encoding the antibody. In this case the cell expresses the different light and heavy chains that make up the bispecific antibody. To this end the cell expresses two different heavy chains and at least one light chain. As unmodified heavy chains can pair with each other to form dimers such cells typically produce the two monoclonal antibodies (homodimers), in addition to the bispecific antibody (heterodimer). The number of possible heavy/light chain combinations in the produced antibodies increases when the cell expresses two or more light chains. To reduce the number of different antibody species (combinations of different heavy and light chains) produced the afore mentioned "common light chain" is preferred.

An antibody producing cell that expresses a common light chain and equal amounts of the two heavy chains typically produces 50% bispecific antibody and 25% of each of the monospecific antibodies (i.e. having identical heavy light chain combinations). Several methods have been published to favor the production of the bispecific antibody or vice versa, the monospecific antibodies. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art (see for instance Gunasekaran et al. JBC 2010 (285) 19637-19646). The compatible heterodimerization domains are preferably compatible immunoglobulin heavy chain CH3 heterodimerization domains. The art describes various ways in which such hetero-dimerization of heavy chains can be achieved. One way is to generate 'knob into hole' bispecific antibodies. See US Patent Application 20030078385 (Arathoon et al. —Genentech).

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954); incorporated herein by reference) methods and means are disclosed for producing bispecific antibodies using compatible heterodimerization domains. These means and methods can also be favorably employed in the present invention. Specifically, preferred mutations to produce essentially only bispecific full length IgG molecules are the amino acid substitutions L351K and T366K (numbering according to Kabat) in the first CH3 domain (the 'KR-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' bispecific molecules). Homodimerization of DE-variant heavy chains (DEDE homodimers) or KK-variant heavy chains (KKKK homodimers) hardly occurs due to strong repulsion between the charged residues in the CH3-CH3 interface between identical heavy chains. In one embodiment the heavy chain/light chain combination that comprises the variable domain that binds CD3, comprises a KK variant of the heavy chain. In this embodiment the heavy chain/light chain combination that comprises the variable domain that binds an antigen other than CD3 comprises a DE variant of the heavy chain. In a preferred embodiment the antigen other than CD3 is CLEC12A. In a preferred embodiment the VH of the variable domain that binds CLEC12A is MF4327_VH as depicted in FIG. 24.

Some antibodies are modified in CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. Such a mutant CH2 and/or lower hinge domain preferably comprise an amino substitution at position 235 and/or 236 (Kabat numbering), preferably an L235G and/or G236R substitution.

The invention further provides a method of treating cancer or a risk of cancer in a subject comprising administering to the subject in need thereof a bispecific antibody that binds human CD3 which antibody comprises a heavy chain and light chain wherein said heavy chain comprises a variable region that comprises the amino acid sequence:

```
QVQLV QSGGG VVQPG RSLRL SCVAS GFTFS SYGMH WVRQA
PGKGL EWVAA IWYX1X2 RKQDY ADSVK GRFTI SRDNS KNTLY
LQMNS LRAED TAVYY CTRGT GYNWF DPWGQ GTLVT VSS
``` with 0-10, preferably 0-5 amino acid insertions, deletions, substitutions, additions or a combination thereof at one or more positions other than the position indicated by $X_1X_2$; wherein $X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A; and a heavy chain-light chain (H/L) combination that binds a tumor-antigen.

The light chain preferably comprises a common light chain variable region. Said common light chain variable region preferably comprises an O12/IgVκ1-39 light chain variable region. Said light chain variable region is preferably a germline O12/IgVκ1-39*01 variable region. Said light chain variable region preferably comprises the kappa light chain IgVκ1-39*01/IGJκ1*01 or IgVκ1-39*01/IGJκ5*01. The light chain variable region preferably comprises the germline kappa light chain IgVκ1-39*01/IGJκ1*01 or IgVκ1-39*01/IGJκ5*01. Said light chain variable region preferably comprises the amino acid sequence.

DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK with 0-5 amino acid insertions, deletions, substitutions, additions or a combination thereof. Preferably the heavy chain/light chain (H/L) chain combination that binds a tumor-antigen binds CLEC12A.

The antibody is preferably a human or humanized antibody. Preferably the antibody comprises two different immunoglobulin heavy chains with compatible heterodimerization domains. Said compatible heterodimerization domains are preferably compatible immunoglobulin heavy chain CH3 heterodimerization domains. Said bispecific antibody is preferably an IgG antibody with a mutant CH2 and/or lower hinge domain such that interaction of the bispecific IgG antibody to a Fc-gamma receptor is reduced. The mutant CH2 and/or lower hinge domain preferably comprise an amino substitution at position 235 and/or 236 (Kabat numbering), preferably an L235G and/or G236R substitution. The antibody preferably comprises a common light chain.

Also provided is a bispecific antibody that binds human CD3 which antibody comprises a heavy chain and light chain wherein said heavy chain comprises a variable region that comprises the amino acid sequence:

```
QVQLV QSGGG VVQPG RSLRL SCVAS GFTFS SYGMH WVRQA
PGKGL EWVAA IWYX₁X₂ RKQDY ADSVK GRFTI SRDNS KNTLY
LQMNS LRAED TAVYY CTRGT GYNWF DPWGQ GTLVT VSS
``` with 0-10, preferably 0-5 amino acid insertions, deletions, substitutions, additions or a combination thereof at one or more positions other than the position indicated by $X_1X_2$; wherein
$X_1$=N and $X_2$=A;
$X_1$=N and $X_2$=T;
$X_1$=S and $X_2$=G;
$X_1$=H and $X_2$=G;
$X_1$=D and $X_2$=G; or
$X_1$=H and $X_2$=A; and
a heavy chain and light chain that binds a tumor antigen.

The invention further provides an antibody of the invention or a derivative thereof or a pharmaceutical composition of the invention, for use in the treatment of a subject in need thereof. For the treatment of a subject that has or is at risk of having a tumor it is preferred that the antibody is a bispecific antibody of the invention. Preferably wherein the CD3 binding antibody comprises a heavy/light chain combination that binds a tumor antigen. The bispecific antibody is preferably a CD3/CLEC12A binding antibody.

Provided are CD3/tumor antigen bispecific antibodies and pharmaceutical compositions comprising such bispecific antibodies for use in the treatment of solid or hematological tumors. Preferred solid tumors are of epithelial origin; gynecological cancer such as ovarian and endometrial tumors; prostate cancer, brain cancer or any other solid tumor.

Provided is also a CD3/tumor antigen bispecific antibody of the invention or a derivative thereof or pharmaceutical compositions comprising such bispecific antibody or derivative thereof for use in the treatment of various leukemias and pre-leukemic diseases of myeloid origin but also B cell lymphomas. Diseases that can be treated according to the invention include myeloid leukemias or pre-leukemic diseases such as acute myeloid leukemia (AML), myelodysplastic syndrome (MDS) and chronic myelogenous leukemia (CML), and Hodgkin's lymphomas and most non-Hodgkin's lymphomas. Also B-ALL; T-ALL; mantle cell lymphoma are also preferred targets for treatment with antibody of the invention. Thus the invention provides a bispecific full length IgG antibody according to the invention for use as a pharmaceutical in the treatment of myelodysplastic syndrome (MDS), chronic myelogenous leukemia (CML), multiple myeloma (MM) or preferably acute myeloid leukemia (AML). Also provided is a use of a bispecific IgG antibody according to the invention in the preparation of a medicament for the treatment or prevention of MDS, CML, MM or preferably AML. It is preferred that the tumor antigen is CLEC12A.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred.

Approximately 30.000 patients are diagnosed each year with AML in Europe and US. The majority of these patients are 60 years of age or older. Older age is a major negative determinant of outcome in AML and long term survival (at 5 years) of intensively treated older AML patients is approximately 10%. In almost all patients that have achieved remission upon induction chemotherapy, disease progression is observed within 3 years. Current post remission treatment has shown limited, if any, value in older patients with AML. Therefore, a significant load of residual resistant leukemia remains, and the surviving subpopulation of drug resistant leukemic cells rapidly generates recurrence. Novel types of drugs with entirely different modes of action are needed to target these chemotherapy non responsive AML tumor cells in efforts to induce and sustain complete remissions. Although complete remission (CR) can be achieved with a number of intensive chemotherapy combinations in more than 50% of elderly AML patients and around 80% in younger patients, advancements of response or survival have remained a major investigational challenge. In a recently published network meta-analysis of 65 randomized clinical trials (15.110 patients) in older patients with AML most of the amended investigational induction regimens have similar or even worse efficacy profiles as compared to the conventional 3+7 induction regimen with daunorubicin and cytarabine. This standard treatment of AML is associated with high morbidity and even mortality. The majority of the patients in CR relapse due to remaining leukemic stem cells after chemotherapy. Further dose intensification is limited due to unacceptable toxicity. An urgent need for new treatment modalities preferably with less toxicity is thus emerging especially in elderly patients with AML.

Treatment of chemotherapy unresponsive AML could be achieved by redirecting T cells from the patient's own immune system to AML tumor cells and subsequent tumor target-specific activation of T cells using a bispecific antibody. This process is also known as a so-called "T-cell engaging approach". In this manner, the patients' immune system is strengthened and retargeted to attack and eradicate the AML tumor cells. The present invention provides CD3× CLEC12A bispecific IgG antibodies that efficiently redirects T cells towards the AML tumor cells, thereby inducing AML tumor cell lysis. CD3×CLEC12A bispecific antibodies thus are a targeted therapy with fewer side effects, that specifically eradicates AML blasts and leukemic stem cells in order to improve the prognosis of AML patients. Because CLEC12A is expressed on leukemic stem cells (LSC) and not on normal haematopoietic stem cells, therapy directed against this antigen is anticipated to eradicate the LSC while sparing the normal stem cell. These full length IgG bispecific antibodies are clinically evaluated in relapsed and/or refractory AML patients. The clinical efficacy is analyzed using AML blast reduction in the bone marrow as an objective response criterion. An efficacious bispecific IgG for AML provides a novel therapeutic option for a large patient segment for which there is currently no treatment available. In addition to providing a means to achieve durable remissions, this treatment option also has a curative potential for AML when applied during remission. It most probably will have the greatest impact in situations of Minimal Residual Disease (MRD). The expectancy is that relapse percentage will drop due to the eradication of the MRD. So the impact for the AML patient of this new treatment modality would be a less toxic treatment with a lesser percentage of relapse resulting in an improvement of outcome associated with a better quality of life.

The antibodies 15C3 and 3056 described in the art share the same heavy chain variable region but differ in the light chain variable region. Batch to batch variation in the binding potential of the antibody was observed in batches of antibody 3056. This was not noted for antibody 15C3. As the antibodies differ in the light chain the reason for the difference in behavior would be the different light chain. SDS-page revealed that the 3056 antibody was intact also in batches with less active antibody. 3D-modelling of the variable domains of the antibodies did reveal some changes in the folding of the VH/VL domain between the two antibodies. As these changes might explain the different behavior of the antibodies experiments were designed to render the folding of the VH/VL domain of antibody 3056 more akin 15C3. Unfortunately, this did not explain the differences between the antibodies 15C3 and 3056. Iso-electric focusing (IEF) only revealed slight differences between 15C3 (3055) and 3056 linked to the major band at a high iso-electric point of the antibody. Subsequent analysis using CIEX-HPLC, a chromatographic technique that allows the separation of charge variants, revealed, depending on the batch a very complex retention spectrum with a broad elution profile for antibody 3056, this in contrast to the profile observed for 15C3 (3055). Moreover it was found that the 3056 pattern changed significantly over time, suggesting that the 3056 antibody is inherently instable.

Only when variants were designed wherein the 3056_VH chain was changed at one or two specific positions the behavior changed. The behavior varied between unstable, no binding activity at all to binding without significant batch to batch variability.

The 3056 heavy chain contains an NG deamidation motif in its CDR2 region, WYNGRKQ, which could be involved in the observed charge heterogeneity of the 3056 antibody. In silico modeling of the 15C3 and 3056 Fabs did not reveal a significant difference in the folding of the NG deamidation motif in the HCDR2 region. This argued against an involvement of this motif in the observed instability of the 3056 antibody. Surprisingly however, the changes as indicated in the claims significantly reduced the observed batch to batch variation of antibodies of the invention.

The invention further provides an antibody comprising a variable domain that binds CD3 and a variable domain that binds CLEC12A, wherein the variable domain that binds CLEC12A has a VH comprising the amino acid sequence identified by the numbers 4327 of FIG. 24 with 0-10, preferably 0-5 amino acid insertions, deletions, substitutions, additions or a combination thereof, and the variable domain that binds CD3 has a VH comprising the amino acid sequence identified by the numbers 5192, 5193; 5196; 5197; 5351; 5354; 5356; 5603; 5616; 5626; 5630; 5648; 5661; or 5694 as depicted in FIGS. 12, 25 and 28 with 0-10, preferably 0-5 amino acid insertions, deletions, substitutions, additions or a combination thereof at one or more positions other than the positions 54 and 55. The light chain preferably comprises a variable domain with amino acid as depicted in FIG. 23, preferably 23B.

The invention further provides an antibody comprising a variable domain that binds CD3 and a variable domain that binds CLEC12A, wherein the variable domain that binds CLEC12A has a VH comprising the amino acid sequence identified by the numbers 4327 of FIG. 24 with 0-10, preferably 0-5 amino acid insertions, deletions, substitutions, additions or a combination thereof, and the variable domain that binds CD3 has a VH comprising the amino acid sequence identified by the number 5196 as depicted in FIG. 12 with 0-10, preferably 0-5 amino acid insertions, deletions, substitutions, additions or a combination thereof at one or more positions other than the positions 54 and 55.

The heavy chain of the variable domain that binds CD3 preferably has the amino acid sequence identified the by the numbers 5196; 5197; 5603; 5616; 5626; 5630; 5648; 5661; or 5694 as depicted in FIGS. 12 and 25 with 0-10, preferably 0-5 amino acid insertions, deletions, substitutions, additions or a combination thereof at one or more positions other than the positions 54 and 55. The variable domain that binds CD3 preferably has the amino acid sequence identified the by the number 5196 as depicted in FIG. 12 with 0-10, preferably 0-5 amino acid insertions, deletions, substitutions, additions or a combination thereof at one or more positions other than the positions 54 and 55;

In a preferred embodiment the heavy chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof. For the CD3 heavy chain the indicated amino acid insertions, deletions, substitutions, additions are at positions other than the positions 54 and 55. A combination of an insertion, addition, deletion or substitution is a combination as claimed if aligned sequences do not differ at more than 10, preferably no more than 5 positions. A gap in one of the aligned sequences counts for as many amino acids as skipped in the other sequence.

The invention further provides an antibody comprising a variable domain that binds CD3 and a variable domain that binds CLEC12A, wherein the variable domain that binds CLEC12A has a VH comprising the amino acid sequence identified by the numbers 4327 of FIG. 24, and the variable domain that binds CD3 has a VH comprising the amino acid sequence identified by the numbers 5192, 5193; 5196; 5197; 5351; 5354; 5356; 5603; 5616; 5626; 5630; 5648; 5661; or 5694 as depicted in FIGS. 12, 25 and 28. The heavy chain of the variable domain that binds CD3 preferably has the amino acid sequence identified the by the numbers 5196; 5197; 5603; 5616; 5626; 5630; 5648; 5661; or 5694 as depicted in FIGS. 12 and 25. The variable domain that binds CD3 preferably has the amino acid sequence identified by the number 5196 as depicted in FIG. 12.

BRIEF DESCRIPTION OF THE DRAWINGS

FIG. 6. Alignment of VH MF3056 (of MF3056_VH) versus the VH3-33 germline sequence FIG. 7. Alignment of VH MF3056 versus VH MF3872, MF3873 and MF3905

FIG. 8. Flow cytometry analysis for binding to CD3 on HPB-ALL cells of variants PG3872, PG3873 and PG3905, PG3056 was included as benchmark control FIG. 9. Alignment of VH of MF3056 versus VH of MF3874, MF3878, MF3883, MF3886 and MF3891

FIG. 12 Alignment of VH of MF3056 versus VH of MF5192-5197 VH

FIG. 13. Flow cytometry analysis for binding to CD3 on HPB-ALL cells of variants PG5192-5197, PG3056 was included as benchmark control FIG. 14. IEF analysis of PG5196p06

FIG. 22. Heavy chain variable sequence (VH) of antibody 15C3 described in WO2005/118635. The patent publication describes two variants of the antibody 15C3. Both variants have the same heavy chain variable domain, but this heavy chain variable domain is combined with two different light chain variable domains. Where reference is made herein to antibody 15C3, reference is made to an antibody having the heavy chain variable domain as depicted in this figure in combination with light chain variable domain L2 as indicated in this figure. The Fab product of the 15C3 VH plus L2 light chain is herein further referred to as MF3055.

The antibody PG3056 has the VH as depicted herein in combination with light chain variable region IGKV1-39 as depicted in this figure. The Fab product of the 15C3 VH plus IGKV1-39 light chain is further referred to as MF3056.

FIG. 23. The antibody of the invention preferably has a common light chain. A) The common light chain preferably comprises the amino acid sequence depicted as sequence IGKV1-39 in this figure. B) In a preferred embodiment the common light chain comprises the amino acid sequence depicted as IGKV1-39/jk1 or IGKV1-39/jk5. In a particularly preferred embodiment the common light chain comprises the amino acid sequence of IGKV1-39/jk1 as depicted in this figure.

FIG. 24. Amino acid sequence of the VH region of an anti-CLEC12A binding antibody Fab (MF4327) and the amino acid sequence of the VH region of an anti-tetanus toxoid (TT) binding Fab (MF1337). Together with the amino acid sequence of the common light chain depicted in FIG. 23, these VHs form variable domains of the Fabs MF4327 and MF1337 that bind CLEC12A and tetanus toxoid respectively.

FIG. 25. Examples of the CD3 binding variants of MF5196 are MF5603, MF5616, MF5626, MF5630, MF5648, MF5661 and MF5694, all containing the rearranged human IGKV1-39/IGKJ1 VL region. The amino acid sequence of the VH of the Fabs is indicated.

Figure 26:
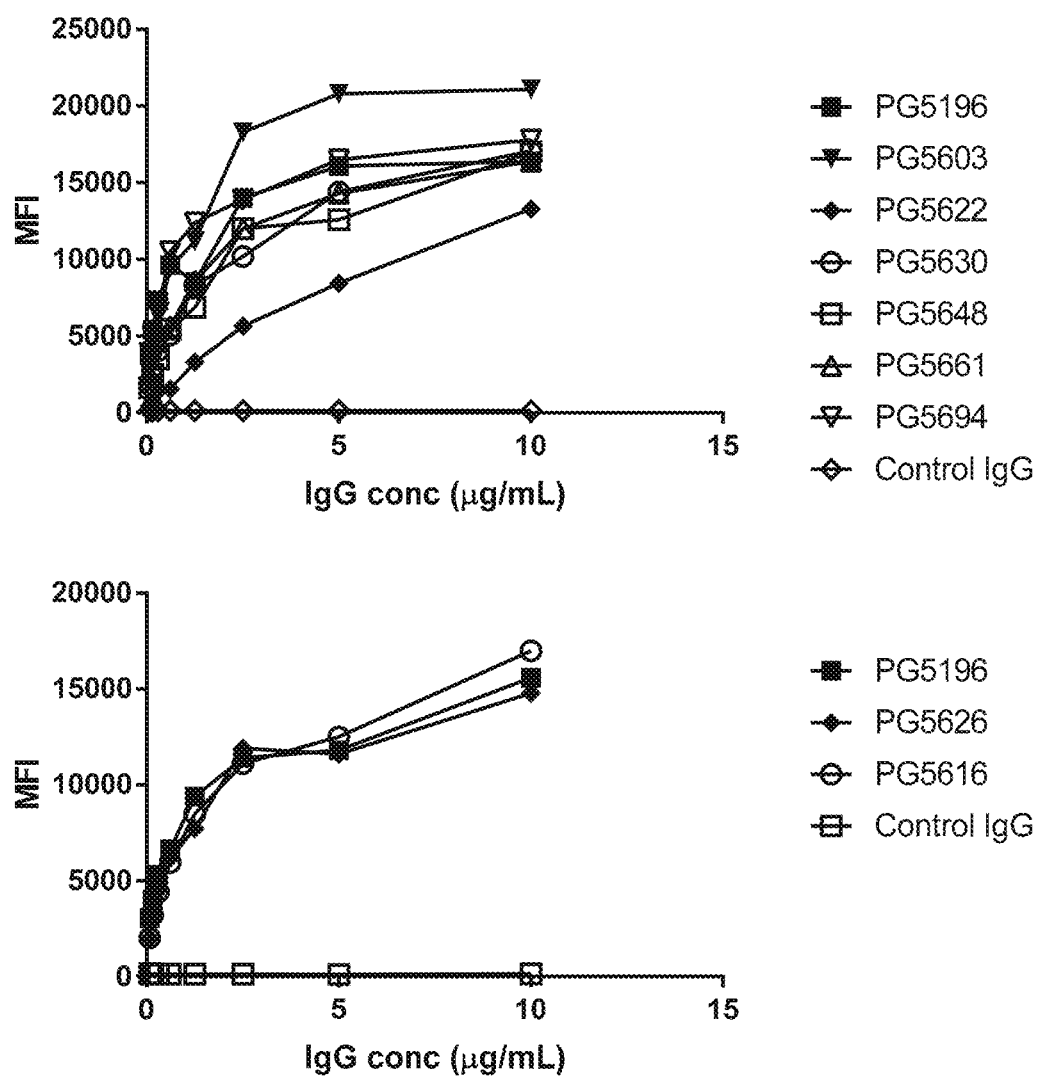

FIG. 26. Binding of antibodies comprising MF5196 VH; MF5603 VH; MF5616 VH; MF5626 VH; MF5630 VH; MF5648 VH; MF5661 VH and MF5694 VH and a common light chain as depicted in FIG. 23B, to membrane-expressed CD3 on HPB-ALL cells, as analyzed by flow cytometry.

Figure 27:
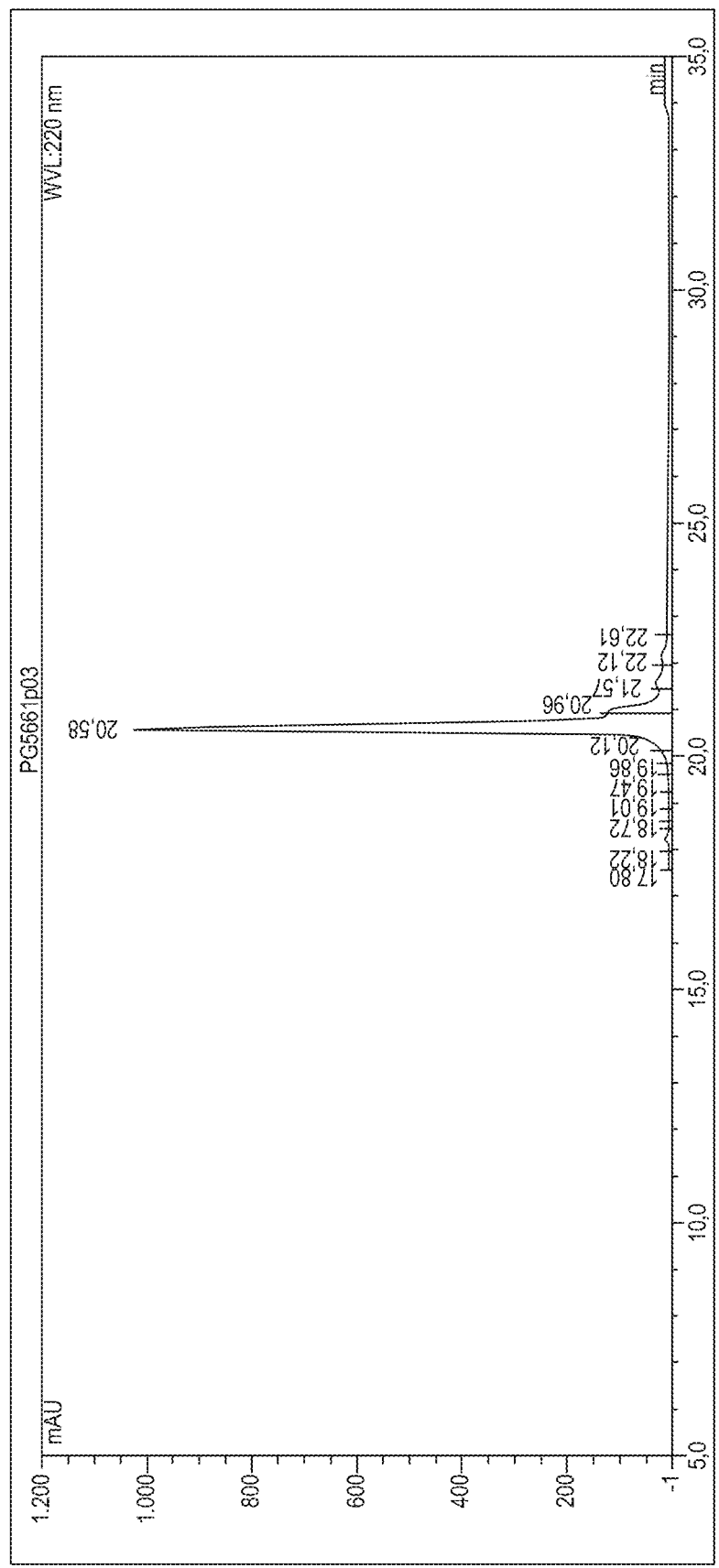

FIG. 27. PG5661 CIEX-HPLC chromatogram.

FIG. 28 CD3 binding Fabs MF5351, MF5354 and MF5356, composed of the rearranged human IGKV1-39/IGKJ1 VL region have the respective VH as depicted.

FIG. 29 PG-format binding to membrane-expressed CD3 on HPB-ALL cells all these examples bound to CD3.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 23, typically 23B. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The variable region of the heavy chains differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example 1

Charge Heterogeneity of 3055 and 3056 mAbs

Iso-electric focusing (IEF) was used to determine the pI and charge heterogeneity of PG3056, a full length IgG1 monoclonal antibody comprising the MF3056 VH paired with the IGVK1-39/JK1 common light chain and PG3055, a full length IgG1 monoclonal antibody comprising the same VH paired with the 15C3 VL2-IGKV1-13 light chain. For this purpose a Focusgel with pI range 6-11 (Webscientific, cat #1006-03) was run on a GE Healthcare Multiphor II electrophoresis unit equipped with a cooling plate that was cooled to 10° C. 10 μg of untreated sample was loaded to the sample slot next to a high pI range marker (GE Healthcare, cat #17047301V). The electrophoresis program consisted of three phases; initial focusing for 10 minutes at 500 V followed by 90 minutes at 1,500 V and finally a focusing phase at 2,000 V for 10 minutes. Consequently the gel was fixed and stained using colloidal coomassie dye (Pierce, cat #24590).

Figure 1:
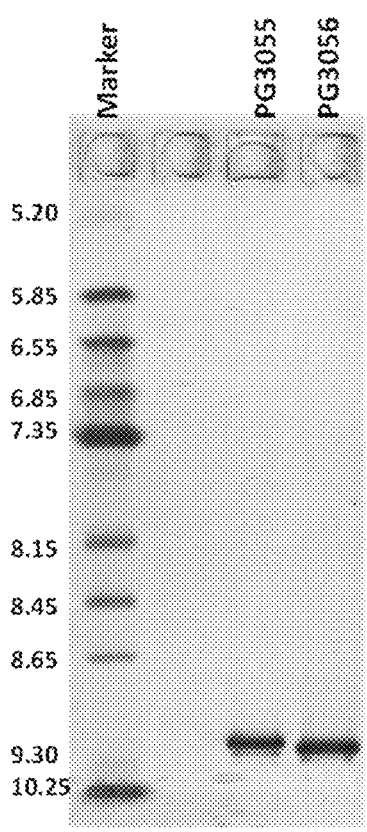
FIG. 1. IEF of PG3055 and PG3056

IEF analysis of PG3056 and PG3055 resulted in the gel shown in FIG. 1. For PG3055 a main band is observed at high pI (~9) with a satellite band at a somewhat higher pI value. PG3056 displayed a similar IEF pattern, however at subtle higher pI values and with a slightly more diffuse main band.

Both IgGs were analyzed using cation exchange chromatography HPLC (CEX-HPLC) to analyze their charge heterogeneity using an orthogonal method. CEX-HPLC was performed at ambient temperature on a Dionex HPLC system equipped with an SP STAT 7 μm column and an UV/Vis detector. 10 μg of sample was injected; a gradient of 25 mM phosphate buffer pH 6.0 with increasing NaCl concentration was used to separate the antibody charge variants. Data were analyzed using Chromeleon software.

Figure 2:
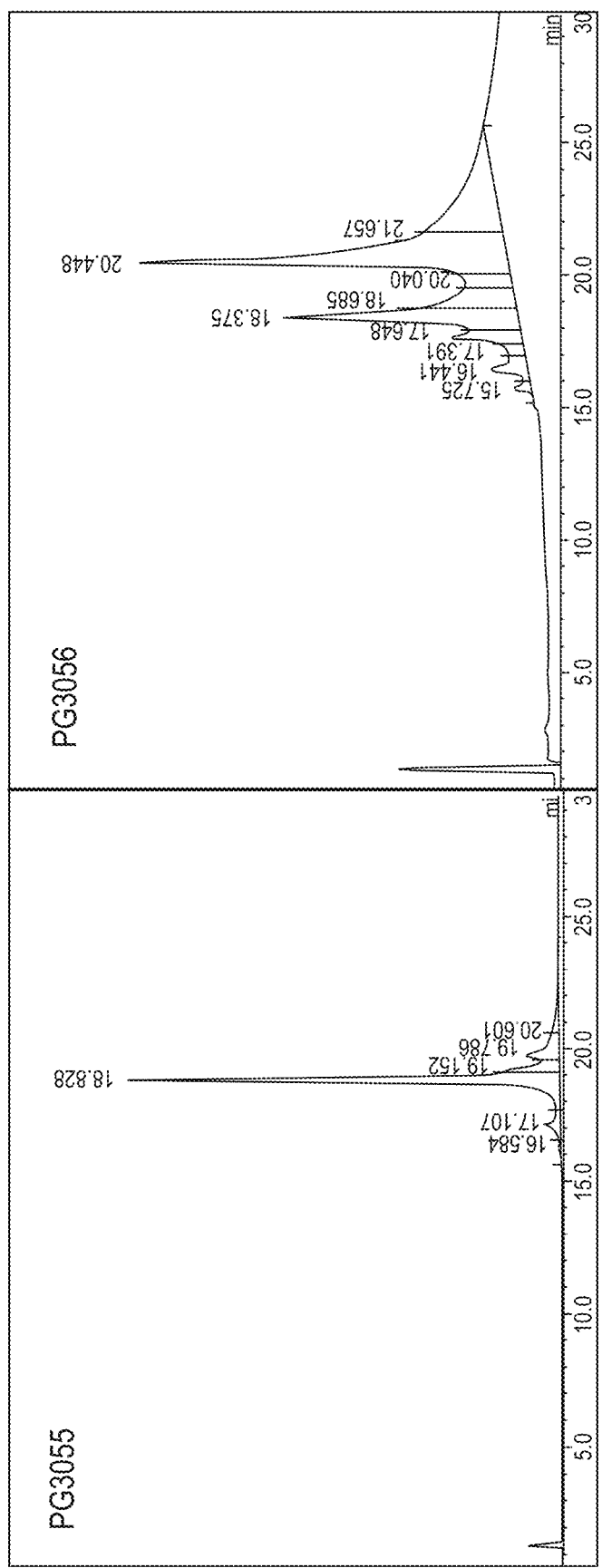
FIG. 2. CEX-HPLC analysis of PG3055 and PG3056

The CEX-HPLC chromatograms of PG3055 and PG3056 are shown in FIG. 2. PG3055 shows a main peak at 18.8 minutes flanked by small peaks representing acidic and basic isoforms of the IgG. Surprisingly, the chromatogram of PG3056 contains multiple peaks over a large time interval; two broad main peaks are visible at 18.4 and 20.4 minutes. The chromatograms show considerably increased charge heterogeneity of the IGVK1-39/JK1 common light chain anti-CD3 antibody (PG3056) when compared to the IgG with the 15C3 VL2-IGKV1-13 light chain (PG3055).

Figure 3:
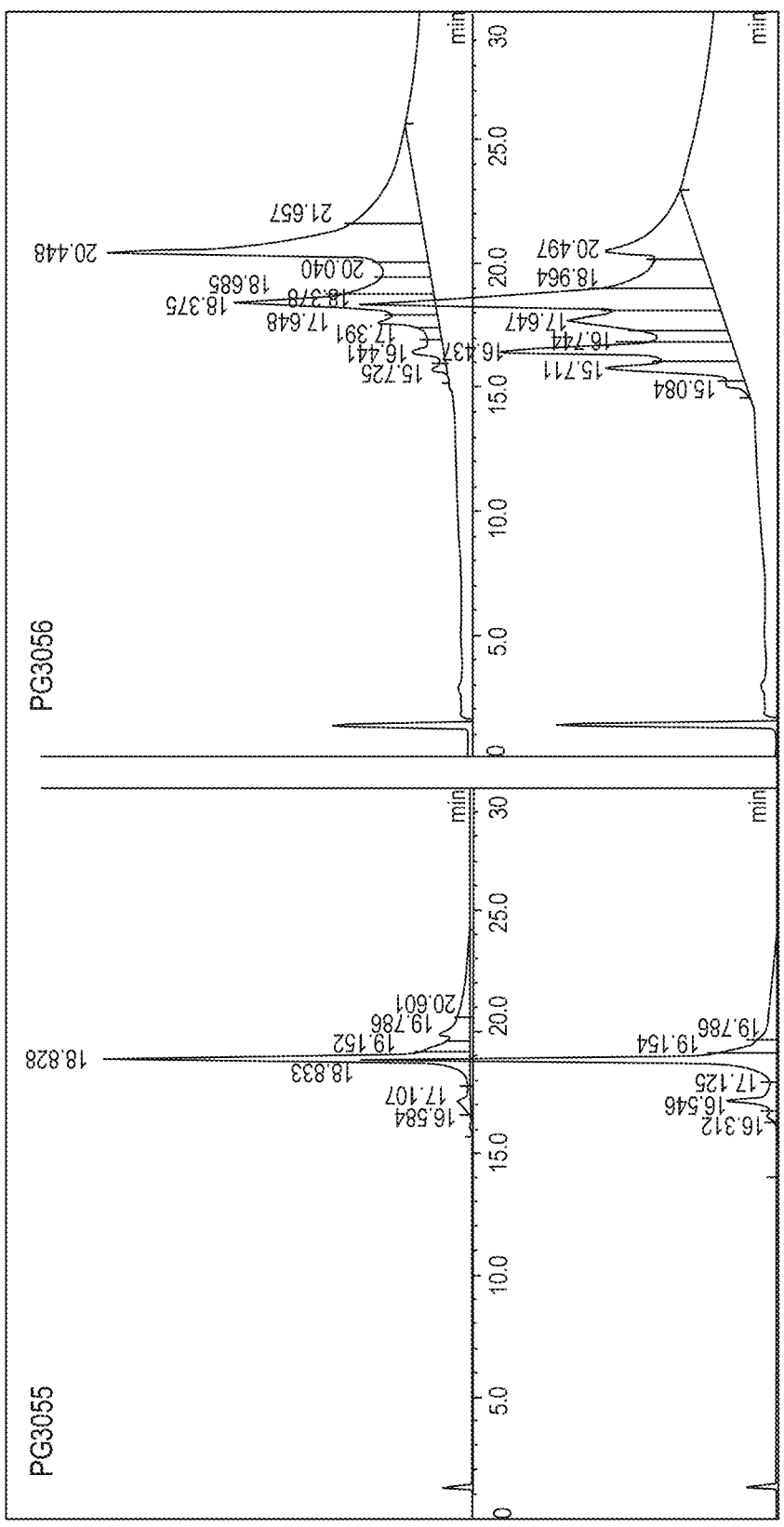
FIG. 3. Batch to batch variability and stability of PG3055 and PG3056 analyzed by CEX-HPLC analysis. Left 3055 batches over time, right 3056 batches over time, with on top samples stored at −80° C., in bottom samples stored at 2-8° C. for >3 months.

CEX-HPLC was also used to assess the batch to batch variability and stability of the anti-CD3 antibodies. Both antibodies were analyzed after they had been stored at 2-8° C. for more than 3 months and after long term storage at −80° C. The overlay of the PG3055 samples (FIG. 3, left) shows that a minor difference is observed between the samples; the relative peak areas of the minor peaks at 17.1 minutes and 19.8 minutes change slightly upon storage at 2-8° C. for a long period of time. The differences observed between the PG3056 samples (FIG. 3 right) are much more substantial. The peak at 20.4 minutes decreases significantly upon storage at 2-8° C. whereas the peak at 18.4 minutes increases to the extent of becoming the main peak of the sample. Other early eluting peaks representing other acidic isoforms of the IgG also show a relative increase in peak area, e.g. the peak at 16.4 minutes. The observed changes in the CEX-HPLC chromatograms after long-time storage at 2-8° C. indicate that the anti-CD3 antibody containing the IGVK1-39/JK1 common light chain is not stable while being stored under these conditions, while the PG3055 antibody containing the 15C3 VL2-IGKV1-13 light chain is much more stable.

Example 2

Influence of PG3056 Antibody Batch to Batch Variation on Antigen Binding

Figure 4:
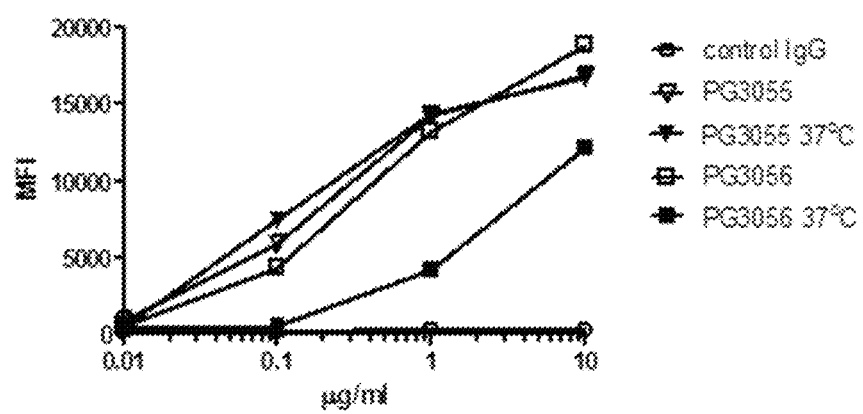
FIG. 4. Flow cytometry analysis for binding of PG3055 and PG3056 to CD3 on purified human T cells upon incubation in IMDM+10% FBS medium at 2-8° C. or 37° C. for 7 days. PG3055 and PG3056: incubated in IMDM+10% FBS medium at 2-8° C. for 7 days. PG3055 37° C. and PG3056 37° C.: PG3055 and PG3056 incubated in IMDM+10% FBS medium at 37° C. for 7 days.

To assess the stability of the anti-CD3 antibodies in the presence of serum the PG3055 and PG3056 antibodies were diluted to 10 μg/mL in IMDM (Invitrogen, Cat #21980-065) supplemented 10% FBS (PAA, Cat #A15-101) and subsequently incubated at 37° C. for seven days. In this analysis an isotype control IgG (PG1207) was included. After seven days the binding of the IgGs to CD3 was assessed by flow cytometry analysis on healthy donor derived, MACS purified T cells. For comparison PG3055 and PG30566 stored in the same medium for seven days at 2-8° C. were included in the flow cytometry analysis. CD3 binding of all antibodies was tested at concentrations 10, 1, 0.1 and 0.01 μg/mL, diluted in IMDM+10% FBS. Bound antibodies were visualized with a goat-anti-human Fc antibody (Southern Biotech, 2043-02), according to FACS procedure as previously described in WO2014/051433 with the deviation that staining was performed IMDM+10% FBS. The data show (FIG. 4) that PG3055 and PG3056 showed similar binding to T cells when incubated at 2-8° C. in the presence of serum. Whereas binding of PG3055 was not affected by a seven day incubation at 37° C. in IMDM+10% FBS (PG3055 vs PG3055 37° C.), the binding of PG3056 to CD3 on T cells was significantly reduced (PG3056 vs PG3056 37° C.).

In conclusion PG3056, the anti-CD3 antibody containing the IGVK1-39/JK1 common light chain, showed strongly reduced binding to CD3 after incubation serum at 37° C. for 7 days. In contrast the PG3055 antibody retained full CD3 binding under the same conditions.

Example 3

What is the Difference Between the PG3055 and PG3056 Antibodies?

Antibodies PG3055 and PG3056 have identical sequences but for the light chain variable region. Apparently the common light chain does not work well in the context of the other amino acid sequences of the antibody and in particular with the heavy chain variable region with which it is in intimate contact. The most obvious way to try and correct the deficiency of the 3056 antibody would be to see if the common light chain can in any way be altered to make it more similar to the light chain in antibody 3055. In addition, the light chain of antibody PG3056 was not selected to be part of the antigen binding site that binds the CD3 molecule. The heavy chain variable region was selected for that purpose. This is another reason to see if the common light chain can be made more akin the light chain in the parent antibody PG3055.

To find out where the PG3055 and PG3056 variable regions differed as a result of the different light chain their Fab regions were modelled. A homology model of the Fab region of PG3056 and PG3055 were built using MODELLER (Sali et al, 1993: J. Mol. Biol. 234, 779-815). A model structure with optimal energy score was selected from the generated ensemble of structures. Side chain optimization and energy minimization algorithms were used to replace the template side chains where these differed from the target sequence. The homology models of the 3055 and 3056 Fabs were visually inspected using Yasara (http://www.yasara.org). The overlay of the models for PG3055 and PG3056 (FIG. 5, right picture) shows that the sequence differences in the light chain only cause a few structural changes; the orientation of some parts of the light chain with respect to the heavy chain is changed to some extent between the two IgGs. The changed parts could inherently be less stable and be the root cause for the observed stability differences. Alternatively, the changed parts could be more or less susceptible to different heterogeneity inducing processes. Various processes, known and unknown, can be the cause of the observed features for the PG3056 antibody. Enzymatic and non-enzymatic modifications include the formation of disulfide bonds, glycosylation, N-terminal glutamine cyclization, C-terminal lysine processing, deamidation, oxidation, glycation, and peptide bond cleavage are among the processes that can cause heterogeneity (Liu et al. Journal of Pharmaceutical Sciences, Vol. 97, 2426-2447 (2008)). Depending on the type of modification, the heterogeneity of monoclonal antibodies can be introduced by intracellular processes, extracellular processes for instance taking place in serum, ascites, and/or cell culture medium. Heterogeneity can also be introduced by incubation with buffers, during the purification process, storage, under different stressed conditions such as elevated temperature or exposure to intense light.

The modelling did not pinpoint to a particular amino acid or region to focus the mutation efforts of the variable region of PG3056 on. The observed differences between the homology models of PG3055 and PG3056 where minor.

In the present invention it was found that there is no need to change the amino acid sequence of the light chain of the PG3056 antibody. Adaptation of the heavy chain can produce an antibody with good binding properties, good stability and good uniformity even when the heavy chain is present in a variable region with the common light chain. As will be exemplified in more detail herein below it was surprisingly found that specific changes in the CDR2 region of the heavy chain are tolerated with respect to binding and provide the antibody with the desired stability and uniformity.

Figure 5:
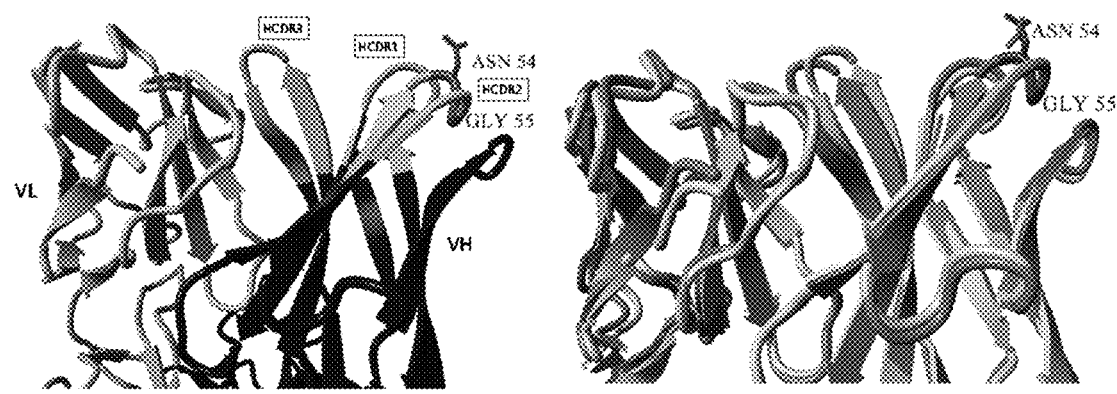
FIG. 5. Left: Homology model of PG3056 Fab zoomed in on variable domains, VL in light gray, VH in black, HCDR1-3 loops in light gray. Residues Asn54 and Gly55 that form the deamidation motif in HCDR2 are indicated. Right: Overlay of homology models of PG3055 (light gray) and PG3056 (dark gray) Fabs.

The changes result in a change in an NG deamination motif in the CDR2 region of the heavy chain. The HCDR2 region of both PG3055 and PG3056 contain Asn54 and Gly55 residues. The residues are surface exposed in both antibodies as is shown in FIG. 5. The structural position and surface exposure are very similar in both molecules, with a slightly different orientation for the asparagine side chain. Considering that the motif is surface exposed in both antibodies and thus easily accessible to the environment and that there appears to be no significant difference in the folding of the HCDR2 NG motif in PG3055 versus P3056, it would be considered unlikely that enhanced deamidation of Asn54 in PG3056 would be the root cause for the observed binding variation of the different PG3056 batches.

Example 4

Generation and Characterization of PG3056 Variants

Analytical characterization of PG3056 by CIEX-HPLC showed that the IgG is highly heterogeneous. As this heterogeneity could obstruct CIEX-HPLC based purification of the CD3×CLEC12A bispecific IgG we aimed to improve the CIEX-HPLC profile of the MF3056 Fab. The heavy chain variable region of MF3056 contains several residues and/or motifs that might contribute to the PG3056 heterogeneity. These are the C-terminal lysine residue, an NG asparagine deamidation motif in the HCDR2 and an acid labile DP motif in the HCDR3 (see FIG. 6 for an alignment of the MF3056_VH versus the VH 3-33 germline sequence).

Although the in silico modeling did not pinpoint at all to the HCDR2 NG motif as probable cause for the observed heterogeneity, it was attempted to identify variants of the VH of MF3056 that lack this post-translational modification motif, and which in parallel might display an improved CIEX-HPLC retention profile as well as improved stability. To this end the following variants of the VH of MF3056 were generated and tested: MF3872, MF3873 and MF3905 (FIG. 7).

These Fabs containing these VH variants and the common light chain (MF3872, MF3873 and MF3905) were expressed as full length monoclonal IgG (PG3872, PG3873 and PG3905) and tested for binding to membrane-expressed CD3 on HPB-ALL cells by flow cytometry (according to the FACS procedure as previously described in WO2014/051433). The following results were obtained (FIG. 8):

These results show that the variants PG3873 and PG3905 completely lost CD3 binding, whereas very low binding to CD3 was retained for variant PG3872.

As an alternative approach to obtain improved variants with reduced heterogeneity and reduced immunogenicity, the VH of MF3056 was germlined towards the VH3-33 sequence at several residues by making individual or combined amino acid substitutions. The following variants of the MF3056_VH were generated: MF3874_VH, MF3878_VH, MF3883_VH, MF3886_VH and MF3891_VH (FIG. 9).

Figure 10:
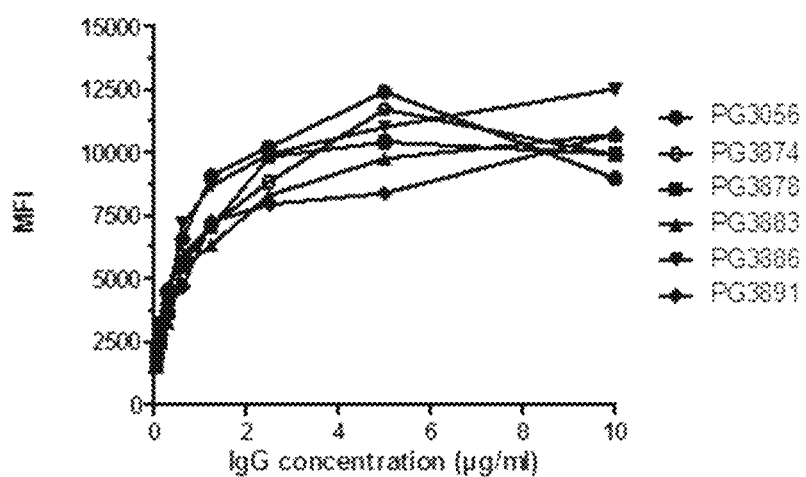
FIG. 10. Flow cytometry analysis for binding to CD3 on HPB-ALL cells of variants PG3874, PG3878, PG3883, PG3886 and PG3891, PG3056 was included as benchmark control.

Again, Fabs containing these VH variants and the common light chain (MF3874_VH, MF3878_VH, MF3883_VH, MF3886_VH and MF3891_VH) were expressed as full length monoclonal IgG (PG3874, PG3878, PG3883, PG3886 and PG3891) and tested for CD3 binding as described above. The following results were obtained (FIG. 10):

As shown in FIG. 10, all individual (PG3874 (Q6E), PG3878(V23A), PG3883 (A50V), PG3886 (T97A)) and combined (PG3891 (Q6E/V23A/T97M germlined variants retained full CD3 binding capacity. Subsequently, PG3891 was analyzed by CIEX-HPLC (as described in example 1) to assess whether the germlining had resulted in reduced heterogeneity.

Figure 11:
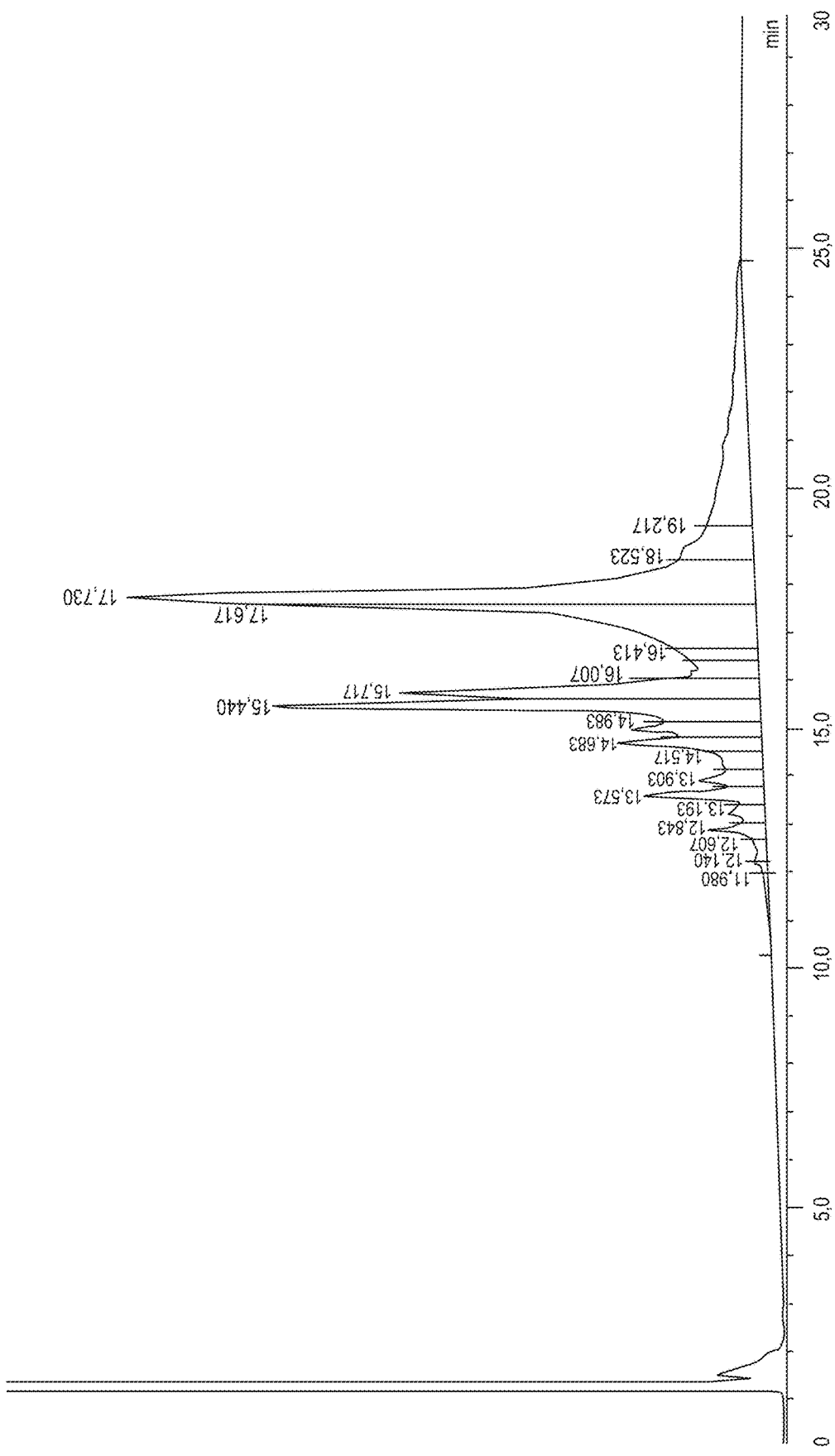
FIG. 11. CEX-HPLC analysis of PG3891

As shown in FIG. 11, the CIEX-HPLC profile of PG3891 still displayed significant charge heterogeneity. Similar CIEX-HPLC profiles were obtained for the individual germlining variants (data not shown).

In a next attempt to reduce the charge heterogeneity of PG3056, MF3056_VH variants lacking the HCDR2 NG motif were generated (FIG. 12).

Fabs containing these VH variants and the common light chain (MF5192-5197_VH) were generated and expressed as full length monoclonal IgG (PG numbers) and tested for binding to membrane-expressed CD3 on HPB-ALL cells by flow cytometry as described above. This analysis (FIG. 13) showed that PG5196 ($N_{54}G_{55}$ into $N_{54}A_{55}$ substitution) retained CD3 binding comparable to PG3056, whereas all other tested MF3056 variants showed significantly reduced (PG5192, PG5193 or PG5197) or no CD3 binding (PG5194 and PG5195).

Figure 14:
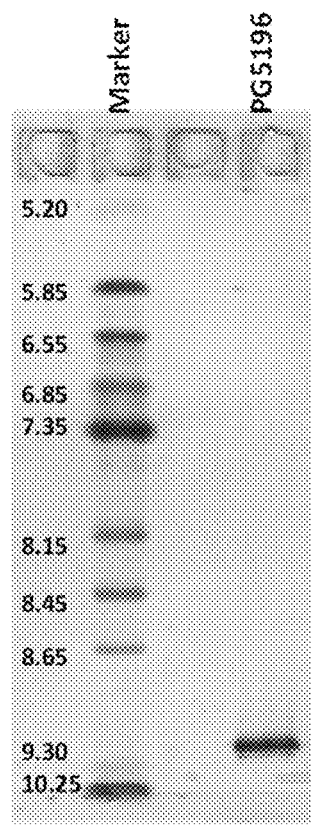

To assess the charge heterogeneity of the PG5196 mAb, isoelectric focusing was performed as described in example 1. After staining of the gel, a narrow band at high pI is observed for PG5196 with a minor satellite band at a somewhat higher pI value (see FIG. 14).

Figure 15:
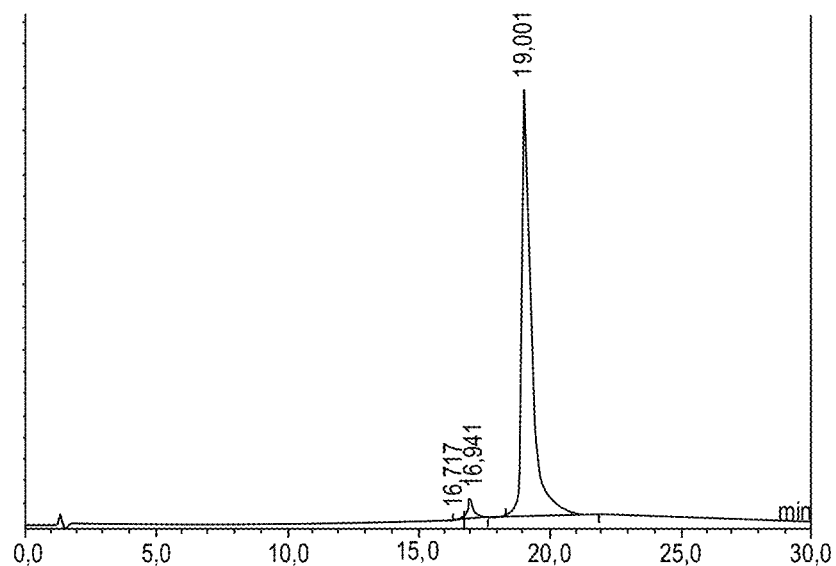
FIG. 15. CEX-HPLC chromatogram of PG5196

To assess the charge heterogeneity of PG5196 in further detail, CIEX-HPLC was performed according to the procedure described in example 1, the resulting chromatogram is shown in FIG. 15. The chromatogram shows a main peak with a retention time of 19 minutes, preceded by a small peak at 16.9 minutes. Surprisingly, these data demonstrate that PG5196 displays a significantly improved charge heterogeneity profile when compared to PG3056.

Example 5

Generation of Additional Variants of PG5196 Using Phage Display Selections

Based on the MF5196 VH, phage display libraries were designed with the aim to obtain additional CD3 binding Fabs with similarly reduced charge heterogeneity. Phage display libraries were generated which contained the rearranged human IGKV1-39/IGKJ1 VL region (De Kruif et al. Biotechnol Bioeng. 2010 (106)741-50), and a collection of MF5196-based VH regions incorporating amino acid substitutions that potentially could improve the VH/VL interface. The specific substitutions and the allowed alternative amino acids per position are indicated in Table 1. Per mutated position all the indicated substitutions as well as the original amino acid were introduced in an equal ratio.

TABLE 1

| Amino-acid and position in MF5196_VH | Region | Substitutions introduced per position |
| --- | --- | --- |
| H35 | FR2 | FYASN |
| A50 | FR2 | ILFYNRQSK |
| N54 | HCDR2 | H |
| A55 | HCDR2 | GTN |
| D59 | HCDR2 | LIVFYRANEHST |
| A61 | FR3 | FNIHQLRYE STDKV |
| Y102 | HCDR3 | ARNDCEQGHILKMFPSTWV |
| N103 | HCDR3 | ARDCEQGHILKMFPSTWYV |
| W104 | HCDR3 | MFYHLIV |
| F105 | HCDR3 | WMYHLIV |

Bacteriophages from these phage display libraries were selected in one or two rounds using HBP-ALL cells and/or recombinant human CD3δε-Fc protein using procedures known to a person skilled in the art. Binding phages were chemically eluted, and used to re-infect bacteria. After picking a number of surviving bacterial colonies, phages were rescued and were screened for binding to cell surface expressed CD3/TCR complexes by flow cytometry. Colony PCR for was performed for all phages that showed CD3 binding to amplify and sequence the VH regions.

Analysis of the VH genes revealed which substitution variants retained CD3 binding. The selected MF5196_VH variants had the following substitutions: A50 into QSYL, D59 into LIVFRANEHST, A61 into NIHQLRYESTDKV and/or F105 into MY (Table 2). In contrast, the in Table 1 listed substitutions at H35, Y102, N103, and W104 were not allowed as all selected CD3 binding variants retained the original amino acid at positions 35, 102, 103 and 104. This shows that the H35, Y102, N103, and W104 residues are critical amino acids for CD3 binding.

Examples of the CD3 binding variants of MF5196_VH are MF5603_VH, MF5616_VH, MF5626_VH, MF5630_VH, MF5648_VH, MF5661_VH and MF5694_VH, all in combination with the rearranged human IGKV1-39/IGKJ1 VL region. The VH sequences of these MFs are listed in FIG. 25. Testing of these MF variants in monospecific IgG format for binding to membrane-expressed CD3 on HPB-ALL cells, by flow cytometry as described above, showed that all these examples bound to CD3 (FIG. 26). As an example of their inherent stability, PG5661 was analyzed by CIEX-HPLC was performed according to the procedure described in example 1, the resulting chromatogram is shown in FIG. 27. The chromatogram shows a main peak with a retention time of ~20 minutes, similar to the profile as shown for PG5196.

TABLE 2

| Amino-acid and position in MF5196_VH | Substitutions introduced in MF5196 | CD3 binding MF5196 variants found with substitutions |
| --- | --- | --- |
| A50 | ILFYNRQSK | QSYL |
| D59 | LIVFYRANEHST | LIVFRANEHST |
| A61 | FNIHQLRYESTDKV | NIHQLRYESTDKV |
| F105 | WMYHLIV | MY |

Example 5B

Based on the MF5196 VH, phage display libraries were designed with the aim to obtain additional stable CD3 binding Fabs. Phage display libraries were generated which contained the rearranged human IGKV1-39/IGKJ1 VL region (De Kruif et al. Biotechnol Bioeng. 2010 (106)741-50), and a collection of VH3-33 variants to which the heavy chain CDR3 region of MF5196 was fused.

Bacteriophages from these phage display libraries were selected in one or two rounds using HBP-ALL cells and/or recombinant human CD3δε-Fc protein using procedures known to a person skilled in the art. Binding phages were chemically eluted, and used to re-infect bacteria. After picking a number of surviving bacterial colonies, phages were rescued and were screened for binding to cell surface expressed CD3/TCR complexes by flow cytometry. Colony PCR for was performed for all phages that showed CD3 binding to amplify and sequence the VH regions.

Examples of the resulting additional CD3 binding variants of MF5196_VH are MF5351_VH, MF5354_VH and MF5356_VH (listed in FIG. 28), all in combination with the rearranged human IGKV1-39/IGKJ1 VL region.

Testing of these MF variants in monospecific IgG format for binding to membrane-expressed CD3 on HPB-ALL cells, by flow cytometry as described above, showed that all these examples bound to CD3 (FIG. 29).

Example 6

Figure 16:
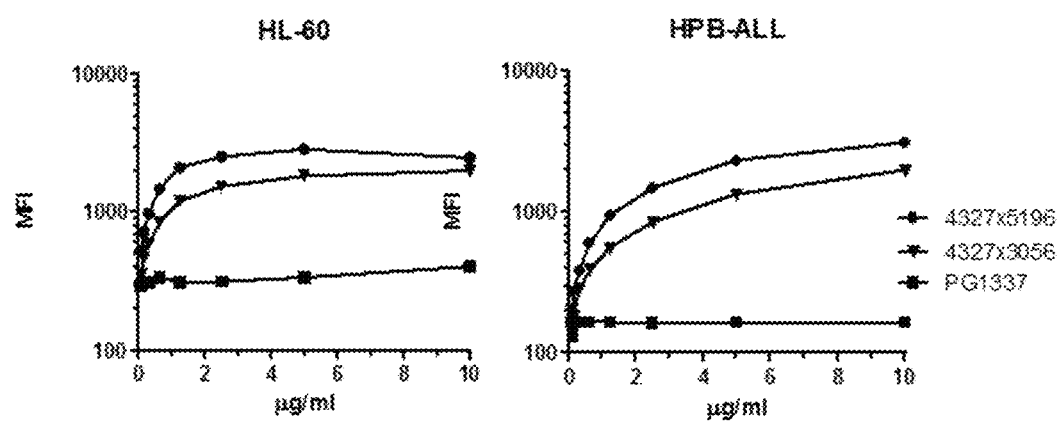
FIG. 16. Binding of 5196×4327 DM-Fc bsAb to membrane expressed CD3 (HPB-ALL) and CLEC12A (HL-60)

Functional Characterization of the MF5196 Fab in the CD3×CLEC12A Bispecific IgG Format To examine the functional activity of the MF5196 Fab, this CD3 Fab and the MF3056 CD3 Fab were expressed together with the CLEC12A Fab MF4327 as the fixed arm. The CD3×CLEC12A bispecific IgGs were expressed in the full length bispecific IgG format as described in WO2014/051433, including the lower hinge/CH2 engineering at positions 235-236 (referred to as DM-Fc, CH2 double mutation in Fc region). Like MF3056 and MF5196, the MF4327 Fab uses the human IGKV1-39/IGKJ1 light chain. The MF4327 Fab sequence is given in patent application WO2014/051433. First, binding of the 5196×4327 DM-Fc bsAb to CD3 and CLEC12A was demonstrated by flow cytometry using CD3+ HPB-ALL cells and CLEC12A+HL-60 cells (according to procedures as previously described in WO2014/051433). The 3056×4327 DM-Fc bsAb was included as reference and an irrelevant IgG1 isotype control, PG1337, was included as control (FIG. 16). Both CD3× CLEC12A DM-Fc bsAbs bound membrane expressed CD3 and HPB-ALL with slightly improved binding for 5196× 4327 DM-Fc bsAb.

Figure 17:
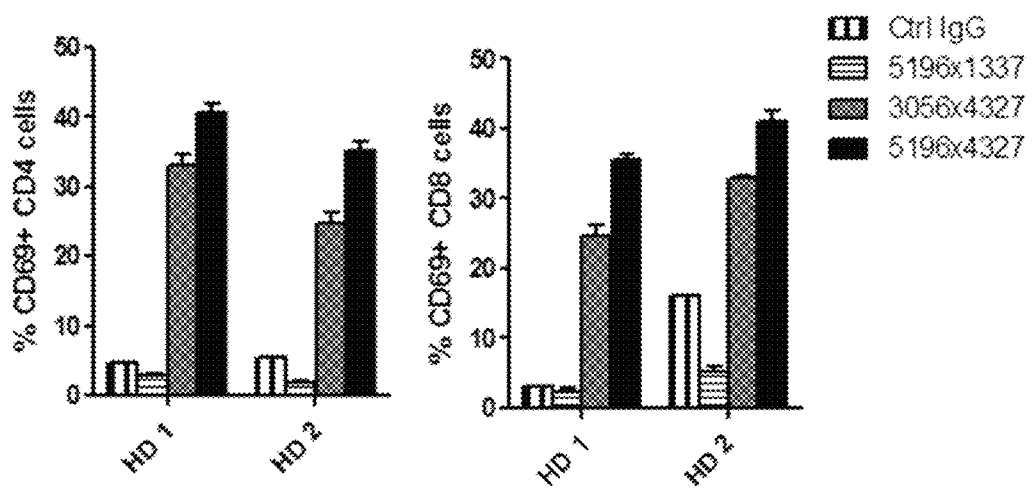
FIG. 17. 5196×4327 DM-Fc bsAb retained CLEC12A-specific activation of CD4 and CD8 T cells reflected by up regulation of early activation marker CD69. The bsAb and control IgGs were tested at 1000 ng/mL. T cell activation flow cytometry data are expressed as the percentage of CD69-positive cells within the CD4+ or CD8+ T-cell populations. HD1 and HD2 reflect two different experiments using T cells obtained from different healthy donors FIG. 18. 5196×4327 induced antigen mediated target cell lysis FIG. 19. Sensorgrams showing on- and off-rates of CD3δε-Fc (A) and CLEC12A protein (B) to immobilized 5196×4327 DM-Fc bsAb. Sensorgrams show the response (amount of protein bound to the chip, in artificial units) as a function of the time (in seconds). Both panels show the sensorgrams obtained using a concentration range of antigen (in colour) and the respective curve fittings performed using the BIAevaluation software (in black).

Next, the functional activity of 5196×4327 CD3× CLEC12A DM-Fc bsAb was tested. First, the T-cell stimulatory capacity was investigated with healthy donor resting T-cells. Purified resting T cells were obtained according the procedure described in patent WO2014/051433. Purified resting T-cells were subsequently incubated with cells from the leukemia-derived HL-60 cell line in 10% human serum (HS) at an effector: target cell ratio of 5:1 for two days as described in WO2014/051433. The 3056×4327 DM-Fc bsAb was included as reference. As negative control benchmark IgGs an isotype control IgG (control IgG) and the 5196×1337 DM-Fc bsAb were included. The 5196×1337 DM-Fc bsAb binds CD3 with one arm (MF5196) and binds tetanus toxoid (TT) with second arm (MF1337) and is included to examine potential off-target induced activity by MF5196. The bsAb and control IgGs were tested at 1,000 ng/mL. T cell activation data are expressed as the percentage of CD69-positive cells within the CD4-positive or CD8-positive T-cell population (FIG. 17). The 5196×4327 DM-Fc bsAb induced activation of CD4 and CD8 T cells as reflected by the upregulation of CD69 early activation marker. Also the 3056×4327 DM-Fc bsAb induced upregulation of CD69 on CD4 and CD8 T cells, however to a less extent compared to the 5196×4327 DM-Fc bsAb. The observed upregulation of CD69 on both T cell subsets was CLEC12A antigen specific as the 5196×1337 DM-Fc bsAb did not induce upregulation of CD69.

This analysis showed that the 5196×4327 DM-Fc bsAb had the capacity to induce antigen specific activation of CD4 and CD8 T cells, slightly better than 3056×4327 DM-Fc bsAb (FIG. 17). The 5196×4327 DM-Fc bsAb induced T cell activation was CLEC12A specific as the control 5196× 1337 DM-Fc bsAb induced no T cell activation. Taken together, this shows that the HCDR2 N into A amino acid substitution, resulting in CD3 binding MF5196 Fab, fully retained CLEC12A-specific T cell activation.

To investigate whether the extent of T-cell activation by the 5196×4327 versus 3056×4327 CD3×CLEC12A DM-Fc bsAb was sufficient to induce target cell lysis, the HL-60 cells were labeled with carboxyfluorescein diacetate succimidyl ester (CFSE) and co-cultured with T-cells from healthy donor at effector:target cell ratio of 5:1 in presence of 10% HS. The 5196×1337 CD3×TT DM-Fc bsAb was included to examine potential off-target lysis. The bispecific IgGs were tested in a 4-fold dilution range starting at 1,000 ng/ml. After two days, the surviving CFSE-positive HL-60 cells were quantified by flow cytometry. Results were expressed as the percentage of specific lysis related to the PBS control condition (FIG. 18).

This analysis showed that the 5196×4327 DM-Fc bsAb had fully retained the capacity to induce CLEC12A antigen specific target cell lysis. Surprisingly, the potency of 5196× 4327 DM-Fc was significantly better than 3056×4327 DM-Fc bsAb.

In conclusion, this example showed that MF5196 Fab is functional as the 5196×4327 CD3×CLEC12A DM-Fc bsAb efficiently induced CLEC12A antigen specific T cell activation and lysis of CLEC12A+HL-60 cells. Moreover this example showed that the 5196×4327 DM-Fc bsAb has an improved potency when compared to the 3056×4327 DM-Fc bsAb.

Example 7

Affinity of the Anti-CD3 and Anti-CLEC12A Arms of 5196×4327 DM-Fc bsAb

The affinities of the MF5196 CD3 and MF4327 CLEC12A Fabs for their targets were measured by surface plasmon resonance (SPR) technology using a BIAcore T100. An anti-human IgG mouse monoclonal antibody (Becton and Dickinson, cat. Nr. 555784) was coupled the surfaces of a CM5 sensor chip using free amine chemistry (NHS/EDC). Then the 5196×4327 DM-Fc bsAb was captured onto this sensor surface. Subsequently the recombinant purified antigens human CLEC12A (Sino Biological Inc, cat. Nr. 11896-H07H) and human CD3δε-Fc protein were run over the sensor surface in a concentration range to measure on- and off-rates. After each cycle, the sensor surface was regenerated by a pulse of HCl and 5196×4327 DM-Fc bsAb was captured again. From the obtained sensorgrams, on- and off-rates were determined using the BIAevaluation software.

These data (FIG. 19) showed that 5196×4327 DM-Fc bsAb had an affinity for 3 nM for human CLEC12A and an affinity of 177 nM for CD3. This showed that affinity of the CLEC12A arm was ~60 fold higher than the affinity of the human CD3 binding arm in the 5196×4327 DM-Fc bsAb.

TABLE 3 on- and off-rates and affinity values for binding to human CD3 and human CLEC12A. The value is the average of three measurements. KD: affinity (equilibrium dissociation) constant.

| Antigen | KD (M) |
|---|---|
| CLEC12A | $3 \times 10^{-9}$ |
| CD3δε-Fc | $177 \times 10^{-9}$ |

Example 8

Efficacy of 5196×4327 DM-Fc bsAb to Induce AML Blast Lysis in Primary AML Patient Samples It was shown in example 6 that the 5196×4327 DM-Fc bsAb potently induces HL-60 target cell lysis by healthy donor derived T cells. In patent WO2014/051433 the inventors showed that a CD3×CLEC12A DM-Fc bsAb had the capacity to induce lysis of AML blast by autologous AML patient derived T cells at effector to target ratio 5:1. Here, the efficacy of a CD3×CLEC12A DM-Fc bsAb, more specific of 5196×4327 CD3×CLEC12A DM-Fc bsAb, to induce lysis of AML blasts in primary AML samples with low effector to target, T cell to AML blast, ratios was examined.

AML patient samples taken at diagnosis (from AML FAB classifications M1, M2, M4, M4/M5, Table 4) were thawed and characterized for the fraction of T cells and AML blasts by flow cytometric analysis for CD4, CD8, CD14, CD33, CD34, CD45 and 7AAD. AML samples analysed had an effector to target ratio ranging from 1:7-1:40.

Subsequently, the primary AML patient bone marrow samples were cultured in IMDM medium supplemented with 10% normal HS plus 20 ng/mL IL-15 (Miltenyi, #130-095-766), 2.5 ng/mL GM-CSF (Immunotools, #11343125), 12.5 ng/mL G-CSF (described in Norde et al., 2009), 6.25 ng/mL IL-3 (Immunotools, #11340035), 3.0 ng/mL SCF (Immunotools, #11343325) and 2.5 ng/mL Flt3L (Immunotools, #311340035). The conditions tested included PBS, isotype control Ab WT-Fc, 5196×4327 DM-Fc bsAb, 5196×1337 DM-Fc bsAb and positive control CD3 WT-Fc Ab (all antibodies at 1,000 ng/mL). After seven days of culture T cell expansion and AML blast killing was determined by flow cytometric analysis using the same markers as used on day 0. Results were expressed as fold T cell expansion or frequency of AML blast lysis relative to PBS condition.

Figure 20:
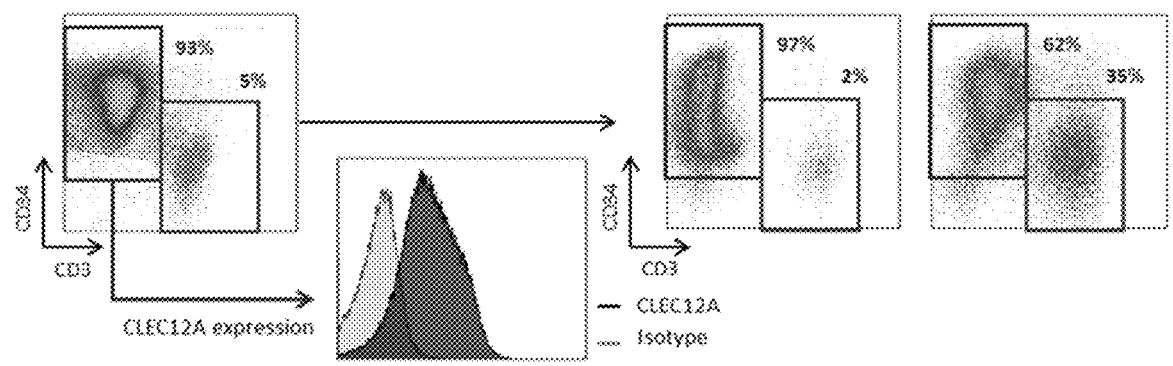
FIG. 20. Primary AML patient sample was phenotyped for CLEC12A expression and the fraction of T cells and AML blasts by flow cytometry analysis at start (day=0) of the co-culture. After days 7 of co-culture with 5196×4327 DM-Fc bsAb or isotype control the fraction and the total number of T cells and AML blasts were quantified by flow cytometry analysis FIG. 21. DSC analysis as described in example 9.

These data demonstrated (Table 4 and FIG. 20) that 5196×4327 DM-Fc bsAb efficiently induced T cell expansion (5-30-fold T cell expansion) after 7 days. More importantly, these data showed that the 5196×4327 DM-Fc bsAb efficiently induced lysis (26-88%) of patient's AML tumor cells in 5/5 tested primary AML patient samples, even in AML samples with very low effector to target ratios.

TABLE 4

| Patient# | E:T ratio at day 0 | AML FAB classification | % Blast killing (after 7 days) | Fold T cell expansion (after 7 days) |
|---|---|---|---|---|
| #1 | 1:21 | M4/M5 | 26% | 30 |
| #2 | 1:10 | M4 | 44% | 8 |
| #3 | 1:7 | M2 | 88% | 4 |
| #4 | 1:39 | M4/M5 | 65% | 6 |
| #5 | 1:40 | M1 | 83% | 6 |

The efficacy of the 5196×4327 DM-Fc bsAb to induce T cell proliferation and AML blast lysis was analyzed in additional AML patient samples taken at diagnosis.

AML patient samples taken at diagnosis (from AML FAB classifications M1, M2, M4, M4/M5, Table 5) were thawed and characterized for the fraction of T cells and AML blasts by flow cytometric analysis for CD4, CD8, CD14, CD33, CD34, CD45 and 7AAD. AML samples analysed had an effector to target ratio ranging from 1:3-1:97. Subsequently, the primary AML patient samples were cultured as described above in example 8. The conditions tested included PBS, isotype control Ab WT-Fc, 5196×4327 DM-Fc bsAb, 5196×1337 DM-Fc bsAb and positive control CD3 WT-Fc Ab (all antibodies at 200 ng/mL). After seven and ten days of culture T cell expansion and AML blast killing was determined by flow cytometric analysis using the same markers as used on day 0. Results were expressed as fold T cell expansion or frequency of AML blast lysis relative to PBS condition.

These data demonstrated (Table 5) that 5196×4327 DM-Fc bsAb efficiently induced T cell expansion (7-226-fold T cell expansion) after 10 days. More importantly, these data showed that the 5196×4327 DM-Fc bsAb efficiently induced lysis (38-99%) of patient's AML tumor cells in 6/8 tested primary AML patient samples, even in AML samples with very low effector to target ratios of 1:45-1:97.

TABLE 5

| Patient # | E:T ratio at day 0 | AML FAB classification | AML risk classification | % Blast killing (after 10 days) | Fold T cell expansion (after 10 days) |
|---|---|---|---|---|---|
| #6 | 1:45 | M1 | Good | 95% | 20 |
| #7 | 1:3 | M2 | Good | 99% | 39 |
| #8 | 1:17 | M2 | Poor | 87% | 226 |
| #9 | 1:94 | M4 | Poor | 0% | 7 |
| #10 | 1:46 | M4/M5 | Poor | 38% | 23 |
| #11 | 1:97 | M4/M5 | Poor | 39% | 55 |
| #12 | 1:31 | M4/M5 | Intermediate | 0% | 9 |
| #13 | 1:15 | M4/M5 | Intermediate | 67% | 130 |

Example 9

Differential scanning calorimetry (DSC) was used to measure the thermo stability of the domains of the IgGs described here. DSC experiments were performed on a MicroCal VP-DSC using Origin v7.0 (VPViewer and VPAnalyzer) software. The antibodies were first dialyzed against a 10 mM phosphate, 150 mM NaCl buffer at pH 6.5. IgG samples were analyzed at a protein concentration of 0.25 mg/mL as determined by UV absorption, the dialysis buffer was used as reference sample. Scans ran from 50° C.-95° C. with a scan rate of 1° C./min and were analyzed using GraphPad Prism 5 and Microsoft Excel 2010 software.

Figure 21:
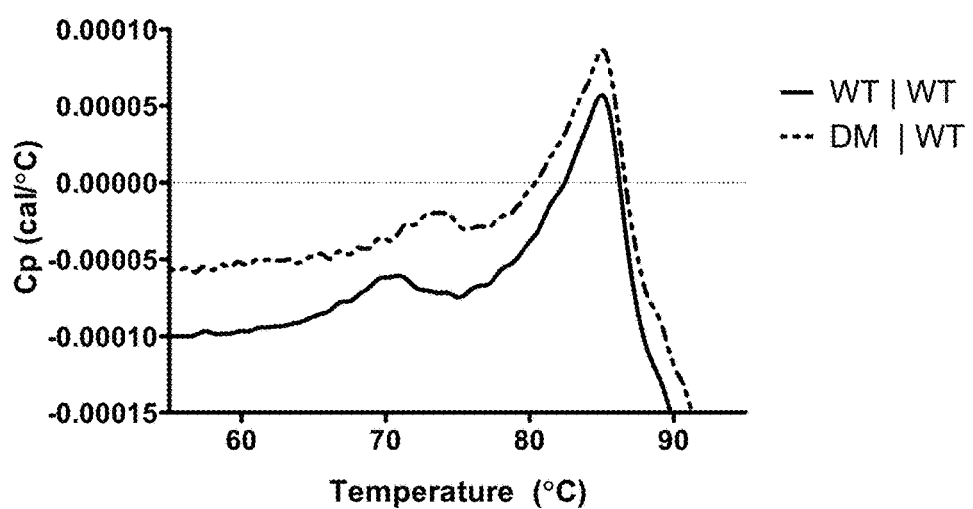

DSC analysis of wildtype (WT) IgG1 resulted in two peaks as shown in FIG. 21 (indicated as WT|WT for CH2|CH3). Tm1 at 70.9° C. corresponds to the melting of the CH2 domain, while the peak at 85.0° C. (Tm2) represents the melting of the Fabs and CH3 domain. The DSC graph of an IgG1 with identical Fabs comprising two mutations (L235G, G236R) in the CH2 domain (DM|WT) shows a very similar Tm2 peak at 85.0° C. The Tm1 peak however has shifted to 73.5° C., indicating that these mutations increase the stability of the CH2 domain significantly. Since the CH2 domain is not only the most fragile domain of a WT IgG1, but also of a CH3-engineered bispecific IgG1, it can be concluded that the L235G, G236R engineered CH2 domain also confers additional stability to the CD3×CLEC12A bispecific IgG antibodies carrying these CH2 mutations.

The invention claimed is:

1. A method of treating a hematological disease in a subject, comprising administering to the subject a therapeutically effective amount of a bispecific antibody which comprises a first heavy chain variable region and light chain variable region combination (VH/VL) that binds human CD3 and a second VH/VL combination that binds a tumor-antigen,
wherein the heavy chain variable region of said first VH/VL combination comprises the complementarity regions, HCDR1, HCDR2 and HCDR3, of the VH set forth in SEQ ID NO: 1, SEQ ID NO: 2, SEQ ID NO: 4, SEQ ID NO: 5, SEQ ID NO: 6, SEQ ID NO: 49, SEQ ID NO: 50, SEQ ID NO: 51, SEQ ID NO: 53, SEQ ID NO: 54, SEQ ID NO: 55, SEQ ID NO: 57, SEQ ID NO: 58 or SEQ ID NO: 59; and
wherein the light chain variable region of the first VH/VL combination comprises the complementarity regions, LCDR1, LCDR2 and LCDR3, of the VL set forth in SEQ ID NO: 16.

2. The method of claim 1, wherein the hematological disease is a leukemia or lymphoma.

3. The method of claim 2, wherein the leukemia or lymphoma is acute myeloid leukemia (AML), myelodysplastic syndrome (MDS) chronic myelogenous leukemia (CML), B-cell acute lymphocytic leukemia (B-ALL), T-cell acute lymphoblastic leukemia (T-ALL), Hodgkin's lymphoma, non-Hodgkin's lymphomas, mantle cell lymphoma, myelodysplastic syndrome (MDS), or multiple myeloma (MM).

4. The method of claim 3, wherein the hematological disease is AML.

5. The method of claim 4, wherein the AML is unresponsive to prior therapy.

6. The method of claim 5, wherein the prior therapy is chemotherapy.

7. The method of claim 1, wherein the heavy chain variable region of said first VH/VL comprises an amino acid sequence selected from SEQ ID NOs: 1, 2, 4, 5, 6, 49-51, 53-55 and 57-59.

8. The method of claim 1, wherein the heavy chain variable region of said first VH/VL comprises the amino acid sequence set forth in SEQ ID NO: 1.

9. The method of claim 1, wherein the light chain variable region of said first VH/VL comprises the amino acid sequence set forth in SEQ ID NO: 16.

10. The method of claim 7, wherein the heavy chain variable region of said first VH/VL comprises the amino acid sequence set forth in SEQ ID NO: 1, and the light chain variable region of said first VH/VL comprises the amino acid sequence set forth in SEQ ID NO: 16.

11. The method of claim 1, wherein said light chain variable region of said first VH/VL combination, said second VH/VL combination, or both said first and second VH/VL combination comprises a common light chain variable region.

12. The method of claim 11, wherein said common light chain variable region comprises an O12/IgVκ1-39 light chain variable region.

13. The method of claim 12, wherein said common light chain variable region is a germline O12/IgVκ1-39*01 variable region.

14. The method of claim 13, wherein said common light chain variable region comprises the kappa light chain IgVκ1-39*01/IGJκ1*O1 or IgVκ1-39*01/IGJκ5*01.

15. The method of claim 14, wherein said common light chain variable region comprises the germline kappa light chain IgVκ1-39*01/IGJκ1*01 or IgVκ1-39*01/IGJκ5*01.

16. The method of claim 1, wherein said second VH/VL combination binds a tumor-antigen selected from the group consisting of: B-Cell Maturation Antigen (BCMA), CD19, CD20, CD30, CD33, CD38, CD44, CD123, CD138, Carcinoembryonic Antigen (CEA), C-Type Lectin Domain Family 12, Member A (CLEC12A), Citrate Synthase 1 (CS-1), Epidermal Growth Factor Receptor (EGFR), Epidermal Growth Factor Receptor Variant III (EGFRvIII), Epithelial Cell Adhesion Molecule (EPCAM), Delta-like ligand 3 (DLL3), Leucine-Rich Repeat Containing G Protein-Coupled Receptor 5 (LGR5), Mesothelin (MSLN), Folate Receptor 1 (FOLR1), Folate receptor 3 (FOLR3), Receptor Tyrosine-Protein Kinase erbB-2 (HER2), Bone Marrow Stromal Cell Antigen 2 (HM1.24), Sperm Mitochondria-Associated Cysteine-Rich Protein (MCSP), and Prostate-Specific Membrane Antigen (PSMA).

17. The method of claim 16, wherein said second VH/VL combination binds CLEC12A.

18. The method of claim 1, wherein said bispecific antibody comprises a human constant region and human variable domains.

19. The method of claim 1, wherein said bispecific antibody comprises two different immunoglobulin heavy chains with compatible heterodimerization domains.

20. The method of claim 19, wherein said compatible heterodimerization domains are compatible immunoglobulin heavy chain CH3 heterodimerization domains.

21. The method of claim 1, wherein said bispecific antibody is an IgG antibody with a mutant CH2 and/or lower hinge domain such that interaction of said bispecific IgG antibody to a Fc-gamma receptor is reduced.

22. The method of claim 21, wherein said mutant CH2 and/or lower hinge domain comprises an amino acid substitution at positions 235 and/or 236.

23. The method of claim 22, wherein said amino acid substitution is a L235G and/or G236R substitution.

24. A method of treating a hematological disease in a subject, comprising administering to the subject a therapeutically effective amount of a bispecific antibody which comprises a first heavy chain variable region and light chain variable region combination (VH/VL) that binds human CD3 and a second VH/VL combination that binds a tumor-antigen, wherein said first VH/VL combination comprises:
(a) a heavy chain variable region comprising a HCDR1 comprising the amino acid sequence GFTFSSYG (SEQ ID NO: 10), a HCDR2 comprising the amino acid sequence IWYNARKQ (SEQ ID NO: 11), and a HCDR3 comprising the amino acid sequence GTGYNWFDP (SEQ ID NO: 12); and
(b) an O12/IgVκ1-39 light chain variable region comprising an LCDR1 comprising the amino acid sequence QSISSY (SEQ ID NO: 18), an LCDR2 comprising the amino acid sequence AAS, and an LCDR3 comprising the amino acid sequence QQSYSTP (SEQ ID NO: 19).

25. The method of claim 24, wherein the hematological disease is AML.

* * * * *

SEQUENCE LISTING

<160> NUMBER OF SEQ ID NOS: 64

<210> SEQ ID NO 1
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 1

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 2

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Thr Arg Lys Gln Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 3

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Ser Gly Arg Lys Gln Asp Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Thr Arg Gly Thr Gly Tyr Asn Trp Phe Asp Pro Trp Gly Gln Gly Thr
                100                 105                 110

Leu Val Thr Val Ser Ser
            115

<210> SEQ ID NO 4
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 4

Gln Val Gln Leu Val Gln Ser Gly Gly Gly Val Val Gln Pro Gly Arg
 1                5                  10                  15

Ser Leu Arg Leu Ser Cys Val Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Ala Ile Trp Tyr His Gly Arg Lys Gln Asp Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Thr Arg Gly Thr Gly Tyr Asn Trp Phe Asp Pro Trp Gly Gln Gly Thr
                100                 105                 110

Leu Val Thr Val Ser Ser
            115

<210> SEQ ID NO 5
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 5

Gln Val Gln Leu Val Gln Ser Gly Gly Gly Val Val Gln Pro Gly Arg
 1                5                  10                  15

Ser Leu Arg Leu Ser Cys Val Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Ala Ile Trp Tyr Asp Gly Arg Lys Gln Asp Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Thr Arg Gly Thr Gly Tyr Asn Trp Phe Asp Pro Trp Gly Gln Gly Thr
                100                 105                 110
```

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: human CD3 binding antibody

<400> SEQUENCE: 6

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr His Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Synthetic: heavy chain variable region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
            100                 105                 110

Leu Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Synthetic: heavy chain variable region -continued

```
<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Gly Asp Glu Phe Asp Tyr Trp Gly Gln Gly Thr
            100                 105                 110

Leu Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Synthetic: heavy chain variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Tyr Phe Ala Asp Ala Phe Asp Tyr Trp Gly Gln Gly
            100                 105                 110

Thr Leu Val Thr Val Ser Ser
        115

<210> SEQ ID NO 10
<211> LENGTH: 8
<212> TYPE: PRT
<213> ORGANISM: Artificial Sequence
<220> FEATURE:
<223> OTHER INFORMATION: Synthetic: CDR1

<400> SEQUENCE: 10

Gly Phe Thr Phe Ser Ser Tyr Gly
1               5

<210> SEQ ID NO 11
<211> LENGTH: 8
<212> TYPE: PRT
<213> ORGANISM: Artificial Sequence
<220> FEATURE:
```

```
<223> OTHER INFORMATION: Synthetic: CDR2

<400> SEQUENCE: 11

Ile Trp Tyr Asn Ala Arg Lys Gln
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic: CDR3

<400> SEQUENCE: 12

Gly Thr Gly Tyr Asn Trp Phe Asp Pro
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic: CDR1

<400> SEQUENCE: 13

Gly Tyr Thr Phe Thr Ser Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic: CDR2

<400> SEQUENCE: 14

Ile Asn Pro Ser Gly Gly Ser Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic: CDR3

<400> SEQUENCE: 15

Gly Thr Thr Gly Asp Trp Phe Asp Tyr
1               5

<210> SEQ ID NO 16
<211> LENGTH: 107
<212> TYPE: PRT
<213> ORGANISM: Artificial Sequence
<220> FEATURE:
<223> OTHER INFORMATION: Synthetic: light chain variable region

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys
            100                 105

<210> SEQ ID NO 17
<211> LENGTH: 108
<212> TYPE: PRT
<213> ORGANISM: Artificial Sequence
<220> FEATURE:
<223> OTHER INFORMATION: Synthetic: light chain variable region

<400> SEQUENCE: 17

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 18
<211> LENGTH: 6
<212> TYPE: PRT
<213> ORGANISM: Artificial Sequence
<220> FEATURE:
<223> OTHER INFORMATION: Synthetic: CDR1

<400> SEQUENCE: 18

Gln Ser Ile Ser Ser Tyr
 1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: CDR3

<400> SEQUENCE: 19

Gln Gln Ser Tyr Ser Thr Pro
 1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic: DEKK heterodimer

<400> SEQUENCE: 20

Asp Glu Lys Lys
```

```
1

<210> SEQ ID NO 21
<211> LENGTH: 4
<212> TYPE: PRT
<213> ORGANISM: Artificial Sequence
<220> FEATURE:
<223> OTHER INFORMATION: Synthetic: KKKK homodimer

<400> SEQUENCE: 21

Lys Lys Lys Lys
1

<210> SEQ ID NO 22
<211> LENGTH: 4
<212> TYPE: PRT
<213> ORGANISM: Artificial Sequence
<220> FEATURE:
<223> OTHER INFORMATION: Synthetic: DEDE homodimer

<400> SEQUENCE: 22

Asp Glu Asp Glu
1

<210> SEQ ID NO 23
<211> LENGTH: 7
<212> TYPE: PRT
<213> ORGANISM: Artificial Sequence
<220> FEATURE:
<223> OTHER INFORMATION: Synthetic: CDR2 with deamidation motif

<400> SEQUENCE: 23

Trp Tyr Asn Gly Arg Lys Gln
1               5

<210> SEQ ID NO 24
<211> LENGTH: 118
<212> TYPE: PRT
<213> ORGANISM: Artificial Sequence
<220> FEATURE:
<223> OTHER INFORMATION: Synthetic: VH3056

<400> SEQUENCE: 24

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 25
<211> LENGTH: 98
<212> TYPE: PRT
```

<213> ORGANISM: Artificial Sequence
<220> FEATURE:
<223> OTHER INFORMATION: Synthetic: VH 3-33 germline sequence

<400> SEQUENCE: 25

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 26
<211> LENGTH: 118
<212> TYPE: PRT
<213> ORGANISM: Artificial Sequence
<220> FEATURE:
<223> OTHER INFORMATION: Synthetic: VH of MF3872

<400> SEQUENCE: 26

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Ser Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: Synthetic: VH of MF3873

<400> SEQUENCE: 27

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

Ala Ala Ile Trp Tyr Gln Gly Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 28
<211> LENGTH: 118
<212> TYPE: PRT
<213> ORGANISM: Artificial Sequence
<220> FEATURE:
<223> OTHER INFORMATION: Synthetic: VH of MF3905

<400> SEQUENCE: 28

Gln Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ala Ile Trp Tyr Gly Gly Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 29
<211> LENGTH: 118
<212> TYPE: PRT
<213> ORGANISM: Artificial Sequence
<220> FEATURE:
<223> OTHER INFORMATION: Synthetic: VH of MF3874

<400> SEQUENCE: 29

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ala Ile Trp Tyr Asn Gly Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

```
Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic: VH of MF3878

<400> SEQUENCE: 30

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic: VH of MF3883

<400> SEQUENCE: 31

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: Synthetic: VH of MF3886
```

<400> SEQUENCE: 32

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
            115

<210> SEQ ID NO 33
<211> LENGTH: 118
<212> TYPE: PRT
<213> ORGANISM: Artificial Sequence
<220> FEATURE:
<223> OTHER INFORMATION: Synthetic: VH of MF3891

<400> SEQUENCE: 33

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
            115

<210> SEQ ID NO 34
<211> LENGTH: 118
<212> TYPE: PRT
<213> ORGANISM: Artificial Sequence
<220> FEATURE:
<223> OTHER INFORMATION: Synthetic: VH of MF5192

<400> SEQUENCE: 34

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr His Gly Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Thr
                    85                  90                  95

Ala Arg Gly Thr Gly Tyr Asn Trp Phe Asp Pro Trp Gly Gln Gly Thr
                100                 105                 110

Leu Val Thr Val Ser Ser
                115

<210> SEQ ID NO 35
<211> LENGTH: 118
<212> TYPE: PRT
<213> ORGANISM: Artificial Sequence
<220> FEATURE:
<223> OTHER INFORMATION: Synthetic: VH of MF5193

<400> SEQUENCE: 35

Gln Val Gln Leu Val Gln Ser Gly Gly Gly Val Val Gln Pro Gly Arg
 1                   5                  10                  15

Ser Leu Arg Leu Ser Cys Val Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Trp Tyr His Ala Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Thr
                    85                  90                  95

Ala Arg Gly Thr Gly Tyr Asn Trp Phe Asp Pro Trp Gly Gln Gly Thr
                100                 105                 110

Leu Val Thr Val Ser Ser
                115

<210> SEQ ID NO 36
<211> LENGTH: 118
<212> TYPE: PRT
<213> ORGANISM: Artificial Sequence
<220> FEATURE:
<223> OTHER INFORMATION: Synthetic: VH of MF5194

<400> SEQUENCE: 36

Gln Val Gln Leu Val Gln Ser Gly Gly Gly Val Val Gln Pro Gly Arg
 1                   5                  10                  15

Ser Leu Arg Leu Ser Cys Val Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Trp Tyr His Thr Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Thr
                    85                  90                  95

Ala Arg Gly Thr Gly Tyr Asn Trp Phe Asp Pro Trp Gly Gln Gly Thr

Leu Val Thr Val Ser Ser
                115

<210> SEQ ID NO 37
<211> LENGTH: 118
<212> TYPE: PRT
<213> ORGANISM: Artificial Sequence
<220> FEATURE:
<223> OTHER INFORMATION: Synthetic: VH of MF5195

<400> SEQUENCE: 37

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr His Asn Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Thr
                85                  90                  95

Ala Arg Gly Thr Gly Tyr Asn Trp Phe Asp Pro Trp Gly Gln Gly Thr
            100                 105                 110

Leu Val Thr Val Ser Ser
                115

<210> SEQ ID NO 38
<211> LENGTH: 118
<212> TYPE: PRT
<213> ORGANISM: Artificial Sequence
<220> FEATURE:
<223> OTHER INFORMATION: Synthetic: VH of MF5196

<400> SEQUENCE: 38

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Thr
                85                  90                  95

Ala Arg Gly Thr Gly Tyr Asn Trp Phe Asp Pro Trp Gly Gln Gly Thr
            100                 105                 110

Leu Val Thr Val Ser Ser
                115

<210> SEQ ID NO 39
<211> LENGTH: 118
<212> TYPE: PRT
<213> ORGANISM: Artificial Sequence
<220> FEATURE:

<223> OTHER INFORMATION: Synthetic: VH of MF5197

<400> SEQUENCE: 39

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Thr Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Thr
                85                  90                  95

Ala Arg Gly Thr Gly Tyr Asn Trp Phe Asp Pro Trp Gly Gln Gly Thr
            100                 105                 110

Leu Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Synthetic: 15C3 VH

<400> SEQUENCE: 40

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Thr Gly Tyr Asn Trp Phe Asp Pro Trp Gly Gln Gly Thr Leu
            100                 105                 110

Val Thr Val Ser Ser
        115

<210> SEQ ID NO 41
<211> LENGTH: 107
<212> TYPE: PRT
<213> ORGANISM: Artificial Sequence
<220> FEATURE:
<223> OTHER INFORMATION: Synthetic: 15C3 VL1 - IGKV3-11*

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                    35                  40                  45
Tyr Asp Ala Ser Asn Arg Ala Thr Gly Ile Pro Ala Ser Phe Ser Gly
                50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
                100                 105
```

<210> SEQ ID NO 42
<211> LENGTH: 107
<212> TYPE: PRT
<213> ORGANISM: Artificial Sequence
<220> FEATURE:
<223> OTHER INFORMATION: Synthetic: 15C3 VL2 - IGKV1-13 (MF3055)

<400> SEQUENCE: 42

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
                100                 105
```

<210> SEQ ID NO 43
<211> LENGTH: 107
<212> TYPE: PRT
<213> ORGANISM: Artificial Sequence
<220> FEATURE:
<223> OTHER INFORMATION: Synthetic: IGKV1-39 (MF3056)

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
                100                 105
```

<210> SEQ ID NO 44
<211> LENGTH: 95

```
<212> TYPE: PRT
<213> ORGANISM: Artificial Sequence
<220> FEATURE:
<223> OTHER INFORMATION: Synthetic: IGKV1-39A

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 45
<211> LENGTH: 107
<212> TYPE: PRT
<213> ORGANISM: Artificial Sequence
<220> FEATURE:
<223> OTHER INFORMATION: Synthetic: IGKV1-39/jk1

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 46
<211> LENGTH: 108
<212> TYPE: PRT
<213> ORGANISM: Artificial Sequence
<220> FEATURE:
<223> OTHER INFORMATION: Synthetic: IGKV1-39/jk5

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Pro Pro
                        85                  90                  95

Ile Thr Phe Gly Gln Gly Thr Arg Leu Glu Ile Lys
                100                 105
```

<210> SEQ ID NO 47
<211> LENGTH: 127
<212> TYPE: PRT
<213> ORGANISM: Artificial Sequence
<220> FEATURE:
<223> OTHER INFORMATION: Synthetic: MF1337_VH

<400> SEQUENCE: 47

```
Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
                20                  25                  30

Asp Ile Asn Trp Val Arg Gln Ala Pro Gly Gln Gly Leu Glu Trp Met
            35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
                100                 105                 110

Ala Leu Asp Val Trp Gly Gln Gly Thr Thr Val Thr Val Ser Ser
            115                 120                 125
```

<210> SEQ ID NO 48
<211> LENGTH: 118
<212> TYPE: PRT
<213> ORGANISM: Artificial Sequence
<220> FEATURE:
<223> OTHER INFORMATION: Synthetic: MF4327_VH

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
                100                 105                 110

Leu Val Thr Val Ser Ser
            115
```

<210> SEQ ID NO 49
<211> LENGTH: 118

<212> TYPE: PRT
<213> ORGANISM: Artificial Sequence
<220> FEATURE:
<223> OTHER INFORMATION: Synthetic: MF5603_VH

<400> SEQUENCE: 49

Gln Val Gln Leu Val Gln Ser Gly Gly Gly Val Val Gln Pro Gly Arg
1               5                   10                  15
Ser Leu Arg Leu Ser Cys Val Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ala Ile Trp Tyr Asn Ala Arg Lys Gln Glu Tyr Ile Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Gly Thr Gly Tyr Asn Trp Phe Asp Pro Trp Gly Gln Gly Thr
            100                 105                 110
Leu Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic: MF5616_VH

<400> SEQUENCE: 50

Gln Val Gln Leu Val Gln Ser Gly Gly Gly Val Val Gln Pro Gly Arg
1               5                   10                  15
Ser Leu Arg Leu Ser Cys Val Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ala Ile Trp Tyr Asn Ala Arg Lys Gln Glu Tyr Asn Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Gly Thr Gly Tyr Asn Trp Phe Asp Pro Trp Gly Gln Gly Thr
            100                 105                 110
Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Synthetic: MF5626_VH

<400> SEQUENCE: 51

Gln Val Gln Leu Val Gln Ser Gly Gly Gly Val Val Gln Pro Gly Arg
1               5                   10                  15
Ser Leu Arg Leu Ser Cys Val Ala Ser Gly Phe Thr Phe Ser Ser Tyr

```
                20                  25                  30
Gly Met His Trp Val Arg Gln Ala Pro Gly Lys Gly Leu Glu Trp Val
            35                  40                  45

Ala Ala Ile Trp Tyr Asn Ala Arg Lys Gln Glu Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthetic: MF5630_VH

<400> SEQUENCE: 52

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Tyr Asp Pro Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic: MF5648_VH

<400> SEQUENCE: 53

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Leu Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Synthetic: MF5661_VH

<400> SEQUENCE: 54

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Gln Ile Trp Tyr Asn Ala Arg Lys Gln Glu Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic: MF5694_VH

<400> SEQUENCE: 55

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 56

```
<211> LENGTH: 118
<212> TYPE: PRT
<213> ORGANISM: Artificial Sequence
<220> FEATURE:
<223> OTHER INFORMATION: Synthetic: consensus fig. 25

<400> SEQUENCE: 56

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Ala Arg Lys Gln Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic: MF5351_VH

<400> SEQUENCE: 57

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Met Ile Trp Tyr Asp Gly Lys Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic: MF5354_VH

<400> SEQUENCE: 58

Gln Val Gln Leu Val Gln Ser Gly Gly Gly Val Val Gln Pro Gly Arg
1               5                   10                  15
```

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
            35                  40                  45

Ala Gln Ile Tyr Tyr Asp Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 59
<211> LENGTH: 118
<212> TYPE: PRT
<213> ORGANISM: Artificial Sequence
<220> FEATURE:
<223> OTHER INFORMATION: Synthetic: MF5356_VH

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
            20                  25                  30

Gly Met His Trp Val Arg Gln Ala Pro Gly Lys Gly Leu Glu Trp Val
            35                  40                  45

Ala Gln Ile Trp His Asp Gly Arg Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 60
<211> LENGTH: 118
<212> TYPE: PRT
<213> ORGANISM: Artificial Sequence
<220> FEATURE:
<223> OTHER INFORMATION: Synthetic: consensus Fig. 28

<400> SEQUENCE: 60

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Gln Ile Trp Tyr Asp Gly Arg Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(118)
<223> OTHER INFORMATION: Can have 0-10, preferably 0-5, amino acid
      insertions, deletions, substitutions, additions or a combination
      thereof at one or more positions other than the position indicated
      by XX at positions 54 and 55
<220> FEATURE:
<221> NAME/KEY: misc_feature
<222> LOCATION: (54)..(55)
<223> OTHER INFORMATION: XX can be any combination of NA, NT, SG, HG,
      DG, or HA

<400> SEQUENCE: 61

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Xaa Xaa Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 62
<211> LENGTH: 89
<212> TYPE: PRT
<213> ORGANISM: Artificial Sequence
<220> FEATURE:
<223> OTHER INFORMATION: Synthetic: consensus of Fig. 6

<400> SEQUENCE: 62

Gln Val Gln Leu Val Ser Gly Gly Gly Val Val Gln Pro Gly Arg Ser
1               5                   10                  15

Leu Arg Leu Ser Cys Ala Ser Gly Phe Thr Phe Ser Ser Tyr Gly Met
            20                  25                  30

His Trp Val Arg Gln Ala Pro Gly Lys Gly Leu Glu Trp Val Ala Ile
        35                  40                  45

Trp Tyr Gly Tyr Ala Asp Ser Val Lys Gly Arg Phe Thr Ile Ser Arg
    50                  55                  60

Asp Asn Ser Lys Asn Thr Leu Tyr Leu Gln Met Asn Ser Leu Arg Ala
```

```
                65                  70                  75                  80
Glu Asp Thr Ala Val Tyr Tyr Cys Arg
                    85

<210> SEQ ID NO 63
<211> LENGTH: 118
<212> TYPE: PRT
<213> ORGANISM: Artificial Sequence
<220> FEATURE:
<223> OTHER INFORMATION: Synthetic: consensus of Fig. 9

<400> SEQUENCE: 63

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Synthetic: Consensus of Fig. 12

<400> SEQUENCE: 64

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr His Ala Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115
```